(12) United States Patent
Margel et al.

(10) Patent No.: US 10,072,161 B2
(45) Date of Patent: Sep. 11, 2018

(54) POLYAMIDE NANOPARTICLES AND USES THEREOF

(71) Applicant: Bar-Ilan University, Ramat Gan (IL)

(72) Inventors: Shlomo Margel, Rehovot (IL); Ehud Banin, Tel Aviv (IL); Ori Gutman, Lod (IL); Michal Natan, Kfar Saba (IL)

(73) Assignee: BAR ILAN UNIVERSITY, Ramat Gan (IL)

( * ) Notice: Subject to any disclaimer, the term of this patent is extended or adjusted under 35 U.S.C. 154(b) by 0 days.

(21) Appl. No.: 15/113,313

(22) PCT Filed: Jan. 22, 2015

(86) PCT No.: PCT/IL2015/050080
§ 371 (c)(1),
(2) Date: Jul. 21, 2016

(87) PCT Pub. No.: WO2015/111055
PCT Pub. Date: Jul. 30, 2015

(65) Prior Publication Data
US 2017/0009084 A1 Jan. 12, 2017

Related U.S. Application Data

(60) Provisional application No. 61/930,498, filed on Jan. 23, 2014.

(51) Int. Cl.
| | |
|---|---|
| C09D 5/16 | (2006.01) |
| A01N 37/28 | (2006.01) |
| C09D 133/26 | (2006.01) |
| C09D 5/14 | (2006.01) |
| C08F 220/56 | (2006.01) |
| C08F 8/18 | (2006.01) |
| C08F 4/40 | (2006.01) |
| B82Y 5/00 | (2011.01) |

(52) U.S. Cl.
CPC ......... *C09D 5/1662* (2013.01); *A01N 37/28* (2013.01); *C08F 4/40* (2013.01); *C08F 8/18* (2013.01); *C08F 220/56* (2013.01); *C09D 5/14* (2013.01); *C09D 133/26* (2013.01); *B82Y 5/00* (2013.01); *C08F 2500/26* (2013.01); *C08F 2800/20* (2013.01); *C08F 2810/20* (2013.01)

(58) Field of Classification Search
CPC ...... C08F 220/56; C08F 222/385; C08F 8/22; C08F 2500/26; C08F 2810/20; B82Y 5/00; C09D 133/26; C09D 5/14; C09D 5/1662
See application file for complete search history.

(56) References Cited

U.S. PATENT DOCUMENTS

| | | | |
|---|---|---|---|
| 3,314,909 | A | 4/1967 | Whitfield |
| 4,356,289 | A | 10/1982 | Zengel et al. |
| 8,211,361 | B2 | 7/2012 | Sun et al. |
| 2008/0268189 | A1 | 10/2008 | Sun et al. |

FOREIGN PATENT DOCUMENTS

| | | | | |
|---|---|---|---|---|
| CA | 849614 A | | 8/1970 | |
| EP | 2026063 | * | 2/2009 | ........... G01N 27/447 |
| EP | 2026063 A1 | | 2/2009 | |
| WO | 99/00187 A1 | | 1/1999 | |
| WO | 02/16453 A1 | | 2/2002 | |
| WO | 2004/003036 A1 | | 1/2004 | |

OTHER PUBLICATIONS

Menter ("Acrylamide Polymerization—A Practical Approach", Bio-Rad-Laboratories, Electrophoresis 1156, 2000).*
Caulfield et al. (Polymer 44 (2003) 3817-3826).*
Lopour et al. (Die Angewandte Makromolekulare Chemie 243 (1996) 151-159 (Nr.4256)).*
Paul Menter, "Acrylamide Polymerization—A Practical Approach", Bio-Rad Laboratories, 2000.
Ori Gutman, "Characterization and antibacterial properties of N-halamine derivatized cross-linked polymethacrylamide nanoparticles", Biomaterials, vol. 35, No. 19, pp. 5079-5087, 2014.

\* cited by examiner

*Primary Examiner* — Anna R Falkowitz
(74) *Attorney, Agent, or Firm* — The Roy Gross Law Firm, LLC; Roy Gross

(57) ABSTRACT

Nanoparticles of N-halamine-derivatized crosslinked polyamide. Process of preparing the polymeric nanoparticles per se and incorporated in or on a substrate. Uses of the polymeric nanoparticles and of substrates incorporating same, particularly for reducing a formation of organic based contaminants, e.g., load of a microorganism or of a biofilm.

20 Claims, 46 Drawing Sheets

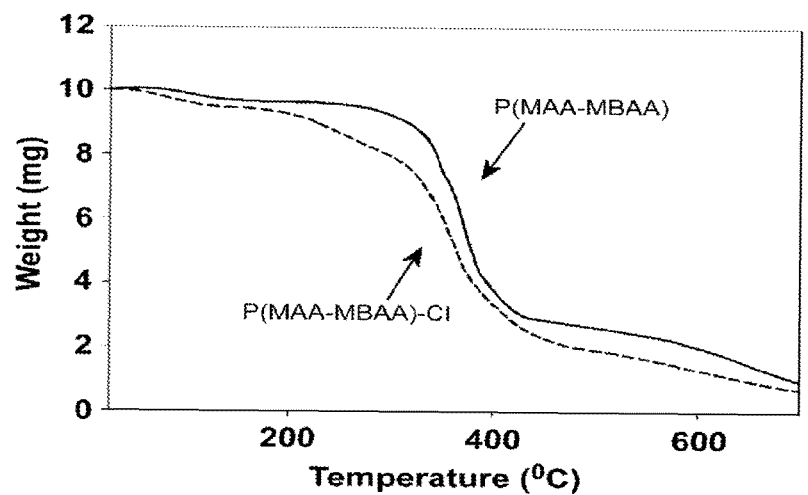
FIG. 3
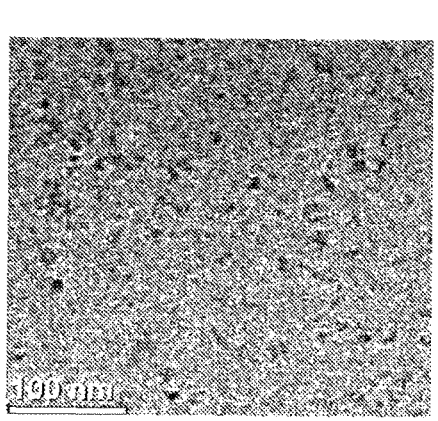 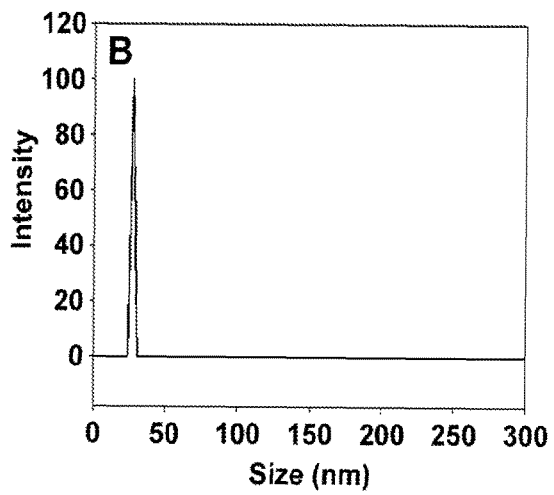
FIG. 4A　　　　　　　　FIG. 4B

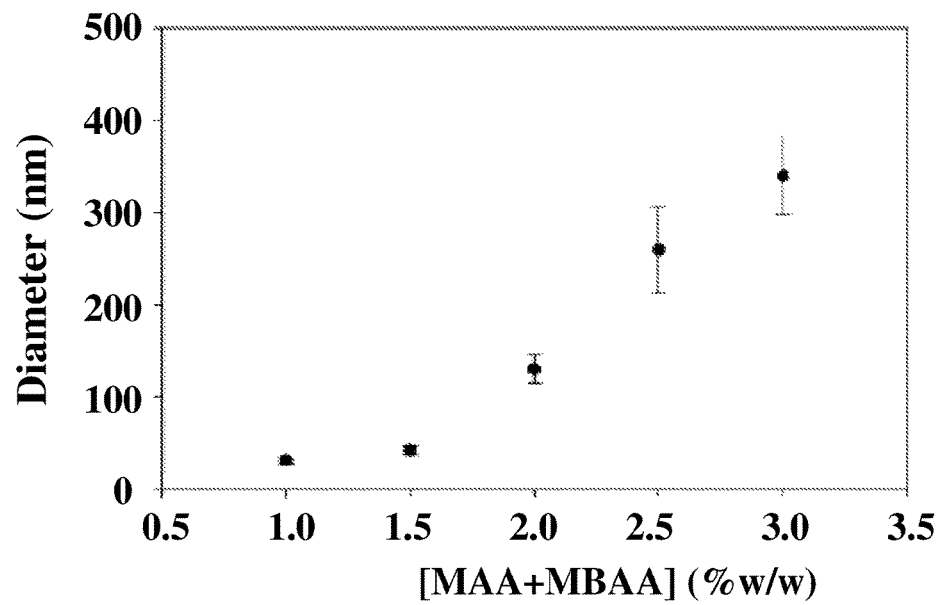
FIG. 5
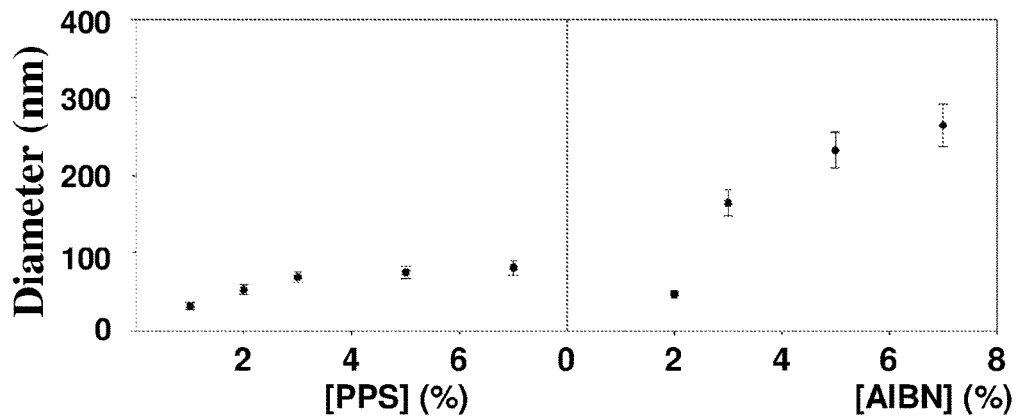
FIG. 6A                    FIG. 6B

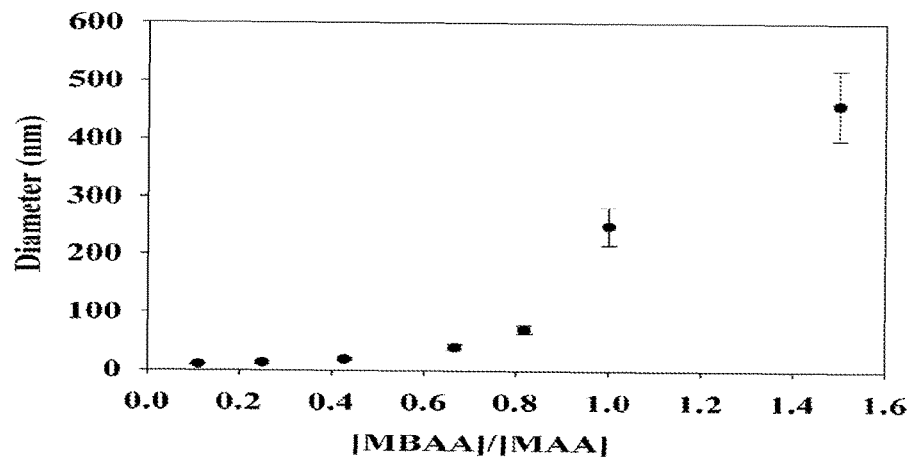
FIG. 7
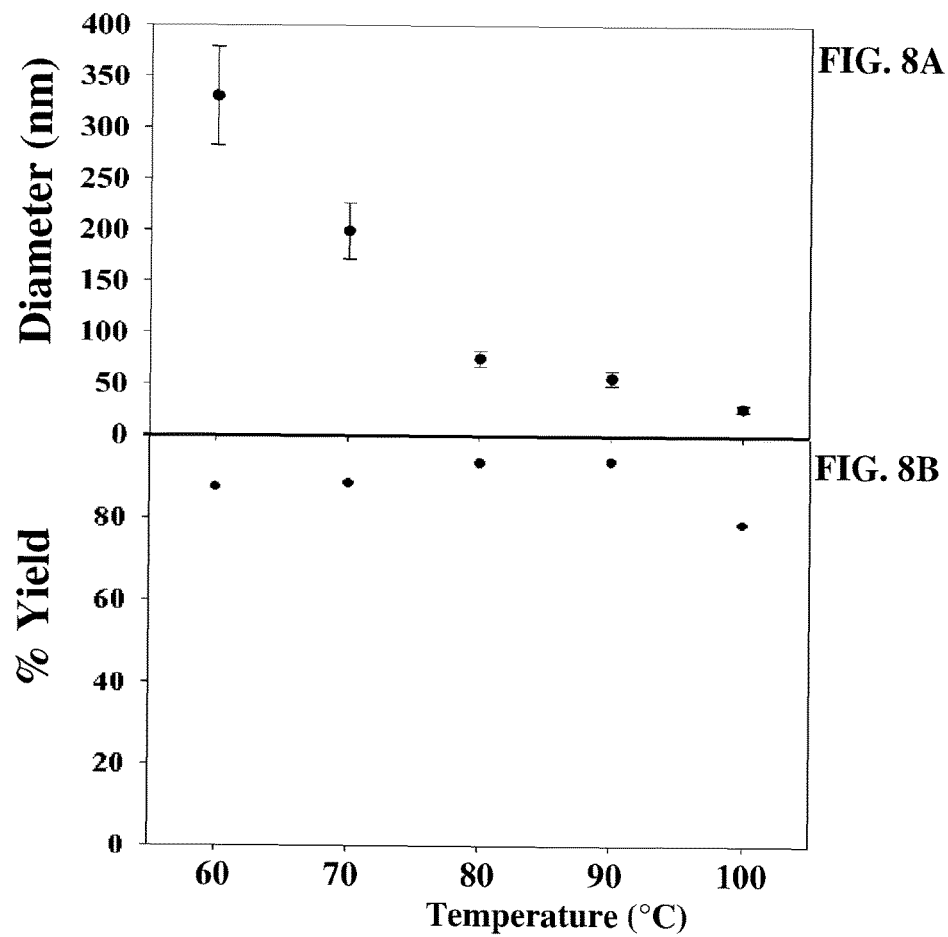
FIG. 8A
FIG. 8B

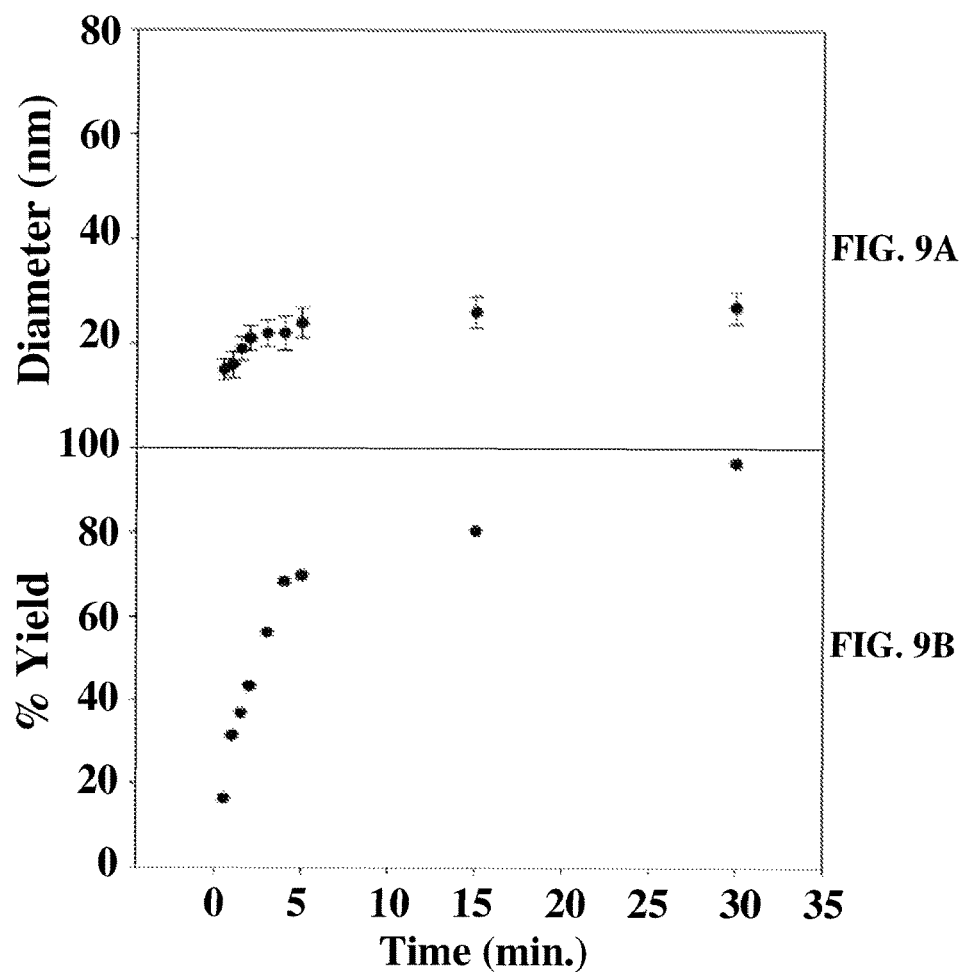
FIG. 9A
FIG. 9B
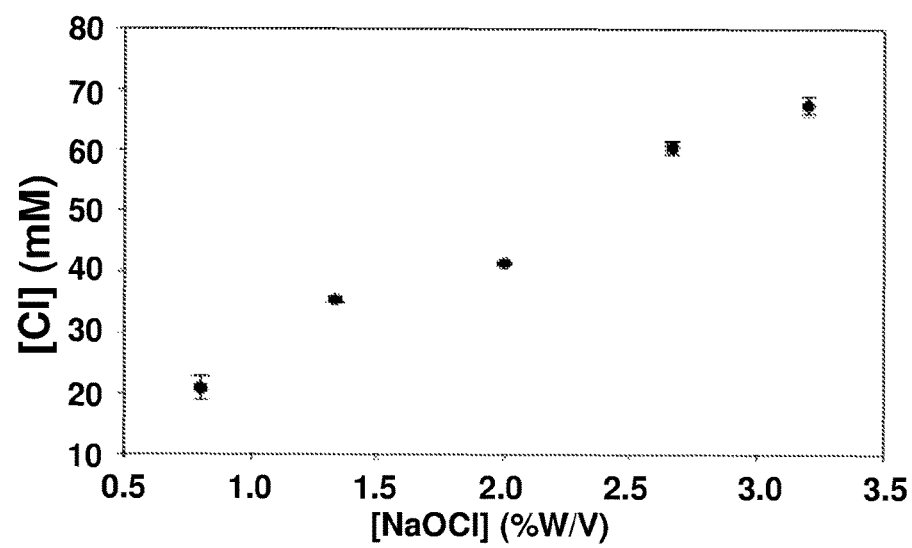
FIG. 10

O O

I O

I/I O/I I/O O/O

CONTROL
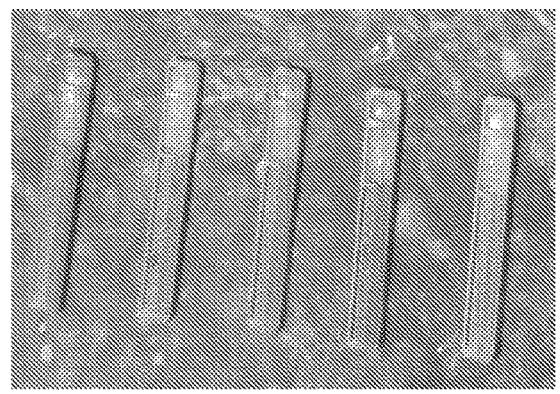
TREATED
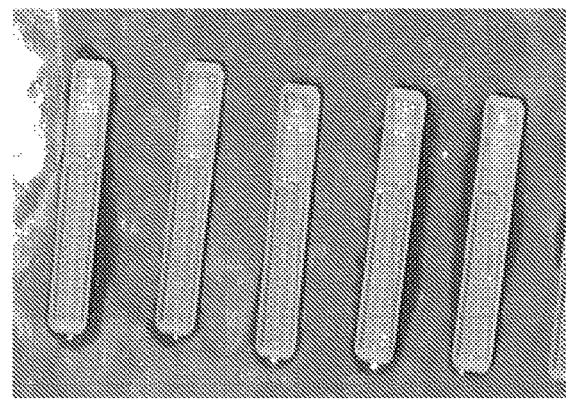
REGENERATION
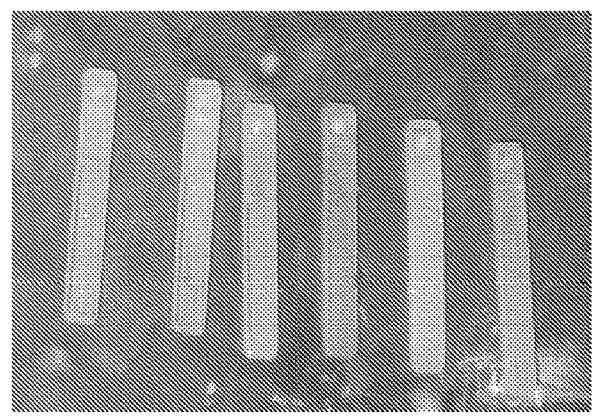
FIG. 46

POLYAMIDE NANOPARTICLES AND USES THEREOF

FIELD OF THE INVENTION

The present invention, in some embodiments thereof, relates to nanosized crosslinked polymeric backbones, and more particularly, but not exclusively, to nanosized N-halamine-derivatized crosslinked polyamide and uses thereof in, for example, reducing or preventing organic-based contaminant.

BACKGROUND OF THE INVENTION

Various organic antimicrobial agents, such as quaternary ammonium salts, phosphonium salts, and N-halamine compounds, have been extensively investigated over the past 20 years. Compared with halogens, which are inorganic, N-halamines are more stable and less corrosive, and their numerous sought-after qualities (i.e., effectiveness at killing toward a broad spectrum of microorganisms, long-term stability, the possibility of recycling, low cost, and safety for humans and the environment) make N-halamines particularly attractive. The dissociation constant of N-halamine compounds in water is relatively low and varies based on chemical structure in the order amine<amide<imide. However, in the presence of microorganisms, oxidative halogen e.g., Cl transfer from the N-halamine bond to the microorganism is significantly favored over hydrolysis. Amine-halamine is the most stable of all halamine bonds but has a slower bactericidal rate than amide-halamine. In contrast, imide-halamine has a rapid bactericidal rate because it is the least stable of all halamine bonds and can rapidly release active Cl into the medium.

Compounds containing amide-halamine bonds are considered the most practical for industrial applications because they exhibit a moderate rate of transfer of the oxidative Cl from the N-halamine to bacteria in aqueous solution and thus provide reasonably rapid bactericidal activity. Although the hydrolysis constant of amidehal amines is in the range of $10^{-8}$, the Cl transfer to the bacteria is the more favorable process.

Bacterial attachment to surfaces leading to the formation of communities of bacterial cells is a major problem in many diverse settings. This sessile community of microorganisms, also termed a biofilm, is attached to an interface, or to each other, and embedded in an exopolymeric matrix. It manifests an altered mode of growth and transcribes genes that free-living microorganisms do not transcribe. The most characteristic phenotype of the biofilm mode of growth is its inherent resistance to disinfection, antimicrobial treatment and immune response killing.

The inherent resistance of biofilms to killing and their pervasive involvement in product contamination, pipe clogging and implant-related infections has prompted for various industrial applications such as drinking water distribution systems and food packaging.

U.S. Pat. No. 8,211,361 discloses one or more acyclic-amine structures being halogenated to form one or more acyclic N-halamine structure, and uses same for functionalizing a surface of an object to control microbial contamination of a surface.

CN Patent No. 103,044,611 discloses polymeric antibacterial nano-particles and magnetic antibacterial nano-particles containing halamine functional groups.

SUMMARY OF THE INVENTION

In a search for novel methodologies for fabricating long-lasting organic antimicrobial agents, the present inventors have developed a novel nanosized crosslinked polymers, and more particularly, but not exclusively, N-halamine-derivatized crosslinked polyamide nanoparticles (NPs). The present inventors have further surprisingly uncovered that following halogenations of the nanosized crosslinked polyamide polymers, such nanoparticles can inhibit both bacterial growth and withstand harsh conditions (e.g., high organic loads) while maintaining remarkable stability and durability to organic reagents and to repetitive bacterial loading cycles as compared with the common disinfectant.

The present inventors have further successfully utilized nanosized N-halamine-derivatized crosslinked polyamide nanoparticles for imparting anti-biofouling properties to various surfaces.

According to an aspect of some embodiments of the present invention there is provided a composition-of-matter comprising a plurality of crosslinked polymeric backbones, wherein at least 80% of the plurality of crosslinked polymeric backbones is characterized by an average hydrodynamic diameter of less than 500 nm, the crosslinked polymeric backbones being represented by the general Formula I:

wherein:

(a) $A_1$ is a monomeric unit derived from a secondary diamide compound, the secondary diamide compound being represented by the general formula II:

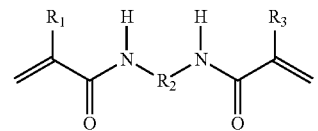

such that $R_1$ and $R_3$ are hydrogen or a methyl group; and $R_2$ is C1-C4 alkyl group;

(b) $A_2$ is a monomeric unit being a primary amide selected from the group consisting of: acrylamide, alkylacrylamide, and any derivative thereof;

(c) each of the plurality of polymeric backbones is cross-linked by at least one $A_1$;

(d) B, in each instance, is a halogen atom independently selected from the group consisting of Cl, Br, and I optionally being bound to the nitrogen belonging to $A_1$ and/or to $A_1$;

(e) x and y are integers, independently, representing the total numbers of $A_1$ and $A_2$, respectively, in the plurality of crosslinked polymeric backbones, the x and/or the y having a value of at least 5; and (f) n represents the total numbers of said B.

According to some embodiments, A2 is methacrylamide. According to some embodiments, $A_1$ is selected from the group consisting of: N,N-methylene bisacrylamide, N,N-ethylene bisacrylamide, and any derivative thereof. In some embodiments, $A_1$ is N,N-methylene bisacrylamide.

In some embodiments, B is Cl. In some embodiments, B is Br.

In some embodiments, n has a value such that n/(x+y) multiplied by 100 is at least 0.1.

According to some embodiments, the plurality of crosslinked polymeric backbones is characterized by an average hydrodynamic diameter of less than 50 nm with a size distribution of that varies within a range of less than 20%.

According to some embodiments, the plurality of crosslinked polymeric backbones is prepared by co-polymerizing a plurality of the monomeric units $A_1$ and $A_2$ in a weight ratio of $A_1$ to $A_2$ that ranges from about 1/9 to about 6/4 in a surfactant-free dispersion comprising at least one water soluble initiator, selected from the group consisting of: $AIBNCO_2H$, PPS, AIBN, and $H_2O_2$.

According to some embodiments, the plurality of crosslinked polymeric backbones is further subjected to a step of halogenation, the halogenation being chlorination and/or bromination, and/or iodination.

According to some embodiments, the composition-of-matter is in form of dry powder. In some embodiments, the composition-of-matter is incorporated within a formulation. In some embodiments, the composition-of-matter further comprises a substrate, wherein the plurality of crosslinked polymeric backbones is incorporated or coated in/on at least a portion of the substrate. In some embodiments, the substrate is or forms a part of an article. In some embodiments, substrate comprises or is made of a polymer, wood, a metal, glass, carbon, a biopolymer and/or silicon.

According to an aspect of some embodiments of the present invention, there is provided an article of comprising the composition-of-matter as described herein. In some embodiments, the article is selected from the group consisting of a medical device, organic waste processing device, fluidic device, water system device, tubing, an agricultural device, a package, a sealing article, a fuel container and a construction element.

According to an aspect of some embodiments of the present invention, there is provided method of inhibiting or reducing a formation of load of organic-based contaminant on or within an article, the method comprising incorporating or coating the composition-of-matter as described herein. In some embodiments, the article is selected from the group consisting of: a medical device, an organic waste processing device, a fluidic device, a water system device, an agricultural device, a package, a sealing article, a fuel container and a construction element. In some embodiments, the load of organic-based contaminant is maintained substantially reduced after at least one dehalogenation-rehalogenation cycle with the halogen atom.

According to some embodiments, the load of organic-based contaminant is a load of a microorganism, and/or a formation of a biofilm or biofouling in and/or on an article.

In some embodiments, the load of organic-based contaminant is maintained substantially reduced over a period of up to at least six months.

In some embodiments, the microorganism is selected from the group consisting of: viruses, fungi, parasites, yeast, bacteria, and protozoa. In some embodiments, the microorganism is a bacterium selected from the group consisting of: Gram positive bacteria, and Gram negative bacteria. In some embodiments, the microorganism is a bacterium selected from the group consisting of Gram negative bacteria.

According to some embodiments, the method further comprises one or more dehalogenating-rehalogenating cycles with halogen atoms selected from the group consisting of Cl, Br, and I.

According to an aspect of some embodiments of the present invention there is provided a process of preparing the composition-of-matter as described herein, the process comprising: co-polymerizing a plurality of the monomeric units $A_1$ and $A_2$, the co-polymerizing comprising dispersing said monomeric units in a weight ratio of $A_1/A_2$ that ranges from about 1/9 to about 6/4 in a surfactant-free aqueous phase comprising at one or more water soluble initiators, to thereby obtain a plurality of crosslinked polymeric backbones characterized by an average hydrodynamic diameter of less than 500 nm with a size distribution of that varies within a range of less than 20%.

In some embodiments, the one or more initiators are selected from the group consisting of: $AIBNCO_2H$, $H_2O_2$ PPS and AIBN. In some embodiments, the surfactant-free aqueous phase further comprising one or more reducing agent selected from the group consisting of: a sulfite, a bisulfite, thiosulfate, formamidinesulfinic acid, and ascorbic acid.

According to some embodiments, the surfactant-free aqueous phase is subjected to temperature that ranges from about 20° C. to about 100° C.

According to some embodiments, the process further comprises a step of at least partially halogenating the polymeric material. In some embodiments, the step of halogenating comprises the addition of a halide source. In some embodiments, the halide source is a salt of a material selected from the group consisting of: di-X-isocyanurate, hypo-halite, N—X-succinimide, or hypo-halite, wherein the halite and X each is selected from the group consisting of: Cl, I or Br. In some embodiments, the halide source is hypochlorite. In some embodiments, the halide source is dichlorocyanuric acid (DCCA).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3 is a graph showing the thermogravimetric analysis (TGA) of P(MAA-MBAA) nanoparticles before (solid line) and after (dotted line) chlorination of (MAA-MBAA)-Cl nanoparticles.

FIGS. 4A-B present cryogenic transmission electron microscopy (cryo-TEM) image (FIG. 4A; bar is 100 nm) and hydrodynamic size histogram (FIG. 4B) of the P(MAA-MBAA) nanoparticles.

FIG. 5 presents a graph showing the influence of the total monomer [MAA+MBAA] concentration on the diameter of the P(MAA-MBAA) nanoparticles. The P(MAA-MBAA) nanoparticles were prepared in the presence of different total monomer concentrations.

FIGS. 6A-B present point graphs showing the influence of the type and concentration of potassium persulfate (PPS) (FIG. 6A), and azobisisobutylonitrile (AIBN) (FIG. 6B) initiators, on the diameter of the P(MAA-MBAA) nanoparticles. The P(MAA-MBAA) nanoparticles were prepared in the presence of different concentrations of PPS or AIBN, as indicated herein below.

FIG. 7 presents a point graph showing the influence of the weight ratio [MBAA]/[MAA] on the size and size distribution of P(MAA-MBAA) nanoparticles prepared by holding the total monomer concentrations constant (2%) while varying the weight ratio [MBAA]/[MAA].

FIGS. 8A-B are point graphs showing the influence of the polymerization temperature on the diameter (FIG. 8A) and the yield of formation (FIG. 8B) of P(MAA-MBAA) nanoparticles prepared at different temperatures. The yield curve was constructed in triplicate with approximately 10% standard deviation (SD).

FIGS. 9A-B are point graphs demonstrating the kinetics (FIG. 9A) and yield (FIG. 9B) of the formation of the P(MAA-MBAA) nanoparticles prepared as described below. The yield curve displays data collected in triplicate with approximately 10% SD.

FIG. 10 presents a point graph showing the influence of the NaOCl concentration on the Cl loading content of the P(MAA-MBAA)-Cl nanoparticles as prepared.

(FIG. 36A) ESR spectrum of the DMPO-OH adducts formed upon mixing P(MAA-MBAA)-Cl NPs with either LB medium (black line) or Tryptone or yeast extract or NaCl. Quantification of ROS formed in response to mixing LB media or its various components with the chlorinated NPs (calculated from double integration of the DMPO-OH spin adducts quartet) (FIG. 36B).

(FIG. 38A). ESR spectrum of the DMPO adducts formed upon mixing LB medium with increasing concentrations of oxidative chlorine bound to P(MAA-MBAA)-Cl NPs (1.25-10 mM) (FIG. 38B). Quantification of ROS formed in response to increasing concentrations of the chlorinated NPs (calculated from double integration of the DMPO-OH spin adducts quartet) (FIG. 38C).

FIGS. 44 A-B present bar graphs showing the protein quantification of the chlorinated profiles versus the control, with the designation of "I" and "O" as in FIG. 43.

FIG. 46 present photos showing drippers containing the P(MAA-MBAA) NPs that were left untreated (i.e. control; upper panel) or treated with NaOCl (i.e. treated; middle panel). These drippers were stored in Hazerim for 2.5 months, following which the pictures shown were taken. Additionally, drippers that were regenerated with $Cl^+$ after one month of incubation in Hazerim, were put back into the experimental system and incubated for one month in Hazerim (lower panel).

FIG. 47A: BALB/c 3T3 and NR8383 cells were grown in the presence of medium that had been previously incubated with profiles impregnated with either P(MAA-MBAA) or P(MAA-MBAA)-Cl. After 24 h, the cells viability was determined using water soluble Tetrazolium assay (WST-1). FIG. 47B: BALB/c 3T3 cells were used and their viability was examined utilizing neutral red uptake (NRU) assay. FIG. 47C: adenosine triphosphate (ATP) measurements were performed. Control designates cells that were grown with medium that was not exposed to any profile.

DETAILED DESCRIPTION OF THE INVENTION

Figure 1:
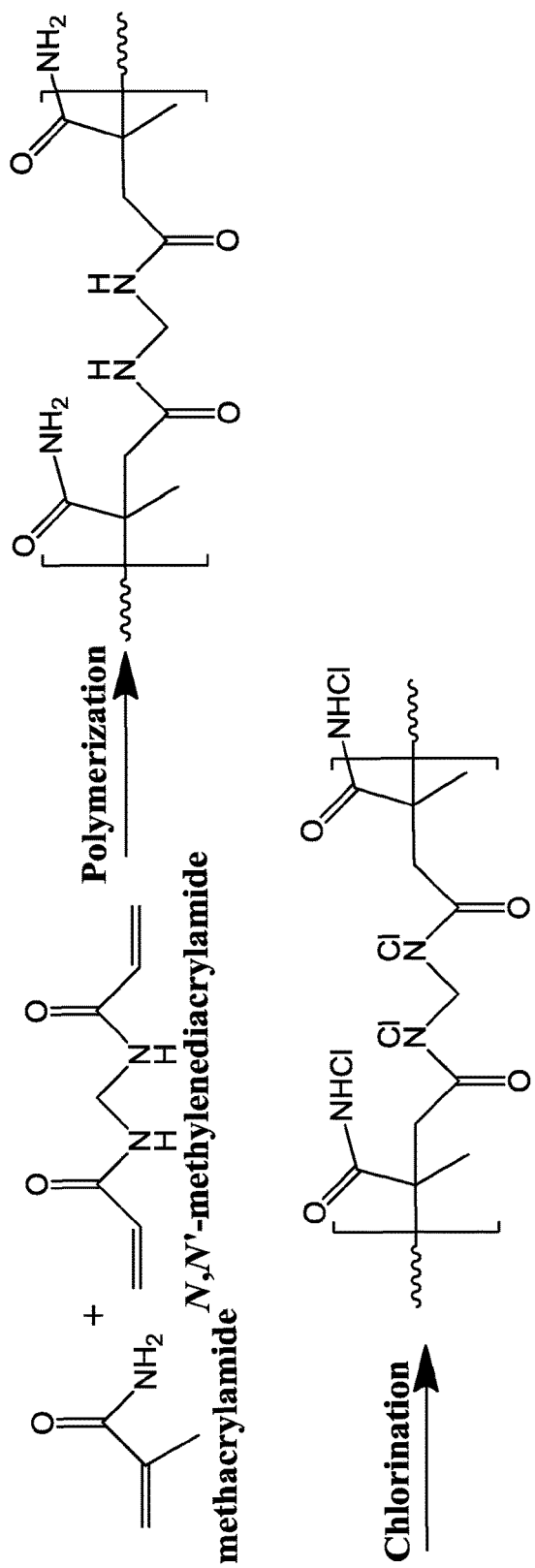
FIG. 1 is a schematic illustration of the methacrylamide (MAA) and N,N-methylene bisacrylamide (MBAA) chemical structures and the polymerization and the chlorination process.

The present invention, in some embodiments thereof, relates to nanosized crosslinked polymeric backbones, more particularly, but not exclusively, to nanosized N-halamine-derivatized crosslinked polyamide nanoparticles.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinathroughout, the present inventors have synthesized nanosized cross-linked N-halamine-derivatized polymer followed by a chlorination process. A beneficial antimicrobial/antibiofilm activity of the polymer was also demonstrated.

The present inventors have also shown that the chlorinated nanosized cross-linked N-halamine polymer exhibited improved and long-lasting antimicrobial and/or antibiofilm activities, compared to household bleach solution and compared to non-nanometeric polymer.

According to some embodiments, the polymer of the invention can be represented by the general formula I:

$([A_1]_x[A_2]_y)B_n$

Embodiments of the present invention therefore relate to nanosized crosslinked polymeric backbones comprising primary amide ($A_2$) and secondary diamide (A1) monomeric units, as described in details hereinbelow.

As used herein, the term "polymer" describes an organic substance composed of a plurality of repeating structural units (monomeric units) covalently connected to one another.

The Compositions-of-Matter:

According to an aspect of some embodiments of the present invention there is provided a composition-of-matter comprising a plurality of uniform nanosized crosslinked polymeric backbones.

By "uniform", it is meant that at least e.g., 30%, 40%, 50%, 60%, 70%, 80%, 90%, 99% of the plurality of the crosslinked polymeric backbones is characterized by a nanometric size having less than 15% variation in size.

The crosslinked polymeric backbone is represented by the general Formula I:

$([A_1]_x[A_2]_y)B_n$ wherein:

$A_1$ is a monomeric unit derived from a secondary diamide compound, and $A_2$ is a monomeric unit being a primary amide; x and y are integers, independently, representing the total numbers of $A_1$ and $A_2$, respectively; B, in each instance, is a halogen atom independently selected from the group consisting of Cl, Br, and I; and n represents the total numbers of said B. In some embodiments, x is an integer ranging from 1 to about 1,000,000, and y is an integer ranging from 1 to about 1,000,000.

Herein, the term "monomer" refers to a molecule that may bind chemically to other molecules to form a polymer.

The terms "monometric unit" refer to the repeat units, derived from the corresponding monomer. The polymer comprises the monomeric units. By "derived from" it is meant to refer to the compound following the polymerization process.

The term amide, has a common meaning in the art, and refers to a moiety of structure $C(O)NR_1R_2$, wherein $R_1$ and $R_2$ are independently hydrogen or a substituted or unsubstituted, cyclic or acyclic, linear or branched, saturated or unsaturated aliphatic, heteroaliphatic, aryl or heteroaryl moiety.

The term "secondary diamide" means a carboxamide-containing molecule having the two functional groups of —(CO)NHR.

In some embodiments, the secondary amide is derived from a secondary diamide compound, represented by the general formula II:

$$\underset{O}{\overset{R_1}{\underset{\|}{\text{C}}}}\!\!-\!\!\underset{R_2}{\overset{H}{\text{N}}}\!\!-\!\!\underset{R_2}{\text{N}}\!\!-\!\!\overset{H}{\underset{\|}{\text{N}}}\!\!-\!\!\underset{O}{\overset{R_3}{\underset{\|}{\text{C}}}}$$

such that $R_1$ and $R_3$ are hydrogen or a methyl group; and $R_2$ is C1-C4 alkyl group.

In some embodiments, $R_1$ is hydrogen and $R_3$ is a methyl group. In some embodiments, both $R_1$ and $R_3$ are methyl groups. In some embodiments, both $R_1$ and $R_3$ are hydrogens.

In some embodiments, $R_2$ is a methyl group. In some embodiments, $R_2$ is an ethyl group. In some embodiments, $R_2$ is a propyl group. In some $R_2$ is a butyl group.

As used herein, the group of methyl, ethyl, propyl and butyl, may also refer to any derivatives thereof. The term "derivative thereof" refers to a compound which retains the basic skeleton. As used herein and in the art, derivatives are compounds structurally similar to a parent compound and are derivable from that parent compound while being, in some embodiments, branched-chain of the parent compound. A derivative may or may not have different chemical or physical properties of the parent compound as long as the activity, e.g., antimicrobial activity is retained. Derivatization (i.e., modification) may involve substitution of one or more moieties within the molecule (e.g., a change in functional group) that do not substantially alter the function of the molecule for a desired purpose. The term "derivative" is also used to describe all solvates, for example hydrates or adducts (e.g., adducts with alcohols), active metabolites, and salts of the parent compound.

In some embodiments, $A_2$ is a monomer being a primary amide selected from the group consisting of: acrylamide, alkylacrylamide, and any derivative thereof. In exemplary embodiments, $A_2$ is methacrylamide (denoted as "MAA").

In some embodiments, $A_1$ is selected from the group consisting of: N,N-methylene bisacrylamide, N,N-ethylene bisacrylamide, any derivative thereof. In exemplary embodiments $A_1$ is N,N-methylene bisacrylamide (denoted as "MBAA").

In some embodiments, each of the plurality of polymeric backbones is crosslinked by at least one $A_1$.

As used herein, "polymer backbone" refers generally to a polymer comprising monomeric units. It is to be understood that in the context of the present invention, the term "polymeric backbone" refers to the main chain of polymeric skeleton together with chain branches projecting from the polymeric skeleton. The branches may comprise one or more of either $A_1$ and/or $A_2$ monomeric units as described herein.

The term "crosslinked polymer backbone" or, simply, "crosslinked polymer", refers generally to a polymer which comprises the monomeric units, including the crosslinking bridges.

As used hereinthroughout "P(MAA-MBAA)" denotes the crosslinked polymer comprising the monomeric units of MAA and MBAA. As used herein, "P(MAA-MBAA)-Cl" or "P(MAA-MBAA)-Br" stands for the P(MAA-MBAA) following a chlorination or bromination process, respectively.

As used herein, "crosslinked" and/or "crosslinking", and any grammatical derivative thereof refers generally to a chemical process or the corresponding product thereof in which two chains of polymeric molecules are attached by bridges (crosslinker) composed of an element, a group or a compound, which join certain carbon atoms of the chains by primary chemical.

Crosslinked polymers have quite different mechanical and physical properties than their uncrosslinked linear or branched counterparts. For example, crosslinked polymers may show unique and highly desirable properties such as solvent resistance, high cohesive strength, and elastomeric character. Typically, the crosslinked polymers are characterized by a plurality of polymeric strands that may be covalently linked together. The term "polymeric strand" refers to any composition of monomeric units covalently bound to define a backbone.

Typically, but not exclusively, the crosslinking reaction can occur in situ during formation of the polymer.

In the context of the present disclosure the cross linker is a compound having at least two double carbon-carbon bonds. In some embodiments the cross linker is secondary diamide. In exemplary embodiments, the cross linker comprises at least one $A_1$. In some embodiment, the cross linker further comprises at least one $A_2$.

In formula I as noted herein above B is haloatom.

As used in the art, the term "halo", "halo atom" or "halogen" refers to an atom selected from the group consisting of: chlorine, bromine, and iodine and fluorine.

In some embodiments, one or more hydrogens bound to a nitrogen atom in the crosslinked polymeric are substituted (also termed herein throughout: "halogenated") in each instance, by a halo atom.

In some embodiments, the halogen atom independently selected from the group consisting of Cl, Br, I and F. In some embodiments, the halogen atom is Br. In some embodiments, the halogen atom is Cl. In some embodiments, the halogen atom is F. In some embodiments, the halogen atom is I. In some embodiments, the crosslinked polymer is attached to both Cl and Br atoms. In some embodiments, the crosslinked polymer is attached to both Cl and I atoms. In some embodiments, the crosslinked polymer is attached to both Br and I atoms.

In some embodiments, at least one halo atom is bound (also termed hereinthroughout as "attached") to a nitrogen atom belonging to the secondary diamide monomeric unit, as described herein. In some embodiments, at least one halo atoms is bound to the nitrogen atom belonging to a primary amide monomeric unit, as described herein.

The total number of the secondary diamide monomers and crosslinker within the crosslinked polymeric backbone is defined herein as "x"; the number of the primary amide monomer within the crosslinked polymeric backbone is herein defined as "y".

The number of the halo atom attached to the crosslinked polymeric backbone is defined as n.

It would be appreciated that x, and y can be controlled as desired by selecting the mol ratio of the respective monomeric units used for forming the crosslinked polymeric backbone, as discussed hereinbelow.

In some embodiments, the sum of x+y, representing the total numbers of $A_1$ and $A_2$, respectively, in a crosslinked polymeric backbone, has a value of at least e.g., 1, 5, 10, 15, 20, 25, 30, 35, 40, 45, 50, 55, 60, 75, 80, 85, 90, 95, 100, including any value therebetween. In some embodiments, x has a value of at least e.g., 1, 5, 10, 15, 20, 25, 30, 35, 40, 45, 50, 55, 60, 75, 80, 85, 90, 95, 100, including any value therebetween. In some embodiments, y has a value of at least e.g., 1, 5, 10, 15, 20, 25, 30, 35, 40, 45, 50, 55, 60, 75, 80, 85, 90, 95, 100, including any value therebetween.

It would be further appreciated that n can be controlled as desired by selecting the halogenation parameters as discussed hereinbelow under "The Process".

For example n/(x+y) multiplied by 100 may be o, meaning that no halo atom is attached to the crosslinked polymeric backbone.

In some embodiments, n/(x+y) multiplied by 100 maybe e.g. at least e.g.: 1, 2, 3, 4, 5, 6, 7, 8, 9, 10, 11, 12, 13, 14, 15, 16, 17, 18, 19, 20, 30, 40, 50, 60, 70, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, including any value therebetween.

Hereinthroughout, the terms "nanoparticle", "nano", "nanosized", and any grammatical derivative thereof, which are used herein interchangeably, describe a particle featuring a size of at least one dimension thereof (e.g., diameter, length) that ranges from about 1 nanometer to 1000 nanometers. Hereinthroughout NP(s) designates nanoparticle(s).

In some embodiments, the size of the particles described herein represents an average size of a plurality of nanoparticle composites or nanoparticles.

In some embodiments, the average size of at least e.g., 10%, 20%, 30%, 40%, 50%, 60%, 70%, 80%, 90%, 95% of the cross-linked polymers, including any value therebetween, ranges from: about 1 nanometer to 1000 nanometers, or, in other embodiments from 1 nm to 500 nm, or, in other embodiments, from 10 nm to 200 nm. In some embodiments, the average size ranges from about 1 nanometer to about 300 nanometers. In some embodiments, the average size ranges from about 1 nanometer to about 200 nanometers. In some embodiments, the average size ranges from about 1 nanometer to about 100 nanometers. In some embodiments, the average size ranges from about 1 nanometer to 50 nanometers, and in some embodiments, it is lower than 35 nm.

In some embodiments, a plurality of crosslinked polymeric backbones is characterized by an average hydrodynamic diameter of less than 50 nm with a size distribution of that varies within a range of less than e.g., 60%, 50%, 40,%, 30%, 20%, 10%, including any value therebetween.

In some embodiments, plurality of crosslinked polymeric backbones are characterized by an average hydrodynamic diameter of less than 30 nm with a size distribution of that varies within a range of less than e.g., 60%, 50%, 40,%, 30%, 20%, 10%, including any value therebetween.

In some embodiments, the average size of the crosslinked polymer is about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 40 nm, about 42 nm, about 44 nm, about 46 nm, about 48 nm, or 50 nm, including any value therebetween.

As used herein the term average size refers to diameter of the crosslinked polymer. The term "diameter" is art-recognized and is used herein to refer to either of the physical diameter (also termed "dry diameter") or the hydrodynamic diameter. As used herein, the "hydrodynamic diameter" refers to a size determination for the crosslinked polymer in solution (e.g., aqueous solution) using any technique known in the art, e.g., dynamic light scattering (DLS).

As exemplified in the Example section that follows, the dry diameter of the crosslinked polymer, as prepared according to some embodiments of the invention, may be evaluated using cryo-transmission electron microscopy (TEM) imaging. In exemplary embodiments, the dry diameter of the crosslinked polymer, as prepared according to some embodiments of the invention, is about 5 nm, and the hydrodynamic diameter, as evaluated by DLS is about 27 nm.

The crosslinked polymeric particle(s) can be generally shaped as a sphere, a rod, a cylinder, a ribbon, a sponge, and any other shape, or can be in a form of a cluster of any of these shapes, or can comprises a mixture of one or more shapes.

In some embodiments, the composition-of-matter comprises a plurality of crosslinked polymeric particles, and at least 10%, 20%, 30%, 40%, 50%, 60%, 70%, 80%, 90%, 95%, 98%, 99%, 99.9%, or all of the crosslinked polymeric particle are nanosized as described herein, e.g., in shape and average size.

In some embodiments, the plurality of crosslinked polymeric particles is in a form of a dry powder. As used herein, "dry powder" refers to a powdered particle that is a finely dispersed solid i.e., not suspended or dissolved in a propellant, or other liquid.

Any one of the compositions-of-matter described herein, and any embodiments thereof, including exemplary compositions-of-matter as described herein, can be prepared by any method known if the art for obtaining the crosslinked polymeric particles, including the method as described herein. In some embodiments, the composition-of-matter is prepared by co-polymerizing a plurality of monomers $A_1$ and $A_2$ as defined hereinabove. In exemplary embodiments, $A_1$ is N,N-methylene bisacrylamide and $A_2$ is methacrylamide.

In some embodiments, the an initial weight ratio of $A_1$ to $A_2$ of about e.g., 1:9, 2:9, 1:4, 1:3, 1:2, 1:1, 6:5, 6:4, including any value therebetween is used for said polymerization.

In exemplary embodiments, the polymerization is performed in a surfactant-free dispersion. In some embodiments the dispersion further comprises at least one water soluble initiator. Exemplary water soluble initiators include, but are not limited to, AIBNCO$_2$H, PPS, H$_2$O$_2$, as further described and defined hereinbelow, under "The Process".

In some embodiments, the plurality of crosslinked polymeric backbones is further subjected to a step of halogenations. As used herein "halogenations" refers to chlorination, bromination, or iodination, or combination thereof, as further described herein below, under "The Process". Further embodiments of the composition-of matter are described hereinbelow.

Substrates and/or Articles:

According to some of any of the embodiments described herein, a composition according to any one of the respective embodiments, further comprises a substrate. In some embodiments a plurality of halogenated or non-halogenated crosslinked polymeric backbones as described in any of the respective embodiments is incorporated in and/or on at least a portion of the substrate. Herein, "halogenated crosslinked polymeric backbones" also refer to crosslinked polymeric backbones capable of being rechargeable with halo atoms, as described hereinbelow.

According to an aspect of some embodiments of the present invention, there is provided a substrate having incorporated in and/or on at least a portion thereof, crosslinked polymeric backbones as described herein.

According to an aspect of some embodiments of the present invention there is provided a substrate having incorporated in and/or on at least a portion thereof a halogenated crosslinked polymeric backbones as described herein in any of the respective embodiments.

By "a portion thereof" it is meant, for example, a surface or a portion thereof, and/or a body or a portion thereof, of solid or semi-solid substrates; or a volume or a part thereof, of liquid, gel, foams and other non-solid substrates.

Substrates of widely different chemical nature can be successfully utilized for incorporating (e.g., depositing on a surface thereof) crosslinked polymeric backbones thereon, as described herein. By "successfully utilized" it is meant that (i) the halogenated crosslinked polymeric backbones successfully form a uniform and homogenously coating on the substrate's surface; and (ii) the resulting coating imparts long-lasting desired properties (e.g., antimicrobial properties) to the substrate's surface.

Substrate usable according to some embodiments of the present invention can therefore be hard (rigid) or soft, solid, semi-solid, or liquid substrates, and may take a form of a foam, a solution, an emulsion, a lotion, a gel, a cream or any mixture thereof.

Substrate usable according to some embodiments of the present invention can have, for example, organic or inorganic surfaces, including, but not limited to, glass surfaces; porcelain surfaces; ceramic surfaces; silicon or organosilicon surfaces, metallic surfaces (e.g., stainless steel); mica, polymeric surfaces such as, for example, plastic surfaces, rubbery surfaces, paper, wood, polymer, a metal, carbon, a biopolymer, silicon mineral (rock or glass), surfaces, wool, silk, cotton, hemp, leather, fur, feather, skin, hide, pelt or pelage) surfaces, plastic surfaces and surfaces comprising or made of polymers such as but not limited to polypropylene (PP), polycarbonate (PC), polyethylene (PET), high-density polyethylene (HDPE), low-density polyethylene (LDPE), polyester (PE), unplasticized polyvinyl chloride (PVC), and fluoropolymers including but not limited to polytetrafluoroethylene (PTFE, Teflon®); or can comprise or be made of any of the foregoing substances, or any mixture thereof.

Alternatively, other portions, or the entire substrate are made of the above-mentioned materials.

In some embodiments, the substrate incorporating the crosslinked polymer as described herein is or forms a part of an article.

Hence according to an aspect of some embodiments of the present invention there is provided an article (e.g., an article-of-manufacturing) comprising a substrate incorporating in and/or on at least a portion thereof a composition-of-matter or the crosslinked polymer, as described in any one of the respective embodiments herein.

The article can be any article which can benefit from the antimicrobial and/or anti-biofilm formation activities of the halogenated crosslinked polymeric backbones.

Exemplary articles include, but are not limited to, medical devices, organic waste processing device, fluidic device, an agricultural device, a package, a sealing article, a fuel container, a water and cooling system device and a construction element.

Non-limiting examples of devices which can incorporate the halogenated crosslinked polymer, as described herein, beneficially, include tubing, pumps, drain or waste pipes, screw plates, and the like.

In some embodiments, the article is an element used in water treatment systems (such as for containing and/or transporting and/or treating aqueous media or water), devices, containers, filters, tubes, solutions and gases and the likes.

In some embodiments, the article is an element in organic waste treatment systems (such as for containing and/or disposing and/or transporting and/or treating organic waste), devices, containers, filters, tubes, solutions and gases and the likes.

Contaminant Treating Applications:

While studying the activity of the compositions of matter as described hereinabove, and the activity of compositions-of-matter in which crosslinked polymers are deposited on a substrate's surface, as described herein, the present inventors have surprisingly uncovered that such compositions of matter exhibit high and long lasting antifouling activity and can therefore be beneficially incorporated in articles of in which such an activity is desired. By "long lasting antifouling activity" it is meant to refer to the ability of the compositions-of-matter as described hereinthroughout to withstand repetitive loading cycle of organic based material (e.g., bacteria). Additionally, or alternatively, it is meant to refer to the ability of the compositions-of-matter as described hereinthroughout to maintain its activity against organic based contaminant, within less than 30% variation, up to a period of at least six months.

Because wastewater and sludge treatment generally include primary and secondary treatment, which may only remove a fraction of the pathogenic microorganisms, discharge of treated wastewater and sludge represent a potential source of microbial contamination, and, in this respects, the compositions-of-matter as described hereinthroughout, is of particular beneficial.

The present process is effective for treating one or more contaminant components, e.g., organic-based components, such as hydrocarbons, and/or organic-based components. Organic-based contaminant components which may be treated in the present process can include organic sulfur, in particular, non-thiophenic sulfur. Examples of organic-based and hydrocarbon-based contaminant components which may be processed in accordance with the present invention include, but are not limited to, petroleums (crude oils including topped crude oils), organic acids such as benzoic acid, ketones, aldehydes, aromatic components including phenols and the like, organic materials containing hetero atoms such as nitrogen, sulfur and halogen, e.g., chloride, and the like, dyes, polymeric materials, including, without limitation polymericcarbohydrate (e.g., polysaccharides), proteins, fatty acids and mixtures thereof. Other contaminants which may be treated in the present process include, for example, and without limitation, materials which are active components in or products of a manufacturing process, such as cyanide or hydrazine, or a process by-product, organic insecticides, herbicides, sewage contamination, and pesticides resulting from soil leaching due to continuous water usage in agriculture, e.g., the production of fruits and vegetables particularly in arid to semi-arid climates.

In one embodiment of the invention, the process comprises contacting the contaminant component or components with at least one of the halogenated crosslinked polymers as described hereinabove so as to provide chemical modification of contaminant component or components to provide less environmentally deleterious or more environmentally acceptable aqueous-based materials, preferably in high yields. It is noteworthy that the composition-of-matter and/or the articles as described hereinabove are used at a concentration which does not provide substantial adverse environmental effects.

The term "chemical modification" as used herein refers to a change in the contaminant component or components which change results from the chemical conversion, e.g., chemical reaction, oxidation and/or degradation and/or alteration of at least one environmentally adverse property, of one or more of such contaminant components. Also, the chemical modification may occur with regard to the carbon and/or hydrogen portions of the organic-containing contaminant components and/or to the other portions, e.g., such as contained sulfur, nitrogen, phosphate, oxygen, halide, metals or the like, of such organic-containing contaminant components.

In addition, such modification can reduce one or more of the environmentally objectional characteristics of such contaminant component or components to yield aqueous-based materials, including process water streams and ground water streams having, for example, a reduced level of such contaminated component or components.

In some embodiments the composition-of-matter and/or the articles as described hereinthroughout are utilized for self-cleaning coatings. As used herein, the term "self-cleaning" means the property of a surface that generally keeps the surface clean without mechanical force or detergent to loosen and remove visual detractants.

According to some embodiments of the present invention, the composition-of-matter as described hereinthroughout is incorporated within a formulation. In some embodiments, the formulation is used as an antibacterial and/or antifungal cleaner.

Antimicrobial Anti-Biofilm Formation Applications:

According to another aspect of some embodiments of the present invention there is provided a method of inhibiting or reducing or retarding the formation of load of a microorganism and/or the formation of a biofilm, in and/or on an article. The method comprises incorporating in and/or on the article any one of the compositions-of-matter as described herein, including any of the respective embodiments thereof.

As further exemplified in the Examples section that follows, the chlorinated NPs and the articles comprising the same exhibit high capability to withstand repetitive cycles of bacterial exposure. The article can be any one of the articles described herein.

Such articles, therefore, take advantage of the improved antimicrobial activity exhibited by the halogenated cross-linked polymer as described herein.

Herein "antimicrobial activity" is referred to as an ability to inhibit (prevent), reduce or retard bacterial growth, fungal growth, biofilm formation or eradicate living bacterial cells, or their spores, or fungal cells or viruses in a suspension, on a surface or in a moist environment.

Herein, inhibiting or reducing or retarding the formation of load of a microorganism refers to inhibiting reducing or retarding growth of microorganisms and/or eradicating a portion or all of an existing population of microorganisms.

Thus, the halogenated crosslinked polymer as described herein can be used both in reducing the formation of microorganisms on or in an article, and in killing microorganisms in or on an article or a living tissue.

The microorganism can be, for example, a unicellular microorganism (prokaryotes, archaea, bacteria, eukaryotes, protists, fungi, algae, euglena, protozoan, dinoflagellates, apicomplexa, trypanosomes, amoebae and the likes), or a multicellular microorganism. As used herein, the terms "bacteria", or "bacterial cells" may refer to either Gram-positive bacteria (e.g., S. aureus) and/or Gram-negative bacteria (e.g., E. coli) and archae, including multi-drug resistant (MDR) bacteria.

In some embodiments of the present invention the composition-of-matter in any embodiment as described hereinthroughout, may be characterized by high affinity to a specified bacteria type, species, or genus. Therefore, in some embodiments of the present invention the composition-of-matter in any embodiment as described hereinthroughout, the composition-of-matter may be used an effective way for selectively targeting bacteria Herein "anti-biofouling activity" or "antifouling activity" is referred to as an ability to inhibit (prevent), reduce or retard biofilm formation on a substrate's surface.

The term "biofilm", as used herein, refers to an aggregate of living cells which are stuck to each other and/or immobilized onto a surface as colonies. The cells are frequently embedded within a self-secreted matrix of extracellular polymeric substance (EPS), also referred to as "slime", which is a polymeric sticky mixture of nucleic acids, proteins and polysaccharides.

In the context of the present embodiments, the living cells forming a biofilm can be cells of a unicellular microorganism (prokaryotes, archaea, bacteria, eukaryotes, protists, fungi, algae, euglena, protozoan, dinoflagellates, apicomplexa, trypanosomes, amoebae and the likes), or cells of multicellular organisms in which case the biofilm can be regarded as a colony of cells (like in the case of the unicellular organisms) or as a lower form of a tissue.

In the context of the present embodiments, the cells are of microorganism origins, and the biofilm is a biofilm of microorganisms, such as bacteria and fungi. The cells of a microorganism growing in a biofilm are physiologically distinct from cells in the "planktonic form" of the same organism, which by contrast, are single-cells that may float or swim in a liquid medium. Biofilms can go through several life-cycle steps which include initial attachment, irreversible attachment, one or more maturation stages, and dispersion. The phrases "anti-biofilm formation activity" refers to the capacity of a substance to effect the prevention of formation of a biofilm of bacterial, fungal and/or other cells; and/or to effect a reduction in the rate of buildup of a biofilm of bacterial, fungal and/or other cells, on a surface of a substrate. In some embodiments, the biofilm is formed of bacterial cells (or from a bacterium).

In some embodiments, a biofilm is formed of bacterial cells of bacteria selected from the group consisting of all Gram-positive and Gram-negative bacteria and archae As demonstrated herein, a composition of matter as described herein has shown to exhibit anti-biofilm formation (ABF) activity and can thus prevent, retard or reduce the formation of a mass of a biofilm.

In some embodiments of the present invention, the activity of preventing or reducing the formation of a biofilm, may be achieved by a substrate or an article incorporating the halogenated crosslinked polymer, as described herein.

The inhibition or reduction or retardation of formation of a biofilm assumes that the biofilm has not yet been formed, and hence the presence of the halogenated crosslinked polymer nanoparticles are required also in cases where no biofilm is present or detected.

As used herein, the term "preventing" in the context of the formation of a biofilm, indicates that the formation of a biofilm is essentially nullified or is reduced by at least 20%, at least 30%, at least 40%, at least 50%, at least 60%, at least 70%, at least 80%, at least 90%, including any value therebetween, of the appearance of the biofilm in a comparable situation lacking the presence of the halogenated crosslinked polymer or a composition of matter containing same. Alternatively, preventing means a reduction to at least 15%, 10% or 5% of the appearance of the biofilm in a comparable situation, lacking the presence of the halogenated crosslinked polymer or a composition-of-matter or an article containing same. Methods for determining a level of appearance of a biofilm are known in the art.

As used herein, the term "preventing" in the context of antimicrobial, indicates that the growth rate of the microorganism cells is essentially nullified or is reduced by at least 20%, at least 30%, at least 40%, at least 50%, at least 60%, at least 70%, at least 80%, at least 90%, including any value therebetween, of the appearance of the microorganism in a comparable situation lacking the presence of the halogenated crosslinked polymer or a composition of matter containing same. Alternatively, preventing means a reduction to at least 15%, 10% or 5% of the appearance of the microorganism cells in a comparable situation lacking the presence of the halogenated crosslinked polymer or a composition of matter containing same. Methods for determining a level of appearance of a microorganism cells are known in the art.

In some embodiments there is provided an article which comprises the composition of matter incorporated in and/or on a substrate.

Compositions of matter as described herein can be incorporated within any of the articles of manufacturing, during manufacture of any of the article described herein.

The substrates presented herein can be used to modify any industrial or clinical surface to prevent bacterial colonization and biofilm formation.

The Process:

The present inventors have designed and successfully practiced novel processes for preparing a uniform crosslinked polymamide nanoparticles as described hereinabove. It is to note that synthesizing such a controlled size of the polymer is subjected to various limitations, imposed by a e.g., different tendency of the monomers to disperse in the solution, complicated desired structural features that are required for optimal size, uniformity, and performance of the crosslinked polymer, incompatibility of the reactants, initiators and the like. Hence, devising a process that overcomes these limitations and is designed to obtain a uniform crosslinked polyamide nanoparticles that exhibits at least a reasonable performance is highly advantageous.

Hence, according to another aspect of embodiments of the invention there is provided a process of synthesizing the composition-of-matter described herein, the process comprising: co-polymerizing a plurality of said monomers $A_1$ and $A_2$, the co-polymerizing comprising dispersing said monomers in a weight ratio of $A_1/A_2$ that ranges from about 1:9 to about 6:4 in a surfactant-free aqueous phase comprising an initiator, to thereby obtain a polymeric material characterized by an average hydrodynamic diameter of at least one dimension thereof of less than 500 nm with a size distribution that varies within a range of less than 20%.

The polymerization of various monomeric units can be effected by any polymerization method known in the art, e.g., using suitable polymerization initiators and optionally chain transfer agents. Such suitable polymerization initiators and chain transfer agents can be readily identified by a person skilled in the art.

As demonstrated in the Examples section that follows, the polymerization can be performed via a radical polymerization methodology in an aqueous solution.

The term "radical polymerization" or "free radical polymerization" refers to a method of polymerization by which a polymer is formed from the successive addition of free radical building blocks. Free radicals can be formed via a number of different mechanisms usually involving separate initiator molecules. Since the radical polymerization initiator can generate a radical by abstracting hydrogen from a carbon-hydrogen bond, when it is used in combination with an organic material such as a polyolefin a chemical bond can be formed. Following creation of free radical monomeric units, polymer chains grow rapidly with successive addition of building blocks onto free radical sites.

As a radical polymerization initiator for initiated polymerization or redox initiated polymerization, the following exemplary water soluble radical polymerization initiators may be used, without being limited thereto, singly or in a combination of two or more types: peroxides such as ammonium persulfate, potassium persulfate, sodium persulfate, hydrogen peroxide, benzoyl peroxide, cumene hydroperoxide, or di-t-butyl peroxide; a redox initiator that is a combination of the above-mentioned peroxide and a reducing agent such as a sulfite, a bisulfite, thiosulfate, formamidinesulfinic acid, or ascorbic acid; or an azo-based radical polymerization initiator, such as, without limitation, 2,2'-azobis(2-amidinopropane) (AIBN), AIBNCOOH, and 2,2'-azobis(2-amidinopropane), and potassium persulfate (PPS). In exemplary embodiments, the initiator is selected from the group consisting of: PPS and AIBN.

As described hereinabove, it is to be understood that a polymerization process utilizing monomer having a functional group that can form a crosslinked structure.

From the viewpoint of ease of incorporation of the crosslinked structure as described hereinabove under "The Compositions-of-matter", the method in which a polymerization reaction is carried out using in combination a crosslinking agent (monomer) having at least two polymerizable double carbon-carbon bonds. Similar crosslinking reaction may be caused by heating at the same time as radical polymerization.

It is to be understood that other radical polymerization methodology can be applied, such as, without limitation, living radical polymerization.

By "living polymerization" it is meant to refer to a form of chain growth polymerization where the ability of a growing polymer chain to terminate has been removed. Living radical polymerization is a type of living polymerization where the active polymer chain end is a free radical.

Several methodologies of living radical polymerization are known in the art and are conceivable to be applied in the context of the present invention, including, without limitation, reversible-deactivation polymerization, catalytic chain transfer, cobalt mediated radical polymerization, iniferter polymerization, stable free radical mediated polymerization, atom transfer radical polymerization, reversible addition fragmentation chain transfer (RAFT) polymerization, iodine-transfer polymerization (ITP), selenium-centered radical-mediated polymerization, telluride-mediated polymerization (TERP), and stibine-mediated polymerization.

As described hereinthroughout, in some of any of the embodiments, the polymerization process is affected in an aqueous solution comprising the mixture of monomeric units $A_2$ and $A_1$ as defined herein above, under "The Composition of Matter" and an initiator.

In exemplary embodiments, the monomeric units (or monomers) are MAA and MBAA. In some embodiments the ratio between $A_2$ and $A_1$ prior to the polymerization thereof is e.g., 1:1, 1:2, 1:3:1:4, 1:5, 1:6, 1:7, 1:8, 1:9, 1:10, 2:1, 3:1, 4:1, 5:1, 6:1, 7:1, 8:1, 9:1, 10:1, including any value therebetween. As described in the Examples section that follows, the nanoparticle size of the crosslinked polymer is affected by the initial weight ratio of $A_1$ and $A_2$ in the solution.

In exemplary embodiments, the steady ratio of MAA and MBAA are 55% MAA:45% MBAA. In exemplary embodiments, the total concentration (% w/v) of the monomers in the solution is e.g., 1%, 2%, 3%, 4%, 5%, including any value therebetween. As exemplified in the Examples section that follows, the hydrodynamic diameter of the formed P(MAA-MBAA) is increased with increasing the total concentration of the monomers.

As described in the Example section that follows, the initiator type (e.g., PPS and AIBN) and the concentration thereof may affect on the hydrodynamic size and size distribution of the formed crosslinked polymeric nanoparticles.

In exemplary embodiments, the concentration of the initiator, e.g., PPS, or AIBN, is e.g., 1%, 2%, 3%, 4%, 5%, 6%, 7%, 8%, 9%, 10%, including any value therebetween.

In some embodiments, the size and the polymerization yield of the crosslinked polymer is affected by the temperature. In some embodiments the mixture or solution is maintained at a temperature that ranges from 10° C. to 100° C., during the polymerization procedure. In some embodiments the mixture or solution is maintained at temperature that ranges from 40° C. to 90° C., or from 45° C. to 95° C., or from 60° C. to 100° C.

In exemplary embodiments the mixture or solution is maintained at about 90° C.

In some embodiments the size and the diameter of the crosslinked polymer is affected by duration (time) of polymerization process.

In some embodiments, the duration of polymerization process is at least 1 minute. In some embodiments, the duration of polymerization process is at least 30 seconds, at least 1 minute, at least 2 minutes, at least 3 minutes, at least 5 minutes, at least 10 minutes, at least 15 minutes, at least 20 minutes, at least 25 minutes, at least 30 minutes, at least 35 minutes, at least 40 minutes, at least 45 minutes, or at least 50 minutes. In exemplary embodiments, the duration of polymerization process is at least 1 minute, e.g., 1 min, 5 minutes or 30 minutes. Each possibility represents a separate embodiment of the invention.

In some embodiments, the crosslinked polymer as described hereinthroughout is at least partially halogenated. By "at least partially halogenated" it is meant that at least 1%, 2%, 5%, 10%, 15%, 20%, 30%, 40%, 50%, 60%, 70%, 80%, 90%, 99%, of the hydrogens bound to a nitrogen atom in the crosslinked polymeric are substituted by halogen atom, as defined and described hereinabove, under "The Composition-of-matter".

The halogenations process may be carried out during the polymerization process or after the polymerization process, i.e. on the crosslinked polymers.

In exemplary embodiments, the halogenation (e.g., chlorination) process is applied on the P(MAA-MBAA) particles (i.e. after the polymeric process) of 20-50 nm, 25-35 nm, or about 27 nm diameter, as detailed in the Examples section that follows.

In some embodiments, the halogenation is applied by addition of a halide source to a solution comprising the crosslinked polymers, selected from, but not limited to, one or more salts of a material selected from the group consisting of: di-X-isocyanurate, hypo-halite, N—X-succinimide, or hypo-halite, wherein said halite and X each are selected from the group consisting of: Cl, I or Br. In some embodiments, the salt is selected from sodium or calcium salts. In exemplary embodiments the halogenation is chlorination being performed using one or more chlorine source reagents selected from, for example and without limitation, hypochlorite (NaOCl), and dichlorocyanuric acid (DCCA).

In some embodiments, the halogenation is affected by the concentration (% w/v) of the halide source. By "halogenation is affected" it is meant to refer to the percent of the hydrogen atoms bound to a nitrogen atom in the crosslinked polymer being substituted by the halogen atom.

In some embodiments, the concentration of the halide source is e.g., 0.001%, 0.005%, 0.01%, 0.05, 0.1%, 0.5%, 1%, 1.5%, 2%, 2.5%, 3%, 3.5%, 4%, 5%, 10%, 20%, including any value therebetween, of a solution comprising the crosslinked polymer.

In some embodiments, the halogenation is affected by the halogination time. In exemplary embodiments, as further described in the Examples section that follows, the halogination time ranges e.g., from about 1 minute to about 150 minutes, from about 10 minutes to about 100 minutes, from about 20 minutes to about 90 minutes, from about 30 minutes to about 80 minutes, or from about 40 minutes to about 60 minutes.

In some embodiments, the halogenation is affected by the halogenation temperature. In exemplary embodiments, as further described in the Examples section that follows, the halogenations process was carried out at temperature that ranges from 30° C. to 80° C., following the polymerization procedure. In some embodiments the halogenation is carried out at temperature that ranges from 20° C. to 100° C., or from 45° C. to 75° C., or from 50° C. to 70° C.

In some embodiments, the halogenated crosslinked polymer may be dehalogeneted. By "dehalogeneted", or any grammatical derivative thereof, it is meant that the % of the halogen atom in the crosslinked polymer is reduced. Dehalogenation may be spontaneous over time, upon contact with organic-based material, e.g., bacteria, or initiated by exposure to U.V. radiation.

As exemplified in the Examples section that follows, at least e.g. 85%, and even 95% of the halogen atom in the crosslinked polymer are maintained (i.e. remains not dehalogenated) over a time of at least one month, 2 months, 3 months, 4 months, 5 months, 6 months, 7 months, 8 months, 9 months, 10 months, 11 months, 12 months, 13 months, 14 months, 15 months.

In some embodiments, the "dehalogeneted" atoms may be rechargeable, i.e. rehalogenated, by using any halide source as described hereinabove.

In some embodiments, several cycles (also termed herein "loading cycle") e.g., at least 1, 2, 3, 4, 5, 6, 7, 8, 9, 10, 15, 20, 25, 30, 35, 40, 50, 60, 70, of dehalogenetion-rehalogenation may be applied on the composition-of mater or article as described hereinthroughout.

General

It is expected that during the life of a patent maturing from this application many relevant nanosized crosslinked polyamide will be developed and the scope of the term crosslinked polyamide is intended to include all such new technologies a priori.

As used herein the term "about" refers to ±10%.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Material and Methods

Materials

All chemicals were of analytical-grade and used with no further purification.

MAA, MBAA sodium hypochlorite (4%), potassium persulfate (PPS) dichlorocyanuric acid (DCCA) and 2,20-Azobisisobutyronitrile (AIBN) were purchased from Sigma Aldrich (Rehovot, Israel); sodium iodide was purchased from Strem Chemicals (Newburyport, Mass., USA); acetic acid was purchased from Fisher Scientific (Loughborough, UK); sodiumthiosulfate (0.01 N) was purchased from Acros Organics (Geel, Belgium); and water was purified by passing deionized water through an Elgastat Spectrum reverse osmosis system (Elga LTD, High Wycombe, UK).

Instruments

Attenuated total reflectance (ATR) analysis was performed with Bruker Platinum ATR QuickSnap™ sampling modules A220/D-01. The samples were analyzed over 100 scans at a 4 $cm^{-1}$ resolution. The hydrodynamic diameter and size distribution of the particles dispersed in water were measured at room temperature with a particle analyzer, model NANOPHOX (Sympatec GmbH, Germany). The size and size distribution of the dried particles were measured with a cryogenic transmission electron microscope (cryo-TEM). For this purpose, a small droplet of an aqueous dispersion of the nanoparticles was placed on a perforated carbon film supported on a TEM copper grid held by tweezers. The drop was blotted with a piece of filter paper, resulting in the formation of thin films of 100 to 300 nm thickness within the micropores of the carbon-coated lace-like polymer layer supported on the grid. The specimen was subsequently plunged into a reservoir of liquid ethane cooled by liquid nitrogen to ensure its vitrification (rapid freezing) and to prevent ice crystal formation. The vitrified specimen was transferred under liquid nitrogen and mounted on a cryogenic sample holder cooled to −170° C. All samples were observed under low-dose conditions. Vitrified samples were examined in an FEI T12 G2 Cryo-TEM operating at 120 kV and equipped with an Oxford CT-3500 cryo-holder system. Images were recorded with a Gatan US1000 high-resolution cooled CCD camera and processed with DigitalMicrograph version 3.3.1 software. The ramp-shaped optical density gradients in the background were digitally corrected. The thermal behavior of the P(MAA-MBAA) and P(MAA-MBAA)-Cl nanoparticles was measured by thermogravimetric analysis (TGA) (TGA/DSC 1 STAR$^e$ System, Mettler Toledo, Switzerland). This analysis was performed with approximately 10 mg of dried sample under a nitrogen atmosphere (200 mL/min) at a heating rate of 10° C. per min.

Example 2

Polymer Synthesis

Preparation of the Cross-Linked P(MAA-MBAA) Nanoparticles:

In exemplary procedures, P(MAA-MBAA) nanoparticles of hydrodynamic sizes ranging from 18±2 to 460±60 nm were formed by surfactant-free dispersion copolymerization of the monomers MAA and MBAA in water as a continuous phase. In exemplary procedures, P(MAA-MBAA) nanoparticles of 27±3 nm hydrodynamic diameter were formed by dissolution of 4.4 g of MAA, 3.6 g of MBAA (2% w/v total monomers), and 240 mg of PPS in 400 mL of distilled water. The 1 L round-bottom flask containing this solution was stirred with a mechanical stirrer (200 rpm) at 100° C. for 1 h. The MAA and MBAA residues were subsequently removed from the nanoparticle aqueous dispersion by extensive dialysis against water. The dried P(MAA-MBAA) nanoparticles were obtained by lyophilization. FIG. 1 presents a schematic illustration of the synthesis process.

Effect of Various Parameters on the Characterization of the Cross-Linked P(MAA-MBAA) Nanoparticles:

In further exemplary procedures, as detailed in the Results section that follows, the following parameters were tested in respect to the nanometric size and/or the size distribution of the P(MAA-MBAA): total monomer concentration; effect of the initiator type and concentration; the weight ratio [MBAA]/[MAA]; polymerization temperature; polymerization duration time.

Results

Figure 2:
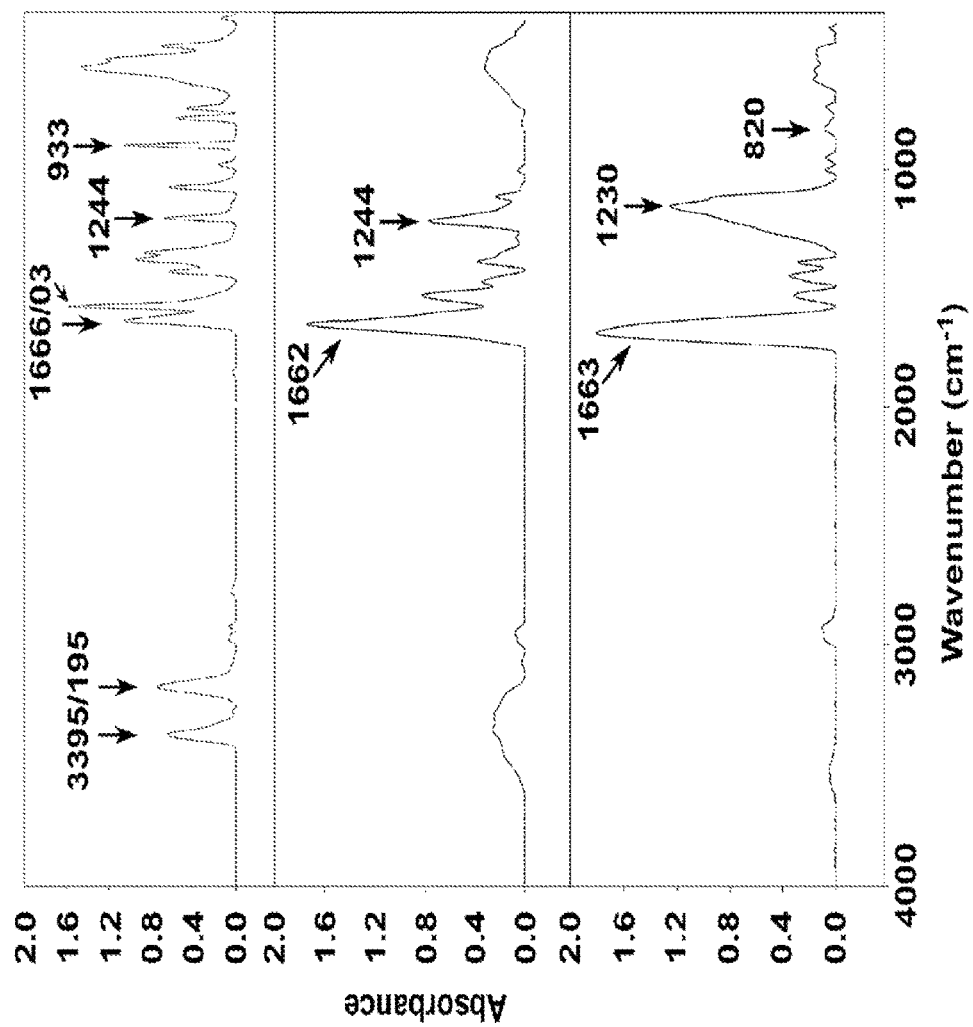
FIGS. 2A-C are graphs of fourier transform infrared (FTIR) spectra of the monomer MAA (FIG. 2A) and the P(MAA-MBAA) (FIG. 2B) and P(MAA-MBAA)-Cl (FIG. 2C) polymeric nanoparticles as prepared.

General Characterization:

FTIR spectra were recorded to verify the polymerization process and halogenation of the P(MAA-MBAA) nanoparticles. FIG. 2 presents the IR spectrum of the MAA monomer (A) and P(MAA-MBAA) polymeric nanoparticles before (B) and after (C) the chlorination process. The interpretation of the MAA monomer spectrum is known from the art and includes peaks at 930 $cm^{-1}$ (corresponding to the stretching of the C—H bonds on $CH_2$=C), at 1,244 $cm^{-1}$ (corresponding to the stretching of C—N bonds), at 1,603 $cm^{-1}$ (corresponding to the conjugated double bond vibration), at 1,666 $cm^{-1}$ (corresponding to the carbonyl vibration (amide) and N—H bend (amide)), and at 3,195 and 3,395 $cm^{-1}$ (corresponding to the symmetric and asymmetric stretching of $NH_2$, respectively). The IR spectrum of the cross-linker monomer MBAA is similar to that of MAA because these monomers contain similar bond types. FIG. 2B, which represents the P(MAA-MBAA) polymeric nanoparticles, illustrates that the peaks attributed to the C=C bond at 1,603 and the stretching of the C—H bonds on $CH_2$=C at 933 $cm^{-1}$ both disappear. This result indicates that the polymeric particles are indeed free of the monomeric moiety. The broadening of the existing peaks in the polymeric nanoparticles (FIG. 2B) relative to the monomer units (FIG. 2A) is also expected. FIG. 2C, representing the P(MAA-MBAA)-Cl polymeric nanoparticles, illustrates the same peaks as in FIG. 2B except for the peak at 3,195 $cm^{-1}$, which has nearly disappeared and is replaced by a new peak at 820 $cm^{-1}$ corresponding to the newly formed N—Cl bond. The C—N peak at 1,230 $cm^{-1}$ corresponding to the chlorinated polymeric nanoparticles (FIG. 2C) is significantly larger than that belonging to the non-chlorinated nanoparticles (FIG. 2B). It is assumed that the substitution of C—N—H for C—N—Cl shifted the corresponding peak from 1,244 to 1,230 $cm^{-1}$ and increased the intensity of the C—N vibrational bond.

TGA was next performed for both P(MAA-MBAA) and P(MAA-MBAA)-Cl. As shown in FIG. 3, the 5% weight loss near 100° C. for both particles is likely due to water evaporation. The TGA thermogram of the P(MAA-MBAA) nanoparticles indicates a dramatic weight loss (75%) in the range of 295-450° C. due to polymer decomposition. The P(MAA-MBAA)-Cl nanoparticles display approximately 80% total weight loss from 200 to 455° C. with two main decomposition slopes. The first slope between 200° C. and 320° C. demonstrates a 15% weight loss, attributed primarily to N—Cl decomposition (Cl release). The second slope between 320° C. and 450° C. exhibits a 55% weight loss, attributed to polymer decomposition. FIG. 3 also indicates the earlier decomposition of the chlorinated particles, likely due to the loss of mechanical strength as a consequence of the chlorination process.

The evaluation of the size of P(MAA-MBAA) nanoparticles was performed using both cryo-TEM (FIG. 4A) and dynamic light scattering (DLS) (FIG. 4B). As demonstrated in FIG. 4, a significant gap exists between the hydrodynamic and dry diameters. The hydrodynamic diameter and size distribution of the P(MAA-MBAA) nanoparticles in the aqueous phase were 27±3 nm, whereas the dry diameter and size distribution determined from the cryo-TEM image (black dots) were 5±2 nm. The difference between the dry and hydrodynamic diameters of these particles is likely due to their hydrophilic nature. When dispersed in an aqueous phase, these particles are likely to contain a substantial amount of absorbed and surface adsorbed water, which increases their diameter relative to the dried particles.

Effect of Various Parameters on the Characterization of the Cross-Linked P(MAA-MBAA) Nanoparticles:

Total Monomer Concentration:

The effect of the monomers (MAA and MBAA) (at a steady ratio of 55% MAA and 45% MBAA but with different total concentrations) on the hydrodynamic size and size distribution of the produced P(MAA-MBAA) nanoparticles is shown in FIG. 5. Without being bound by any particular theory, it is assumed that the system is sensitive in view of the fact that a final monomer concentration greater than 3% resulted in aggregated nanoparticles, whereas no nanoparticles were detected at a concentration lower than 1%. In this range, e.g., when the concentration of the MAA and MBAA was increased from 1% to 2% and 3% (w/v), the hydrodynamic diameter and size distribution of the formed P(MAA-MBAA) nanoparticles increased from 18±2 nm to 72±7 nm and 331±43 nm, respectively. Without being bound by any particular theory, the increase in the average diameter of the formed P(MAA-MBAA) nanoparticles can be explained by the effect of the monomer concentrations on the dispersion polymerization mechanism. A greater monomer concentration in the aqueous continuous phase led to longer oligoradicals before termination, resulting in an increase in the average diameter.

Initiator Type:

The effect of the initiator type (PPS and AIBN) and concentration on the hydrodynamic size and size distribution of the formed P(MAA-MBAA) nanoparticles was examined. As shown in FIG. 6, the P(MAA-MBAA) nanoparticles display a moderate increase in the hydrodynamic diameter and size distribution correlated with an increase in the concentration of the PPS initiator (in the range of 1% to 7%). For example, in the presence of 2%, 3%, and 7% PPS, the nanoparticle size and size distribution increased from 32±4 nm to 69±7 nm and 81±10 nm, respectively. These data are compared with that of AIBN, which indicated higher diameters in the same concentration range with a similar tendency, e.g., in the presence of 2%, 3%, and 7%, the nanoparticle size increased from 46±5 nm to 164±17 nm and 264±27 nm, respectively. Without being bound by any particular theory, it is assumed that increasing the initiator concentration causes an increase in the instantaneous concentration of the oligomeric radicals, which in turn increases the rate of association of the oligomers of the unstable nuclei to form larger permanent particle nuclei and thus larger final particle sizes. The difference between P(MAA-MBAA) nanoparticle diameters if prepared with PPS or AIBN can be explained by the difference in the dissociation constant ($K_d$). The $K_d$ of AIBN is $9.0\times10^{-5}$ (80° C. in water), which is higher than the $K_d$ of PPS, which is $6.9\times10^{-5}$ (80° C. in water). The higher decomposition rate of AIBN increases the instantaneous concentration of the oligomeric radicals, resulting in an increased average diameter of the obtained nanoparticles, as mentioned previously.

Effect of the Weight Ratio [MBAA]/[MAA] on Nanoparticle Size:

The MAA was polymerized with MBAA by dispersion co-polymerization in water as a continuous phase to obtain nanoparticles rather than soluble polymer, which was accomplished by holding the total monomer (MAA+MBAA) weight % constant at 2% while the weight ratio between the two monomers ([MBAA]/[MAA]) was varied from 1/9 to 6/4. Increasing this ratio above 6/4 (e.g., to 7/3) resulted in the formation of severely agglomerated particles. FIG. 7 presents the effect of the weight ratio of [MBAA]/[MAA] on the diameter and size distribution of the formed P(MA-MBAA) nanoparticles. The results suggest that the diameter and size distribution increase with increases in the [MBAA]/[MAA] weight ratio. For example, when this ratio was increased from 0.11 to 0.43 and 0.82, the average size and size distribution increased from 10±1 nm to 19±2 nm and 71±8 nm, respectively. This behavior was surprising because it is expected to obtain more compact nanoparticles as the content of the cross-linked points in the polymer increased. Without being bound by any particular theory, this behavior may be explained by the fact that increasing the hydrophilic properties of the obtained P(MAA-MBAA) nanoparticles (MBAA is more hydrophilic than MAA) leads to an increased amount of absorbed and surface-adsorbed water molecules, resulting in an increased hydrodynamic nanoparticle size.

Effect of the Polymerization Temperature on Nanoparticle Size:

During the course of the current research, the polymerization temperature was observed to be an effective parameter to control the size of the obtained nanoparticles. FIGS. 8A-B present the effect of polymerization temperatures between 60° C. and 100° C. on the size and size distribution (A) and on the polymerization yield (B) of the formed P(MAA-MBAA) nanoparticles.

FIG. 8A demonstrates that increasing the polymerization temperature leads to a sharp decline in the particle diameter and diameter distribution, from 331±48 nm at 60° C. to 28±3 nm at 100° C. Similar results, indicating a decrease in the polymeric particle diameter with increasing temperature, have been reported by several groups for dispersion polymerization. However, a few research groups have reported the opposite trend (Bamnolker H, et al., *J. Polym. Sci.* 1996; 34:1857, Harding I H. *Colloid Polym. Sci.* 1985; 263,58.) and suggested that increasing the temperature leads to increasing initiator decomposition, which causes a higher concentration of "activated initiator" and leads to increases in the polymerization rate and particle size. The explanation for the opposite trend, i.e., a size decrease as a result of temperature increase, is that the high temperature leads to increased concentration of the decomposed initiator, which may cause the formation of many nuclei such that each nucleus becomes smaller than what observed at lower temperature.

FIG. 8B demonstrates that the polymerization yield between 60° C. and 90° C. is similar, approximately 90%. At 100° C., the polymerization yield declined slightly to 80%, likely due to a higher decomposition rate of the initiator, which may cause side reactions and/or early termination and lower polymerization yield.

Kinetics of Polymerization:

The effect of the polymerization duration time on the diameter and size distribution (FIG. 9A) and polymerization yield (FIG. 9B) of the formed P(MAA-MBAA) nanoparticles prepared was examined. The kinetics were studied at 100° C. because the smallest nanoparticles with the narrower size distribution of 28±3 nm were obtained at this temperature, as illustrated in FIGS. 8A-B. FIG. 9 illustrates that after 1, 5, and 30 min, the size increased from 16±2 nm to 24±3 nm and 27±3 nm, respectively, and the yield increased from 31% to 69% and 96%, respectively. After 30 min and up to 3 h, the size and yield of P(MAA-MBAA) nanoparticle formation did not vary significantly because the polymerization process was nearly complete after 30 min.

Example 3

Chlorination of the P(MMA-MBAA) Nanoparticles

Chlorination of the P(MAA-MBAA) Nanoparticles:

Following the synthesis of the optimal P(MAA-MBAA) nanoparticles, P(MAA-MBAA) nanoparticles of 27±3 nm hydrodynamic diameter were used to investigate the effect of varying the chlorination process parameters as follows: Sodium hypochlorite aqueous solution (5 mL, 4% w/v) was added to an aqueous dispersion of the P(MAA-MBAA) nanoparticles (5 mL, 15 mg/mL), which was shaken at room temperature for 1 hour. Excess sodium hypochlorite was removed from the P(MAA-MBAA)-Cl nanoparticle dispersion by extensive dialysis against water. The bound-Cl content of the P(MAA-MBAA)-Cl nanoparticles was determined by iodometric/thiosulfate titration according to the art using the following expression:

$$Cl^+(mM) = \frac{N \times V \times 1000}{2}$$

where N is the normality (equiv/L) and V is the volume (L) of the titrated sodium thiosulfate solution.

In further exemplary procedures, as detailed in the Results section that follows, the following chlorination parameters were tested in respects to the Cl content: NaOCl concentration, chlorination time, and chlorination temperature.

In exemplary procedures, other halogens were used, and the NPs were suspended in sodium hydroxide solution and the halogen (bromine or iodine) was added gradually until neutralization to pH 7. Excess sodium hypochlorite/hypobromite/hypoiodite was removed from the halogenated P(MAA-MBAA) NPs dispersion by extensive dialysis against water. The bound-halogen (Br or I) content of the halogenated P(MAA-MBAA) NPs was determined either by adding e.g., sodium iodide and measuring the formed color spectrophotometrically at 292 nm and 350 nm or by iodometric/thiosulfate titration.

For determining the I content on the P(MAA-MBAA)-I NPs, analytical chemical elements was conducted.

Effect of the Chlorination Parameters

Effect of NaOCl Concentration on the Cl Content of the P(MAA-MBAA)-Cl Nanoparticles:

To characterize the effect of sodium hypochlorite (NaOCl) concentration on the Cl content of the P(MAA-MBAA)-Cl nanoparticles, increasing concentrations of NaOCl was conducted as presented in FIG. 10. This figure illustrates that, increasing the NaOCl concentration leads to an increase in the bound Cl loading of the nanoparticles. For example, in the presence of 0.8%, 2%, and 3.2% NaOCl, the bound Cl content of the P(MAA-MBAA)-Cl nanoparticles increased from 20.8 mM to 41.4 mM and 67.5 mM, respectively. The effect of NaOCl concentrations greater than 3.2% on the bound Cl content could not be measured due to the significant damage that occurred to the dialysis membranes under these conditions.

Figure 11:
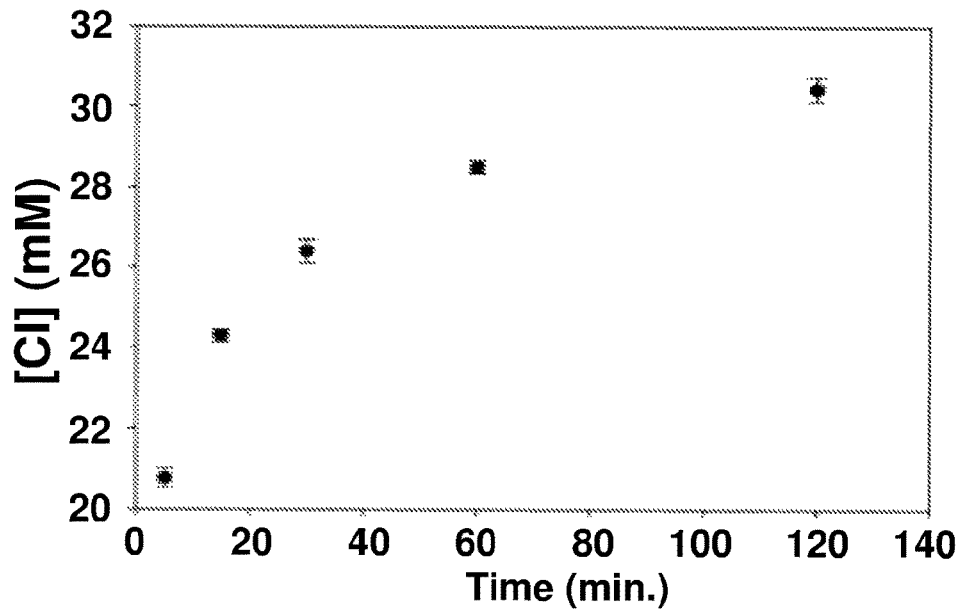
FIG. 11 presents a point graph showing the influence of the chlorination time on the Cl content of the P(MAA-MBAA)-Cl nanoparticles as prepared and further chlorinated.

Effect of the Chlorination Time on the Cl Content of the P(MAA-MBAA)-Cl Nanoparticles:

The effect of the chlorination time on the Cl content of the P(MAA-MBAA)-Cl nanoparticles aqueous dispersion was tested as demonstrated in FIG. 11. The presented trend illustrates that increasing the chlorination duration from 5 min to 120 min leads to an active Cl content increase from 20.7±0.25 mM to 30.4±0.3 mM. The main charging increase occurs within the first 30 min, followed by milder increase over the next 120 min. For example, the bound Cl content evaluated after 30 min of chlorination was 26.4±0.3 mM, whereas the extension of the chlorination process to 120 min yielded a Cl content of only 30.4±0.3 mM.

Figure 12:
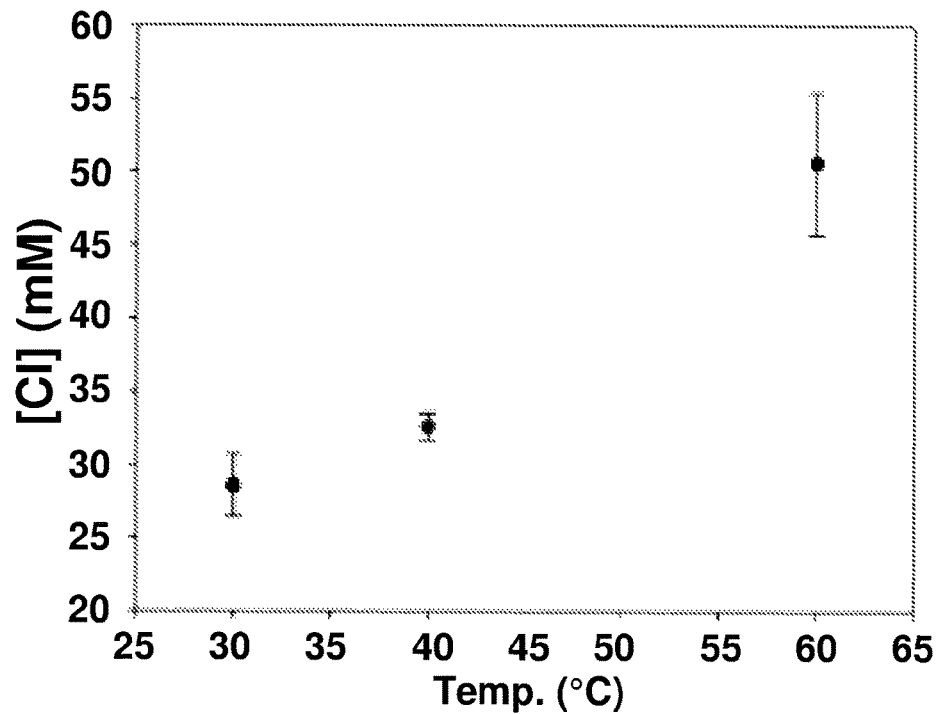
FIG. 12 presents a point graph showing the influence of the chlorination temperature on the Cl content of the P(MAA-MBAA) nanoparticles as prepared and thereafter chlorinated.

Effect of Chlorination Temperature on the Cl Content of the P(MAA-MBAA)-Cl Nanoparticles:

The chlorination process was carried out at three different temperatures of 30° C., 40° C., and 60° C. for 1 h. FIG. 12 illustrates the effect of the chlorination temperature on the Cl content of the chlorinated P(MAA-MBAA) nanoparticles at pH 7. Increasing the chlorination temperature from 30° C. to 40° C. and 60° C. leads to an increase of the bound Cl content from 28±2 mM to 32±0.9 mM and 50±4.9 mM, respectively. Increasing the temperature increases the reactivity of the sodium hypochlorite, leading thereby to increased chlorination.

Figure 13:
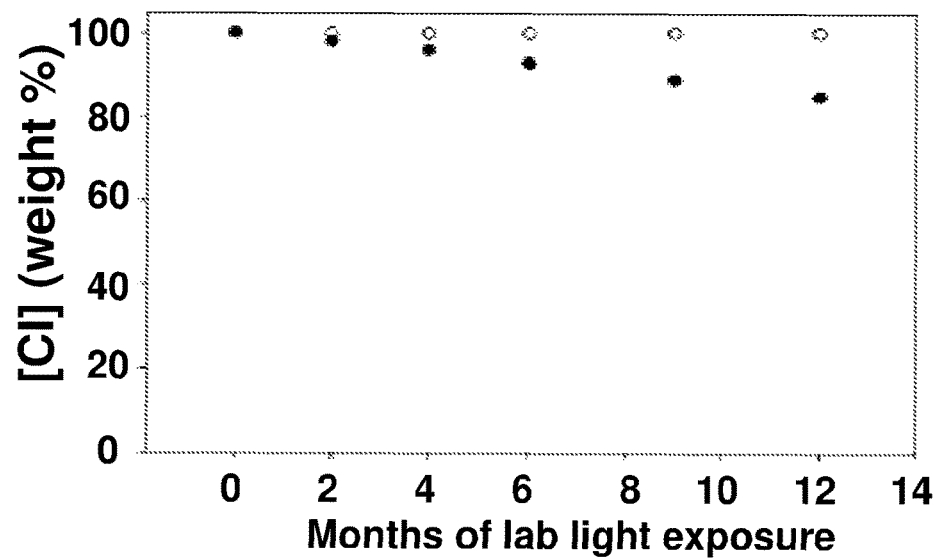
FIG. 13 presents a point graph showing the % bound Cl content of the P(MAA-MBAA)-Cl nanoparticles stored for different periods of time under laboratory light conditions before (black dots) and after (open circle dots) rechlorination.

Extent of Cl Release and Rechargeability of the P(MAA-MBAA)-Cl Nanoparticles' Aqueous Dispersion Irradiated by Laboratory or UV Light:

In exemplary procedures, the stability and rechargeability of the bound Cl of the P(MAA-MBAA)-Cl nanoparticles dispersed in water (20 mL, 4 mg/mL) were evaluated by exposure to laboratory or UVA (365 nm) light, as described in hereinabove. FIG. 13 illustrates the change over time of the % Cl of the P(MAA-MBAA)-Cl nanoparticle aqueous dispersion stored under laboratory light conditions. The results indicate a relatively high stability of the N—Cl bond. Storing the chlorinated nanoparticles under laboratory light conditions for four months and for one year results in the presence of 95% and 85% of the initial bound Cl, respectively. Following a Cl recharging process, as described in the experimental section, the bound Cl content returned to its initial value even after one year of storage under laboratory light conditions (FIG. 13). It is assumed that the recharging process changed the N—H bonds of the co-polymeric nanoparticles to N—Cl bonds such that the concentration of the N—Cl groups returned to that of the initial concentration. A similar study by Worley et al. reported on the loss of approximately 80% bound Cl within four weeks of N-halamine silane polymer coatings on cotton fabric stored in laboratory light conditions. This result may indicate that the N—Cl bonds of the P(MAA-MBAA)-Cl are more stable than those of the N-halamine silane polymers used by Worley et al. (*Colloid Surf A* 2009; 345).

Figure 14:
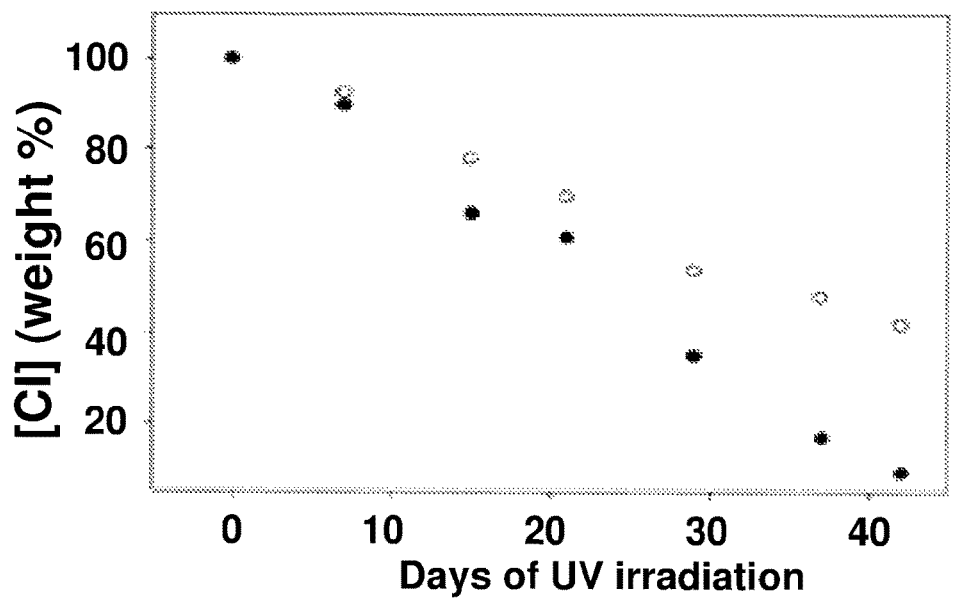
FIG. 14 presents a point graph showing the % bound Cl content of the P(MAA-MBAA)-Cl nanoparticles irradiated with UVA light for different periods of time before (black dots) and after (open circle dots) rechlorination.
Figure 15A:
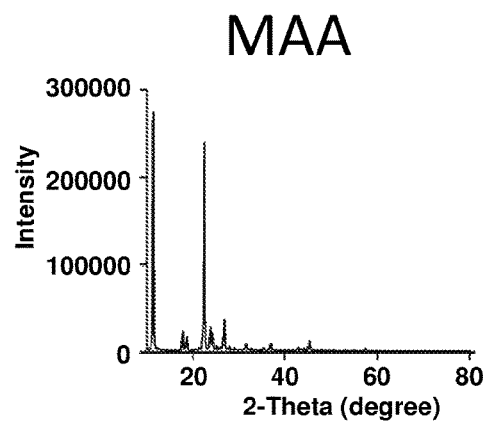
FIGS. 15A-D present graphs showing x-ray diffraction (XRD) patterns of the monomers MAA (FIG. 15A), MBAA (FIG. 15B) and the polymerized NPs P(MAA-MBAA) (FIG. 15C) and the charged ones with Cl (FIG. 15D).
Figure 15B:
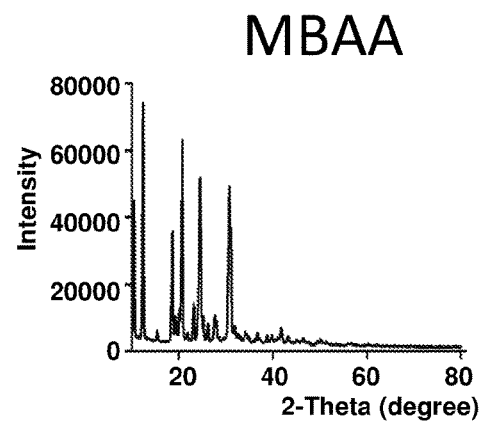
Figure 15C:
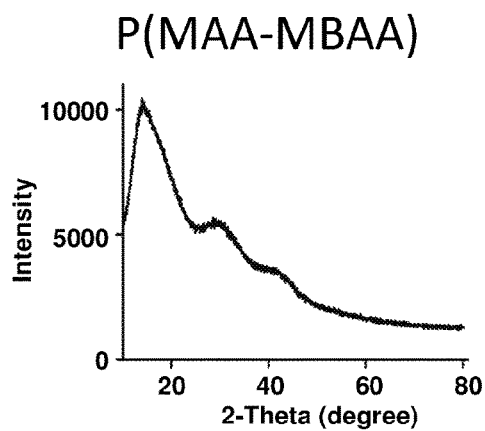
Figure 15D:
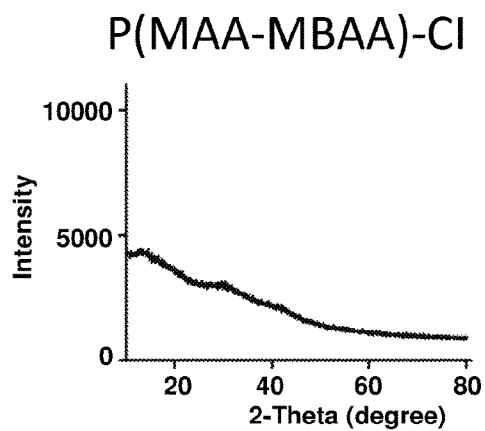

In additional exemplary procedures, the stability and rechargeability of the bound Cl of the P(MAA-MBAA)-Cl nanoparticles irradiated with UVA over 42 days were examined (FIG. 14). A significant acceleration of the bound Cl loss due to the UVA irradiation was observed. For example, during the 42 days of UVA irradiation, the loss of bound Cl was 91%, whereas the loss of bound Cl for nanoparticles stored under laboratory light conditions was less than 2%. In addition, FIG. 14 illustrates that the rechlorination of the UVA-irradiated nanoparticles was only partially successful, e.g., the % bound Cl after 42 days of UVA irradiation returned from 9% to 40% of its initial value after the rechlorination process. These results suggest that the UVA irradiation in addition to the hydrolysis of the N—Cl bond partially breaks the polymeric chains of the nanoparticles.

Example 4

Chlorination Cycle

Chlorination/De-Chlorination Cycles of the P(MAA-MBAA) Nanoparticles:

Five chlorination/de-chlorination cycles were performed on the P(MAA-MBAA) nanoparticles. In exemplary procedures, 60 mL of the P(MAA-MBAA) nanoparticle aqueous dispersion (15 mg/mL) were chlorinated with 60 mL of sodium hypochlorite aqueous solution (4% w/v), followed by the removal of excess hypochlorite as described hereinbelow. Two 1 mL samples were removed for analysis of the bound Cl content of the P(MAA-MBAA)-Cl nanoparticles via iodometric/thiosulfate titration. The remaining P(MAA-MBAA)-Cl dispersed in water were de-chlorinated by shaking this dispersion for 5 min with 30 mL of 0.1 N sodium thiosulfate solution. Excess reagents were removed from the nanoparticle aqueous dispersion by extensive dialysis against water. Next, the P(MAA-MBAA)-Cl nanoparticle aqueous dispersion was concentrated by water evaporation to the original volume (60 mL). This chlorination/de-chlorination process was repeated another four times.

The renewability of the P(MAA-MBAA)-Cl nanoparticles was evaluated for five cycles. Table 1 below illustrates that the bound Cl content of the nanoparticles at each cycle was similar to that in the first cycle after the chlorination step was completed. This result proves the effective rechargeability of these cross-linked N-halamine nanoparticles.

TABLE 1

| Cycle number | Bound Cl (µM/mg) |
| --- | --- |
| 1 | 2.76 |
| 2 | 2.81 |
| 3 | 2.54 |
| 4 | 2.61 |
| 5 | 2.65 |

Example 5

Characterization Analysis

NMR:

Solid state-NMR was conducted as a complementary analysis to the characterization to monitor the polymerization process and distinguish between the chlorinated and non-chlorinated P(MAA-MBAA) NPs.

Exemplary solid state NMR experiments were performed on a Bruker Advance III 500 MHz narrow-bore spectrometer, using a 4 mm double-resonance magic angle spinning (MAS) probe. 13 C CPMAS experiments were carried out at a spinning rate of 8 kHz, using a 2.8 us 1H 90° pulse, 2k data points and a 2 ms ramped-CP period. Proton decoupling using the SPINAL composite pulse sequence at a field of 100 kHz was used during acquisition with a 3 s recycle delay between acquisitions. Chemical shifts were given with respect to adamantane (38.55, 29.497 ppm).

XRD:

Powder X-ray diffraction (XRD) patterns were recorded using an X-ray diffractometer (Model D8 Advance, Bruker AXS) with Cu Ka radiation.

Zeta Potential:

Zeta potential measurements were performed by Wallis zeta potential analyzer (Cordouan, France).

Cryo-TEM:

The size of the dried particles was evaluated and imaged with a cryogenic transmission electron microscope (cryo-TEM). Samples for cryo-TEM were prepared by placing a droplet of the solution on a TEM grid coated with holey carbon film (lacey carbon, 300 mesh, Ted Pella, Inc.), followed by automatic blotting of the excess liquid. The specimen was vitrified by rapid plunging into liquid ethane precooled with liquid nitrogen in a controlled environment vitrification system (Leica EM GP). The vitrified samples were transferred to a cryospecimen holder (Gatan model 626) and examined at −178° C. in low-dose mode. Imaging was carried out using FEI Tecnai 12 $G^2$ equipped with Gatan 794 CCD camera and operated at 120 kV.

Results

NMR:

The dried P(MAA-MBAA) NPs were obtained by lyophilization and were verified by the solid-state NMR. The NMR results are summarized as follows:

MAA monomer: $^1$H NMR (solid) δ 1.93 (s, 3H, Me), 5.12 (s, 1H, vinyl), 5.91 (s, 1H, vinyl), 8.38 (bs, 2H, $NH_2$).

$^{13}$C NMR (solid) δ 19.80 (Me), 122.95 ($CH_2$-vinyl), 138.82 (C-vinyl), 171.63 (C=O). P(MAA-MBAA) NPs: $^1$H NMR (solid) δ 1.83 (brs, 12H, $CH_2CHCH_3$ of MMA and 2×$CH_2$CH—C of MBBA), 4.77 (s, 2H, N—$CH_2$—N), 8.12 (bs, 4H, $NH_2$ and $NHCH_2NH$)

$^{13}$C NMR (solid) δ 18.73 (C—$CH_2$—C), 21.15 (Me and $CH_2$—$CH_2$—C=O), 41.87 (Me-C—C=O), 45.72 (NH—$CH_2$—NH), 180.21 (C=O).

The P(MAA-MBAA) NPs were verified by the disappearance of the vinylic proton peaks at 5.12 and 5.91 ppm, and appearance of broad peaks of the polymer aliphatic protons at 1-3.5 ppm. Additionally, new cross-linker methylen protons appeared at 4.77 ppm. The chlorination was also verified by 1H NMR. The amide proton peak at 7-9 ppm disappeared when H replaced Cl, and the methylen proton peak was shifted to 5.5 ppm because of the chlorination of the methylen substitutions.

XRD:

XRD characterization presented in FIG. 15 demonstrate the X-ray diffraction (XRD) patterns of the MAA and MBAA monomers versus the P(MAA-MBAA) NPs and the chlorinated ones. The XRD measurements on the MAA and MBAA monomers powders display clear sharp and narrow diffraction peaks, typically observed for crystalline materials (FIGS. 15A-B), while the X-ray powder diffraction of the NPs revealed very poor diffraction patterns, pointing to the amorphous nature of the NPs (FIG. 15C-D).

Zeta Potential:

The zeta potential was also evaluated for the NPs as it may affect their stability. The zeta potential was found to be negative; −11.3 mV and −12.72 mV for the chlorinated NPs and their non-chlorinated counterparts, respectively.

Cryo-TEM:

The P(MAA-MBAA)-Cl NPs were also imaged using cryo-TEM as this reveals their dry size (FIG. 16) which was estimated to be between 5 to 9 nm.

The percent conversion (polymerization yield) of the monomers to P(MAA-MBAA) nanoparticles was calculated using the following expression:

$$\text{Polymerization yield (weight \%)} = \frac{W_{P(MAA-MBAA)}}{W_{(MAA+MBAA)}} \times 100$$

where $W_{P(MMA-MBAA)}$ is the weight of the obtained dried P(MAA-MBAA) nanoparticles and $W_{(MAA-MBAA)}$ is the initial weight of the monomers MA and MBAA. P(MAA-MBAA) nanoparticles of different sizes were formed by varying various polymerization parameters, e.g., monomer concentration, initiator type, and concentration.

Example 6

Antibacterial Examination

Methods

Bacterial Cultures and Growth Conditions:

In exemplary procedures, *Escherichia coli* (*E. coli*) C600, *Staphylococcus aureus* (*S. aureus*) FRF1169, and multi-drug resistant strains *E. coli* 5327752, *Klebsiella pneumoniae* 5363271, and *Providencia stuartii* 5327311 were grown overnight at 37° C. under agitation (250 rpm) in Luria Bertani (LB, Difco) growth medium.

Antimicrobial Activity Assay of the P(MAA-MBAA)-Cl Nanoparticles and NaOCl:

In exemplary procedures, the antimicrobial activity of the P(MAA-MBAA)-Cl nanoparticles was evaluated by determining the minimum inhibitory concentration (MIC) values for both *E. coli* and *S. aureus*. The MIC was defined as the lowest Cl concentration bound to the nanoparticles, or the NaOCl, at which no bacterial growth was visible following incubation with the respective bacteria. The stock solution of the P(MAA-MBAA)-Cl nanoparticles and NaOCl were each diluted in two-fold serial dilutions in a 96-well plate (Griener Bio-one) ranging from bound Cl concentrations of 10 to 0.08 mM (approximately corresponding to 0.8% P(MAA-MBAA)-Cl, w/v) in LB medium in a 96-well plate (Greiner Bio-one). Each well contained $10^5$ colony-forming units (CFU)/mL of either *E. coli* or *S. aureus*, and bacteria were either treated with P(MAA-MBAA) nanoparticles or left untreated to serve as negative controls. The bacterial growth was monitored via absorbance measurements at OD$_{595}$ utilizing a microplate reader (Synergy 2, BioTek instruments). All experiments were conducted in triplicate.

Bacterial-Killing Kinetics in the Presence of the P(MAA-MBAA)-Cl Nanoparticles and NaOCl:

In exemplary procedures, overnight cultures of *E. coli* and *S. aureus* bacteria were each diluted in a fresh LB medium to obtain stock solutions with a working concentration of $10^5$ CFU per mL. Next, *E. coli* and *S. aureus* bacteria were grown, each with different doses of overnight at 37° C. under agitation (250 rpm) with equivalent volumes of either NaOCl, P(MAA-MBAA) or P(MAA-MBAA)-Cl nanoparticles (0.2%, 0.75%, and 1% w/v) under continuous agitation (250 rpm). At various time points, 100 µL samples were taken from each tube and transferred into the wells of the first row in a 96-well plate that contained 20 µL of 0.1 N sodium thiosulfate. The latter was added to quench the remaining Cl on the P(MAA-MBAA)-Cl nanoparticles, thus halting the reaction. Serial dilutions were carried out, and the cells were spotted onto LB agar plates, followed by incubation at 37° C. for 20 hours. Cell growth was monitored and determined by viable cell count and expressed as CFU/mL.

Incubation of P(MAA-MBAA)-Cl NPs and NaOCl with Consecutive Bacterial Loading Cycles:

The cell density of *E. coli* and *S. aureus* grown overnight was normalized to 2*$10^5$ cells per milliliter in a twofold concentrated LB medium; then the bacteria were treated for 1 h at 37° C. under agitation (250 rpm) with equivalent volumes of either NaOCl or P(MAA-MBAA)-Cl NPs. Bacteria shaken with water served as a negative control. After 1 h of incubation, aliquots were collected and diluted serially tenfold before spotting onto LB agar plates. After an overnight incubation at 37° C. the colony forming units (CFU) were counted and used to determine cell survival. Immediately after each aliquot was removed, newly prepared bacteria were added for another hour to each of the tubes to achieve a final concentration of $10^5$ CFU/ml.

Antimicrobial Activity of the P(MAA-MBAA)-Cl Nanoparticles Against Multi-Drug Resistant (MDR) Bacteria:

In exemplary procedures, the antibacterial activity of the P(MAA-MBAA)-Cl nanoparticles was tested against three clinical isolates (blood isolates) isolated and characterized in the Tel-Aviv medical center "Ichilov": *E. coli* 5327752 (resistant to Gentamicin and Ampicillin), *Klebsiella pneumoniae* 5363271 (resistant to Gentamicin, Ciprofloxacin, and Ampicillin) and *Providencia stuartii* 5327311 (resistant to Gentamicin, Ampicillin, and Colistin). All three strains were grown overnight followed by dilution in LB medium to obtain a concentration of $10^5$ CFU/mL. The bacterial suspensions were incubated overnight with equivalent volumes of either 1.4% (w/v) P(MAA-MBAA) or P(MAA-MBAA)-Cl or 0.6% (w/v) nanoparticles. Bacteria treated with sterilized water served as an additional negative control. On the following day, 10-fold serial dilutions were carried out, and the bacterial cells were plated on LB agar plates. The plates were incubated overnight at 37° C. followed by CFU/mL determination.

Biosensor Bacteria Screening Assay:

A panel of seven modified *E. coli* strains (agur-Kroll, S.; Belkin, S. *Anal. Bioanal. Chem.* 2011, 400, 1071) was utilized for this study. Each strain contains a multi-copy plasmid in which the promoter of interest is fused to the *Vibrio fischeri* luxCDABE genes, such that promoter activation, for example by toxic stress, drives the synthesis of luciferase, ultimately resulting in bioluminescence. All strains were handled alike. Bacteria were grown overnight at 37° C. under agitation (250 rpm) in LB that was supplemented with 100 mg/ml ampicillin to guarantee plasmid maintenance. The following day, the culture was diluted 1:100 with fresh LB media and incubated at 30° C. under agitation (200 rpm) until an OD$_{595}$ of 0.1-0.2 was reached. 100 µl of either distilled water or P(MAA-MBAA)-Cl NPs or their non-chlorinated counterparts was added in triplicate to the first row of an opaque white 96-well plate (Griener Bio-one). Then all wells were filled with 100 µl of the culture, now in logarithmic phase, and 2-fold serial dilution conducted to generate oxidative chlorine concentrations ranging from 0.01 M to 0.08 mM. The plate was placed in a luminometer (in the dark) and luminescence was measured at 10' intervals at a constant temperature (25° C.).

Bacterial Killing Kinetics in the Presence of P(MAA-MBAA)-Cl NPs and NaOCl:

Cultures of *E. coli* and *S. aureus* bacteria grown overnight were diluted in fresh twofold concentrated LB medium to obtain stock solutions with a final working concentration of 10^5 CFU/ml. Then, *E. coli* and *S. aureus* bacteria were grown with either P(MAA-MBAA)-Cl NPs or NaOCl under continuous agitation (250 rpm). Bacteria grown with distilled water or P(MAA-MBAA) NPs served as negative controls. At various time points, 100 µl samples were taken from each tube and transferred into the first row wells of a 96-well plate containing 20 µl of 0.1 N thiosulfate. The latter was added to quench the remaining chlorine on the P(MAA-MBAA)-Cl NPs and NaOCl, thus terminating the sterilization process. Serial dilutions were carried out and the cells spotted onto LB agar plates, which were incubated at 37° C. for 20 h. Cell growth was monitored and determined by a viable cell count.

Bacterial Killing Kinetics of P(MAA-MBAA)-Cl NPs in the Presence of Antioxidants:

Cultures of *E. coli* and *S. aureus* bacteria grown overnight were diluted in fresh twofold concentrated LB medium to obtain stock solutions with a final working concentration of $10^5$ CFU/ml. Then, *E. coli* and *S. aureus* bacteria were grown with P(MAA-MBAA)-Cl NPs, that were either pre-incubated with the antioxidants (i.e. 10% DMSO, 10 mM NAC, 10 mM AA) or water for 1 h, under continuous agitation (250 rpm). Bacteria supplemented with distilled water or the various antioxidants served as negative controls. At various time points, 100 µl samples were taken from each tube and transferred into the first row wells of a 96-well plate containing 20 µl of 0.1 N thiosulfate. The latter was added to quench the remaining chlorine on the P(MAA-MBAA)-Cl NPs and NaOCl, thus terminating the sterilization process. Serial dilutions were carried out and the cells spotted onto LB agar plates, which were incubated at 37° C. for 20 h. Cell growth was monitored and determined by a viable cell count.

Transmission Electron Microscopy (TEM) of Bacterial Samples:

Samples of *S. aureus* and *E. coli* cultures ($10^9$ CFU/ml) or the human osteosarcoma cell line Saos-2 ATCC HTB-85 were centrifuged immediately after treatment with either distilled water, P(MAA-MBAA) NPs or P(MAA-MBAA)-Cl for the indicated time points. When indicated, *S. aureus* bacteria were boiled for 10' or pre-incubated at 4° C. for 2 h before adding the NPs. When indicated, DMSO was incubated with the chlorinated NPs for 1 h prior the addition of bacteria. In all the experiments, the bacteria were suspended in LB medium unless indicated otherwise. The samples were then fixed in 2.5% glutaraldehyde/paraformaldehyde in cacodylate buffer (Electron Microscopy Sciences). The samples were washed with cacodilate buffer and fixed in 1% osmium tetraoxide. Embedding of samples was carried out according to standard protocols (S. Croft. Electron Microscopy Methods and Protocols. In *Methods in molecular biology;* 1999; pp. 117.) and 60 nm thick slices were cut with a diamond knife (LBR ultratome III). The slices were deposited on bare 200 mesh copper grids, and stained with 2 wt % uranyl acetate for 5 min. Finally, the grids were dried in a desiccator and examined using JEOL 1200Ex transmission electron microscope at 80 kV. The percentage of cells marked with the particles was calculated by taking 20 representative microscope images containing all together 300 cells.

The Human Osteosarcoma Cell Line:

Saos-2 (ATCC #HTB-85) was maintained in Dulbecco's Minimum Essential Medium (DMEM) supplemented with heat-inactivated fetal bovine serum 10%, penicillin 100 IU/mL, streptomycin 100 3 g/mL, and 1-glutamine 2 mM, all these reagents were purchased from Biological Industries (Bet Haemek, Israel).

Scanning Electron Microscopy (SEM):

Samples of $10^9$ CFU/ml *S. aureus* cultures treated for 1.5 h with the P(MAA-MBAA) NPs or the chlorinated ones were fixed with glutaraldehyde and paraformaldehyde for 1 h. Following this incubation the samples were washed three times with a phosphate buffer saline (PBS). Samples were then immersed for 1 h in titanic acid and a glutamate solution in a 4:5 ratio concentration, respectively. Samples were afterwards washed three times with PBS and exposed to an osmium tetraoxide solution for 1 h. To dehydrate the samples, they were sequentially washed with water-ethanol and ethanol-Freon solutions (concentrations ranging from 50% to 100% for each solvent). Finally, the samples were dried in air for at least 24 h and then coated with a layer of carbon and examined using a FEI Quanta 200 FEG environmental scanning electron microscope.

Results

Antimicrobial Activity Assay of the P(MAA-MBAA)-Cl Nanoparticles and NaOCl:

The characterizing the bactericidal potential of P(MAA-MBAA)-Cl NPs was evaluated relative to the soluble non-nanometric N-halamine polymer MAA-Cl (i.e. PMAA-Cl) and to NaOCl, the chemical that was used to load the P(MAA-MBAA)-NPs with oxidative Cl and is the active ingredient of household bleach, one of the most commonly used disinfectants in the world. All three reagents release $Cl^+$ that kills bacteria and the oxidative chlorine concentrations used were 11 mM and 8 mM. As presented in Table 2 hereinbelow, the chlorinated NPs and NaOCl killed both *E. coli* and *S. aureus*, while the PMAA-Cl was much less effective and killed only *S. aureus*. These results show that P(MAA-MBAA)-Cl NPs and NaOCl are more effective than the non-nanometric PMAA-Cl.

TABLE 2

| Reagent name | E. coli | S. aureus |
| --- | --- | --- |
| P(MAA-MBAA)-Cl NPs (11 mM) | Total kill | Total kill |
| P(MAA-MBAA)-Cl NPs (8 mM) | Total kill | Total kill |
| PMAA-Cl (11 mM) | 6 logs (out of 10) | Total kill |
| PMAA-Cl (8 mM) | No killing | Total kill |
| NaOCl (11 mM) | Total kill | Total kill |
| NaOCl (8 mM) | Total kill | Total kill |

Next, the minimum inhibitory concentration (MIC) of the two agents was determined. *E. coli* and *S. aureus* were exposed to serial dilutions of either P(MAA-MBAA)-Cl NPs (aqueous dispersion) or NaOCl. The MIC of the two reagents was found to be the same, 5.6 mM oxidative Cl, for both *E. coli* and *S. aureus*. Notably, bacteria exposed to non-chlorinated P(MAA-MBAA) NPs did not exhibit growth arrest and behaved like untreated bacteria.

Figure 17A:
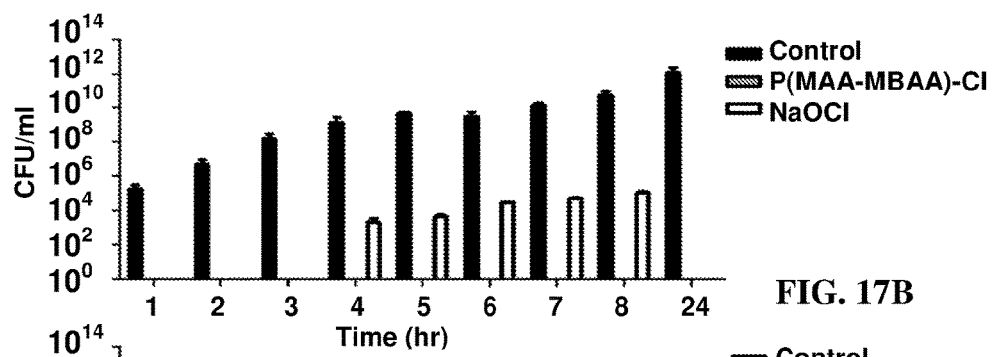
FIGS. 17A-B present bar graphs presenting the activity of P(MAA-MBAA)-Cl NPs and NaOCl following repetitive bacterial loading cycles for *E. coli* (FIG. 17A) and for *S. aureus* (FIG. 17B) treated with either P(MAA-MBAA)-Cl NPs, NaOCl, or being untreated. Every hour aliquots were removed from each sample and plated on agar plates. In parallel, $10^5$ CFU/ml (CFU: Colony-forming unit) freshly prepared bacteria were added. After the eighth loading cycle, the tubes were left in the shaker and samples taken the following day. Error bars represent the standard deviation of three independent experiments. It is to note that since the P(MAA-MBAA)-Cl were able to kill all the bacteria at all the indicated time points, the grey bars are not shown in the graphs.
Figure 17B:
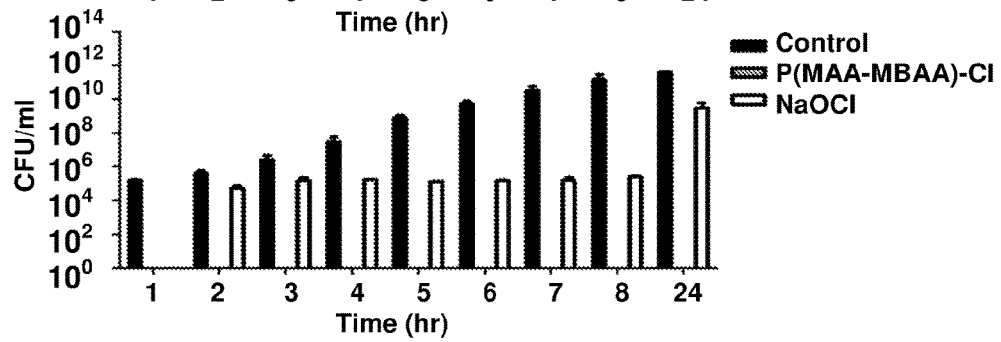

Incubation of P(MAA-MBAA)-Cl NPs and NaOCl with Consecutive Bacterial Loading Cycles:

The capability of chlorinated NPs versus NaOCl to withstand repetitive cycles of bacterial exposure. To this end, both *E. coli* and *S. aureus* were incubated with either NaOCl or the chlorinated NPs. This concentration was applied in all the experiments, unless indicated otherwise. Every hour a sample was taken from each tube and plated on agar plates, and in parallel $10^5$ CFU/ml freshly prepared bacteria were added. In total, 8 bacterial loading cycles were conducted. As presented in FIG. 17, the P(MAA-MBAA)-Cl NPs retained activity throughout the experiment, eradicating both *E. coli* and *S. aureus*. In contrast, NaOCl was no longer able to promote bacterial killing from cycle 4 for *E. coli* and from cycle 2 for *S. aureus*. It is to note that the quantity of bacteria exposed to bleach throughout the loading cycles did not reach the concentration of bacteria residing in the control test tube (i.e., untreated bacteria) (FIG. 17), suggesting that the bactericidal activity of bleach during this short incubation has been hampered. To investigate this premise, we checked the viability of bacteria sampled following an overnight incubation. After a longer exposure time to NaOCl, there were no viable *E. coli* bacteria which suggests that given enough time bleach still managed to kill the bacteria, whereas the *S. aureus* bacteria were able to overcome the growth inhibitory affect observed following the short exposure. These data demonstrate that *S. aureus* bacteria are more resistant to bleach than *E. coli*. Importantly, after an overnight incubation with P(MAA-MBAA)-Cl NPs, neither *E. coli* nor *S. aureus* bacteria were viable (FIG. 17).

Figure 18A:
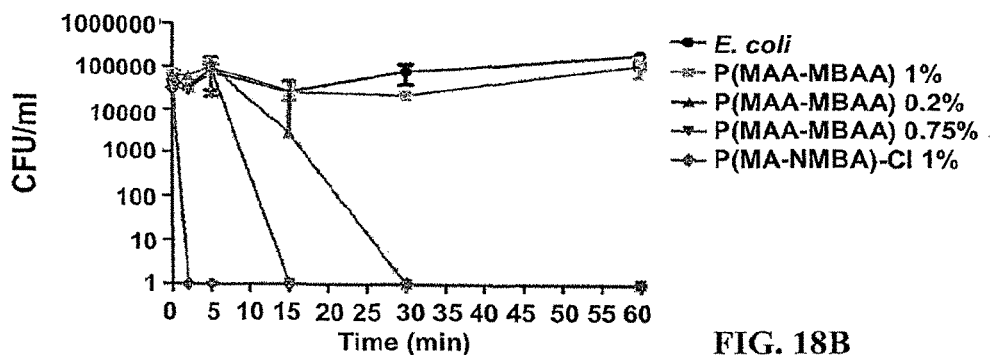
FIGS. 18A-B present graphs showing kinetic curves of *E. coli* (FIG. 18A) and *S. aureus* (FIG. 18B) killing in the presence of increasing concentrations of the P(MAA-MBAA)-Cl nanoparticles. The growth curves of untreated bacteria or bacteria incubated with 1% P(MAA-MBAA) nanoparticles are also shown. These results represent the trend observed in at least three independent experiments.
Figure 18B:
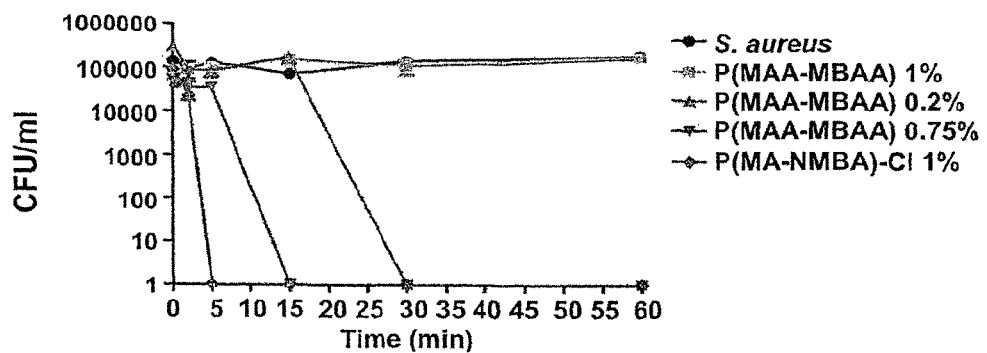

Antibacterial Properties of the P(MAA-MBAA)-Cl Nanoparticles:

The killing kinetics following incubation of either *E. coli* or *S. aureus* with increasing concentrations of the P(MAA-MBAA)-Cl nanoparticles, namely, 0.2%, 0.75%, and 1% (w/v), was monitored. Samples were collected at various time points of: 0, 2, 5, 15, 30, and 60 min. Although 0.2% P(MAA-MBAA)-Cl nanoparticles partially attenuated the growth of *E. coli* by 15' and complete elimination was obtained at 30' (FIG. 18A), full eradication was achieved for *S. aureus* at 30', and no effect was observed at 15' (FIG. 18B), suggesting that the P(MAA-MBAA)-Cl nanoparticles act more slowly on *S. aureus* than on *E. coli*. At a concentration of 0.75% P(MAA-MBAA)-Cl nanoparticles, both types of bacteria were completely killed at 15', demonstrating dose-dependent kinetics. Furthermore, at 1% P(MAA-MBAA)-Cl nanoparticles, no viable *E. coli* bacteria were detected after 2' (FIG. 18A) and no viable *S. aureus* after 5' (FIG. 18B), further demonstrating that *E. coli* have a higher susceptibility to the P(MAA-MBAA)-Cl nanoparticles than do *S. aureus*. In addition, non-chlorinated P(MAA-MBAA) nanoparticles was used at the same concentrations used for P(MAA-MBAA)-Cl nanoparticles as a negative control, but because these nanoparticles did not affect the bacterial growth at all applied concentrations, only the results for the highest concentration used, i.e., 1% P(MAA-MBAA) nanoparticles is presented.

Figure 19:
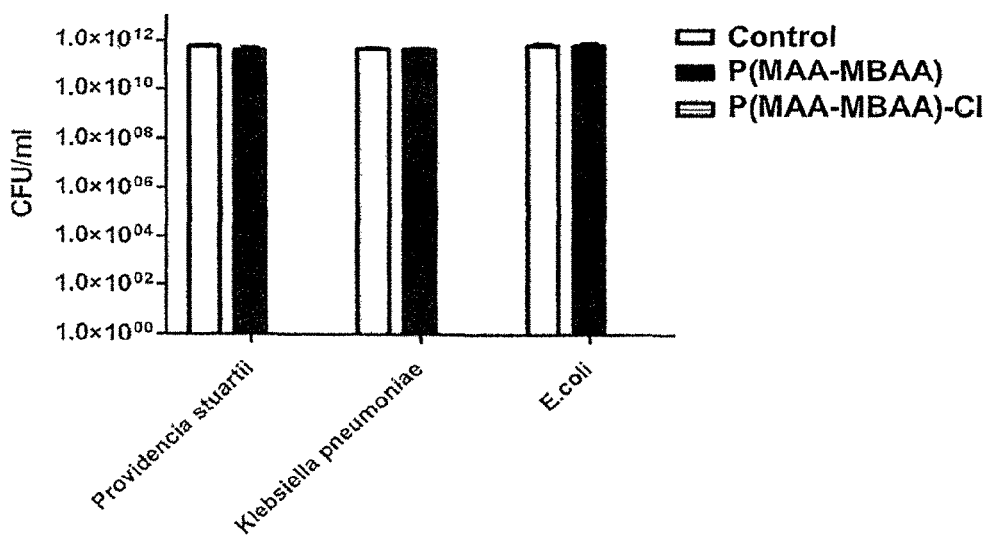
FIG. 19 presents a bar graph showing the antibacterial activity of P(MAA-MBAA)-Cl nanoparticles (0.6% w/v, 0.1 M Cl concentration) prepared as described in the experimental section against multiple drug resistance (MDR) bacterial strains of *Providencia stuartii*, *Klebsiella pneumonia*, and *E. coli*. The bacterial strains were grown overnight and treated as described in the Examples section.

Antibacterial Activity of the P(MAA-MBAA)-Cl Nanoparticles Against MDR Bacteria:

antibacterial activity of the P(MAA-MBAA)-Cl nanoparticles against MDR bacteria was tested, as described hereinabove. The bacterial strains chosen for this analysis were clinical isolates of *E. coli* 5327752 (resistant to Gentamicin and Ampicillin), *Klebsiella pneumoniae* 5363271 (resistant to Gentamicin, Ciprofloxacin, and Ampicillin), and *Providencia stuartii* 5327311 (resistant to Gentamicin, Ampicillin, and Colistin). These bacteria are highly resistant to many of the antibiotics available to date and thus pose a serious public health threat because they are more difficult to eradicate. As presented in FIG. 19, all three bacteria strains were completely killed following incubation with the P(MAA-MBAA)-Cl nanoparticles as opposed to those grown in the presence of the non-chlorinated nanoparticles or sterilized water. Taken together, these results suggest that P(MAA-MBAA)-Cl nanoparticles offer the potential to treat multidrug-resistant bacteria.

Figure 20A:
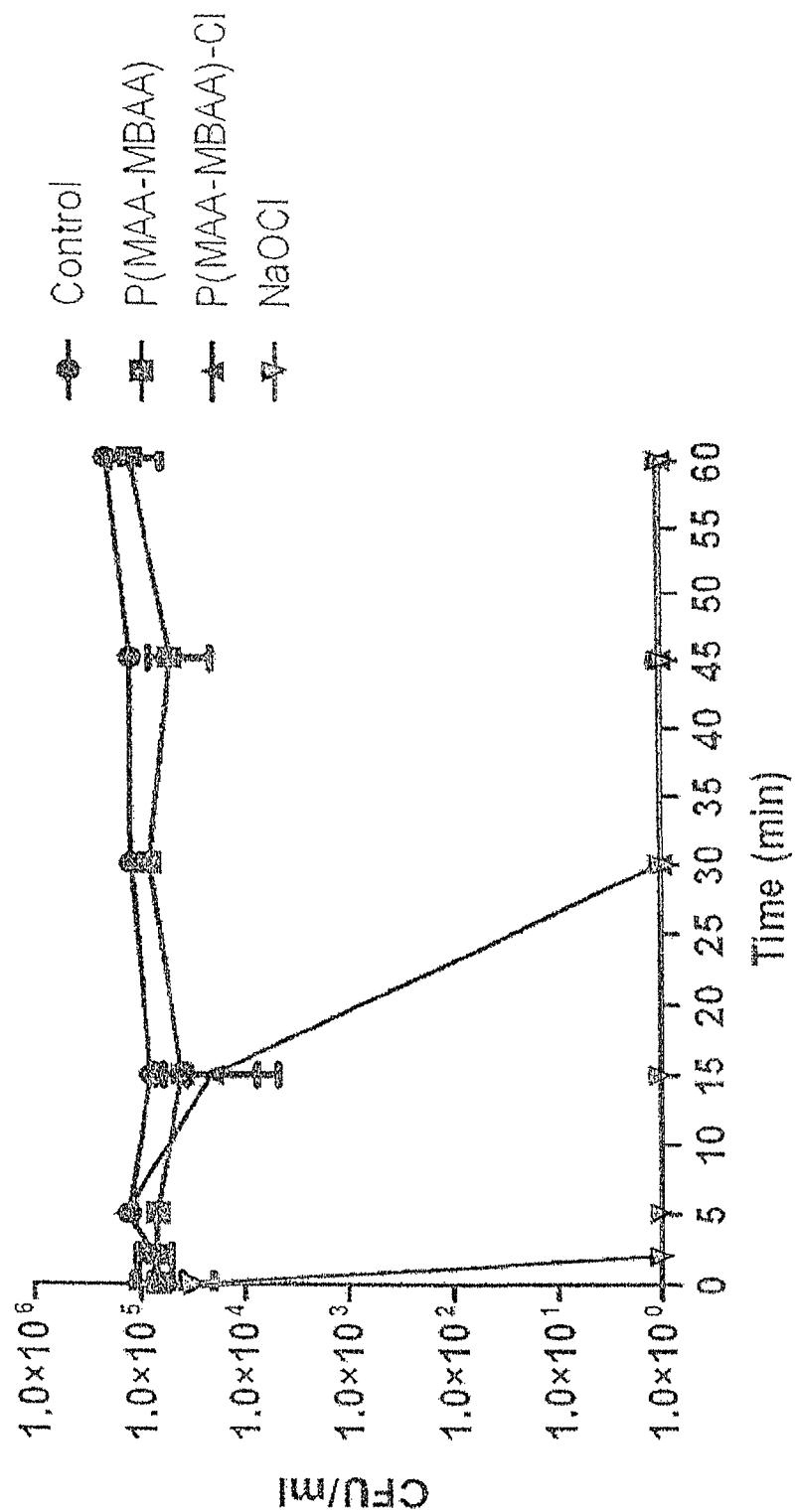
FIGS. 20A-B present graphs showing killing kinetic curves, as obtained from experiments being conducted at least three independent times, of *E. coli* (FIG. 20A) and *S. aureus* (FIG. 20B) in the presence of either P(MAA-MBAA)-Cl or NaOCl. The growth curves of untreated bacteria or bacteria incubated with P(MAA-MBAA) NPs are displayed as well.
Figure 20B:
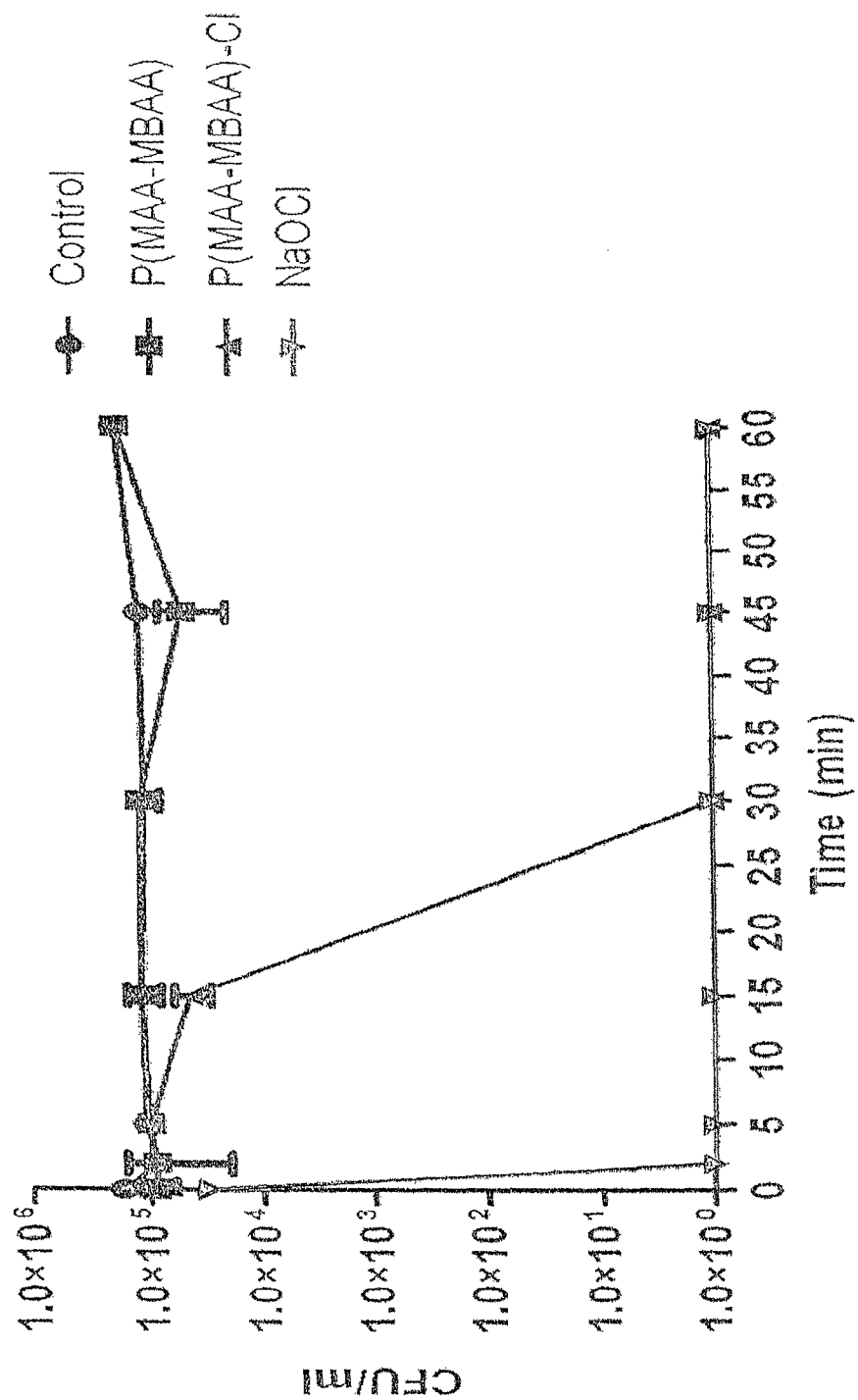

Bacterial Killing Kinetics in the Presence of P(MAA-MBAA)-Cl NPs and NaOCl:

The killing kinetics of P(MAA-MBAA)-Cl NPs and NaOCl reagents in the presence of *E. coli* (FIG. 20A) or *S. aureus* (FIG. 20B) were compared. In line with the observed differences in the oxidative chlorine release kinetics, NaOCl acted faster, eradicating both types of bacteria within 2 minutes of exposure, in comparison to the chlorinated NPs that eliminated the same amount of bacteria only after 30 minutes (FIG. 20). In summary, the data show that bleach exerts its antimicrobial activity faster than the NPs, however, in the long run P(MAA-MBAA)-Cl NPs exhibit superior stability and efficacy, especially under adverse environmental conditions that contain high organic load like proteinaceous materials. Therefore, P(MAA-MBAA)-Cl NPs should be the reagent of choice.

Figure 21:
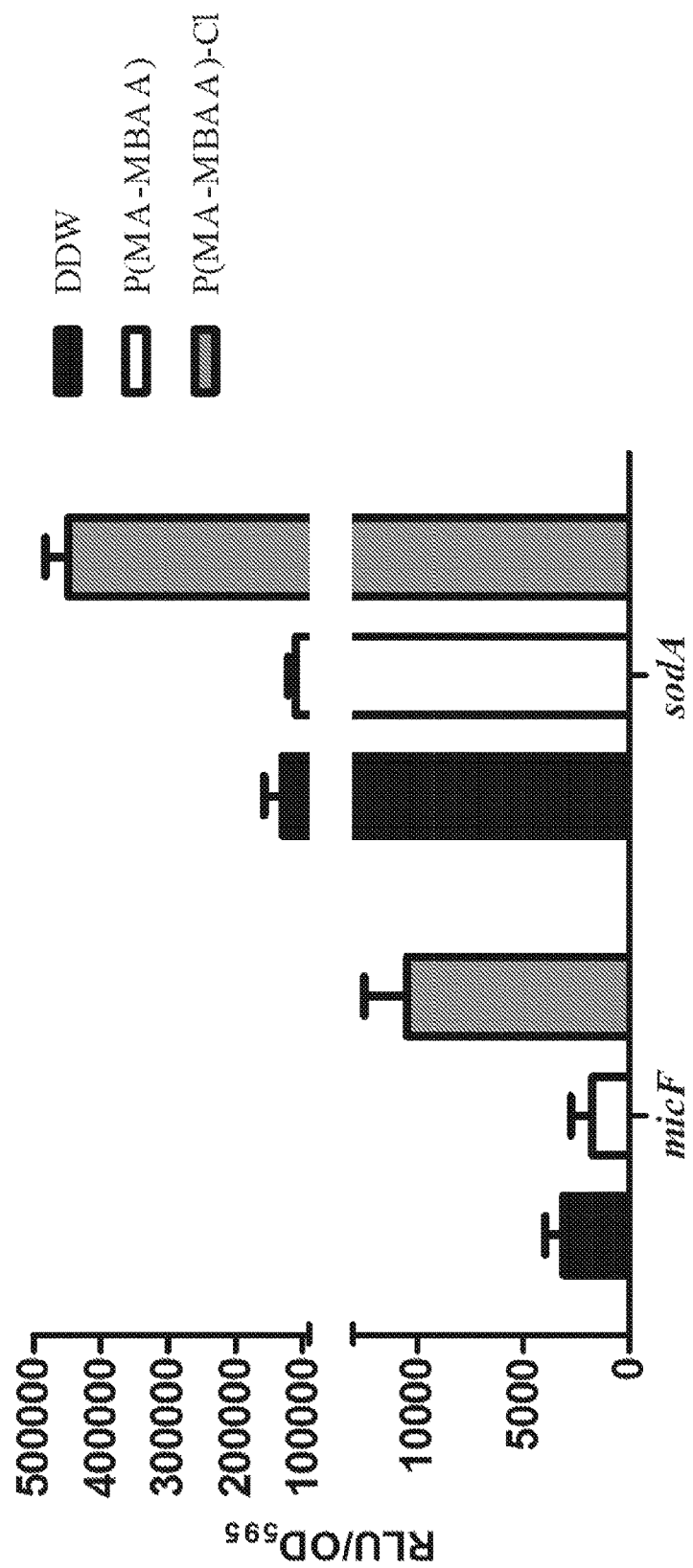
FIG. 21 presents a bar graph showing oxidative stress induced by P(MAA-MBAA)-Cl NPs. *E. coli* strains bearing a promoter-lux fusion for oxidative stress related genes, i.e., micF or sodA, were exposed to 5.5 mM oxidative chlorine found on the P(MAA-MBAA)-Cl NPs for 8 h. Bacteria treated with either sterile water or P(MAA-MBAA) NPs served as negative controls. Gene expression was monitored by measuring luminescence. The results are presented as relative luminescence unites (RLU) as a function of growth (OD595). Error bars correspond to the standard deviations of three independent experiments.

Biosensor Bacteria Screening Assay:

To understand better the mechanism whereby the P(MAA-MBAA)-Cl nano agents exert their toxic effects, biosensor *E. coli* bacteria created by Belkin and colleagues were utilized, as described hereinabove. The genetically-engineered bacteria harbor plasmid bioluminescence lux genes fused to specific stress response promoters, and thus can be exploited to monitor activation of stress responses, such as heat shock, DNA damage, oxidative stress, and fatty acid metabolism disruption. Of all the bacteria screened, only *E. coli* strains harboring a plasmid containing either micF::luxCDABE or sodA::luxCDABE fusion were significantly induced by the P(MAA-MBAA)-Cl NPs in comparison to bacteria treated with either water or non-chlorinated NPs (FIG. 21). It is important to note that this response was observed only when a lower dose (5.5 mM) of the chlorinated NPs was applied that was not high enough to induce massive cell death, but was sufficiently high to induce the bacterial defense pathways. sodA and micF are both responsive to oxidative stress and their induction by P(MAA-MBAA)-Cl NPs likely reflects the mechanism underlying bacterial killing. Superoxide dismutase (i.e., sodA) catalyses the transition of superoxide ($O^{2-}$) to oxygen and $H_2O_2$, and then catalase and peroxidase prevent the accumulation of $H_2O_2$ within the cell by converting it to $H_2O$ and $O2$. Accordingly, SodA is considered a key enzyme in *E. coli* oxidative stress response. The micF gene encodes a non-translated antisense RNA that binds the mRNA of the outer membrane porin protein (OmpF), triggering OmpF degradation and hence represents a negative regulator. OmpF forms pores at the outer cell membrane, allowing the passive diffusion of small hydrophilic molecules across the membrane.[35] Regulation of outer membrane permeability critically influences survival of the bacteria in response to environmental stress. Indeed, various environmental factors have been shown to be involved in MicF-mediated reduction of OmpF levels, such as oxidative stress, nutrients depletion and increased osmolarity.

Figure 22A:
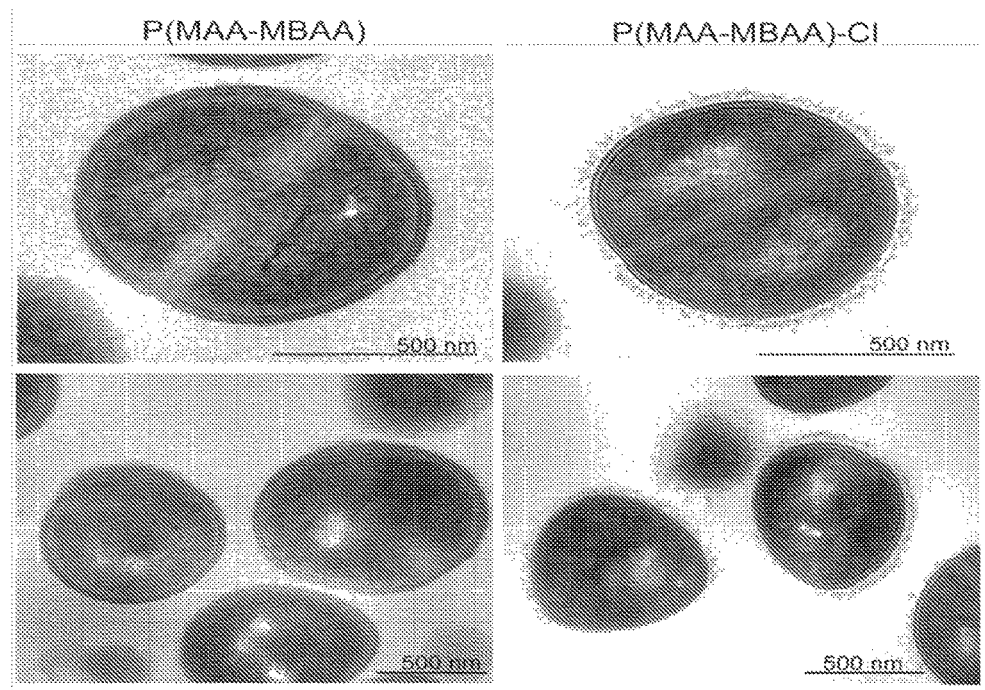
FIGS. 22A-B presents transmission electron microscopy (TEM) images of *S. aureus* bacteria. *S. aureus* were treated with either P(MAA-MBAA) NPs (left panels) or their chlorinated counterparts (right panels) for 1.5 h (FIG. 22A), and TEM micrographs of *S. aureus* treated with the P(MAA-MBAA)-Cl NPs for 15' (FIG. 22B). Bar is 500 nm.
Figure 22B:
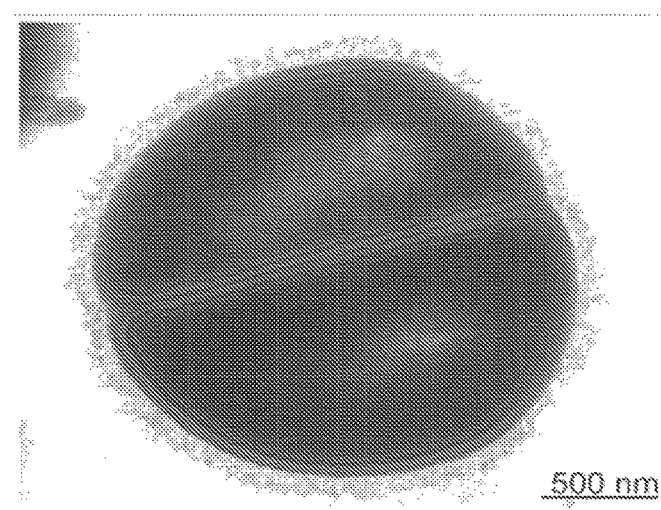

TEM Examination:

To investigate in more detail the mechanisms underlying the antibacterial activity of P(MAA-MBAA)-Cl NPs, transmission electron microscopy (TEM) was conducted to examine if the NPs exert morphological effects on the bacteria. We did not observe any detectable morphological changes within *S. aureus* bacteria following treatment with the chlorinated NPs for 1.5 h (FIG. 22), which corresponds to the time needed to kill $10^9$ CFU/ml of these bacteria (data not shown). However, we did observe the formation of very organized structures of particles around the bacteria, specifically accumulating at the cell wall and encircling it like "necklaces" (FIG. 22A). Remarkably, these particles were not observed in the extracellular space, suggesting a specific interaction of these particles with the bacteria. Of note, these layers of particles did not surround cells treated with distilled water (data not shown) or non-chlorinated NPs (FIG. 22A), suggesting that the oxidative chlorine on the NPs is responsible for this unusual phenomenon. Moreover, the particles decorated the bacteria already at 15', revealing not only a specific interaction with the bacterial cells, but also a rapid one (FIG. 22B). The proportion of cells marked with these particles was quantified and found that 100% of the cells exhibited these structures after only 15' (n=300), although some cells were encircled with less particles than others.

Figure 16:
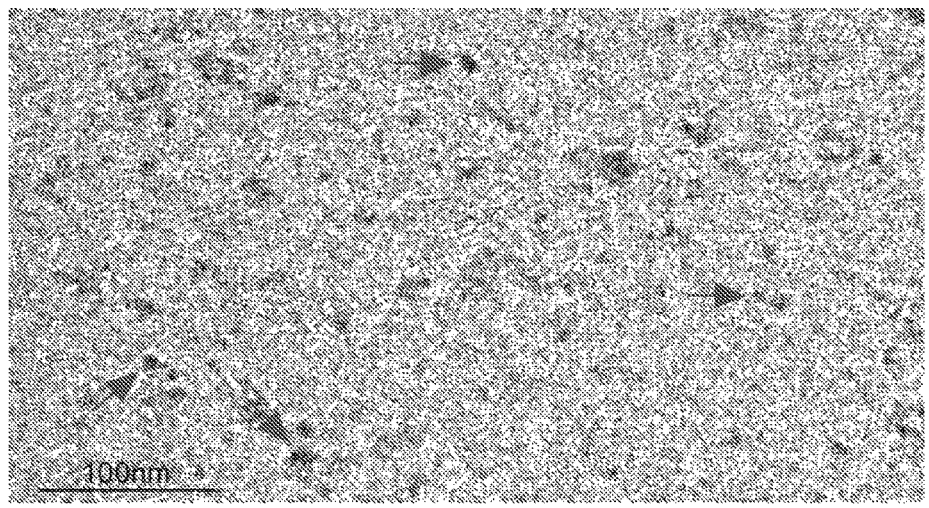
FIG. 16 presents cryo-transmission electron microscopy (TEM) image of the P(MAA-MBAA)-Cl NPs, with arrows marking the NPs, as prepared according to some embodiments of the present invention. Bar is 100 nm.
Figure 23A:
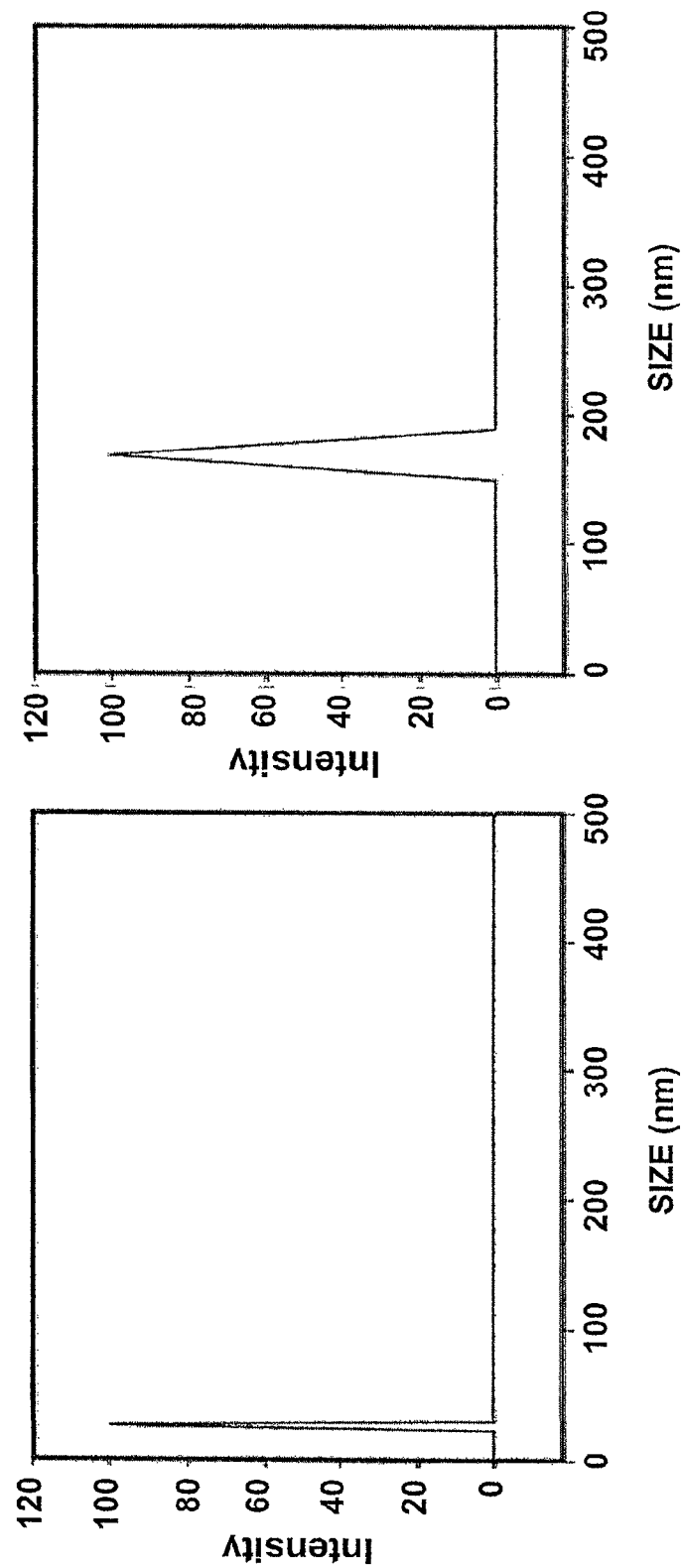
FIGS. 23A-C present hydrodynamic size histogram (FIG. 23A) and the corresponding cryo-TEM images of the P(MAA-MBAA)-Cl NPs synthesized at two different sizes i.e., small (left panels) and large (right panels) (FIG. 23B; bar is 200 nm), and TEM micrographs of *S. aureus* bacteria treated for 1.5 h with the chlorinated NPs of the two different sizes (FIG. 23C).
Figure 23B:
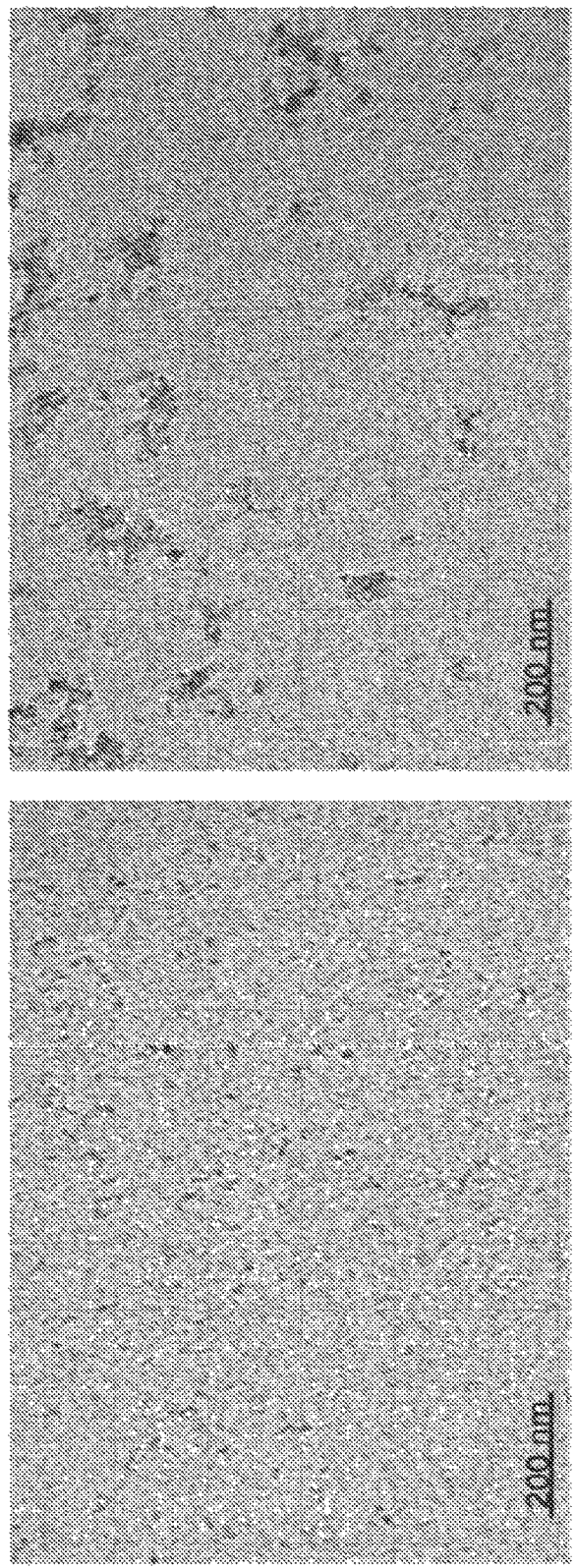
Figure 23C:
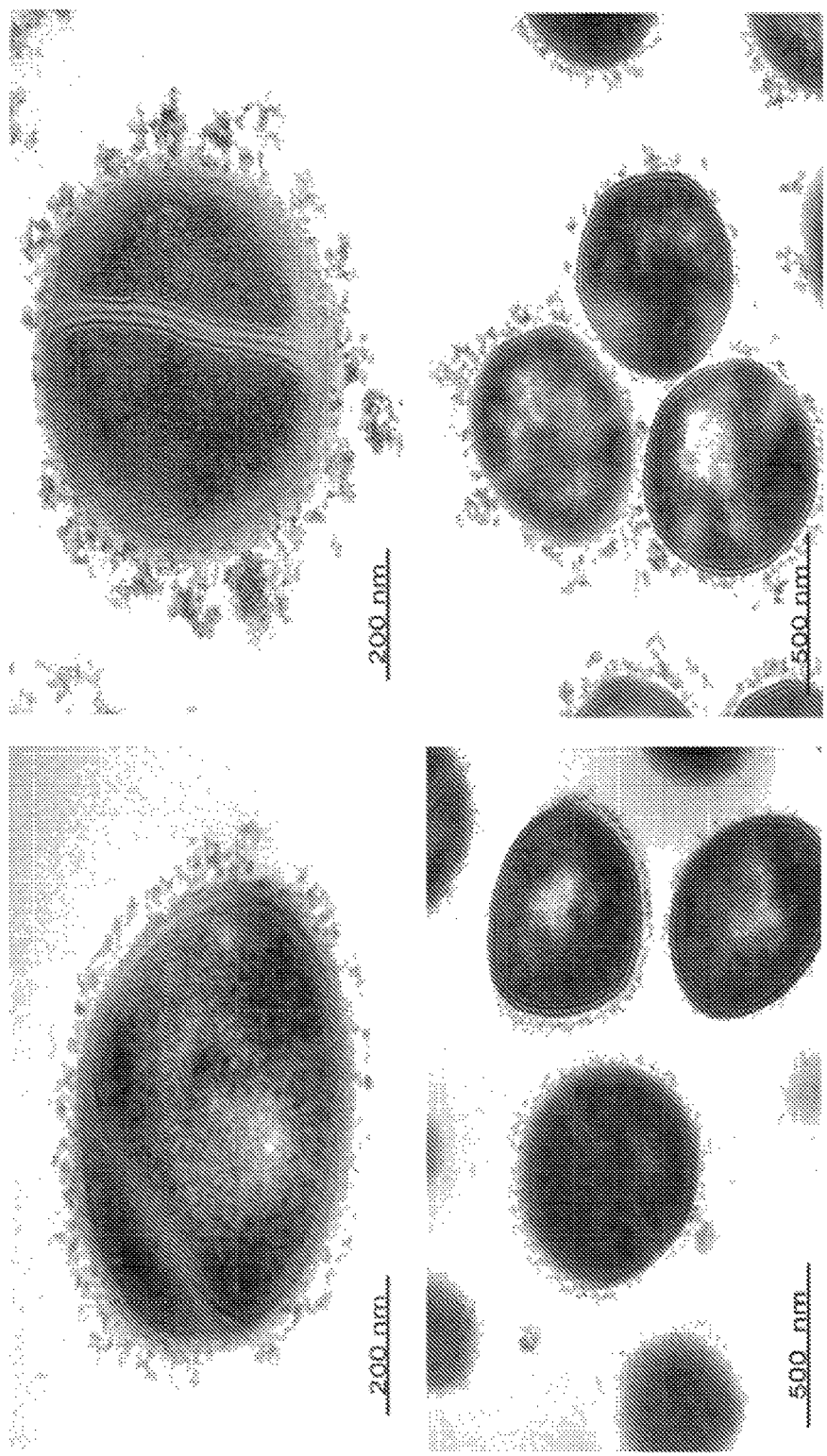
Figure 24:
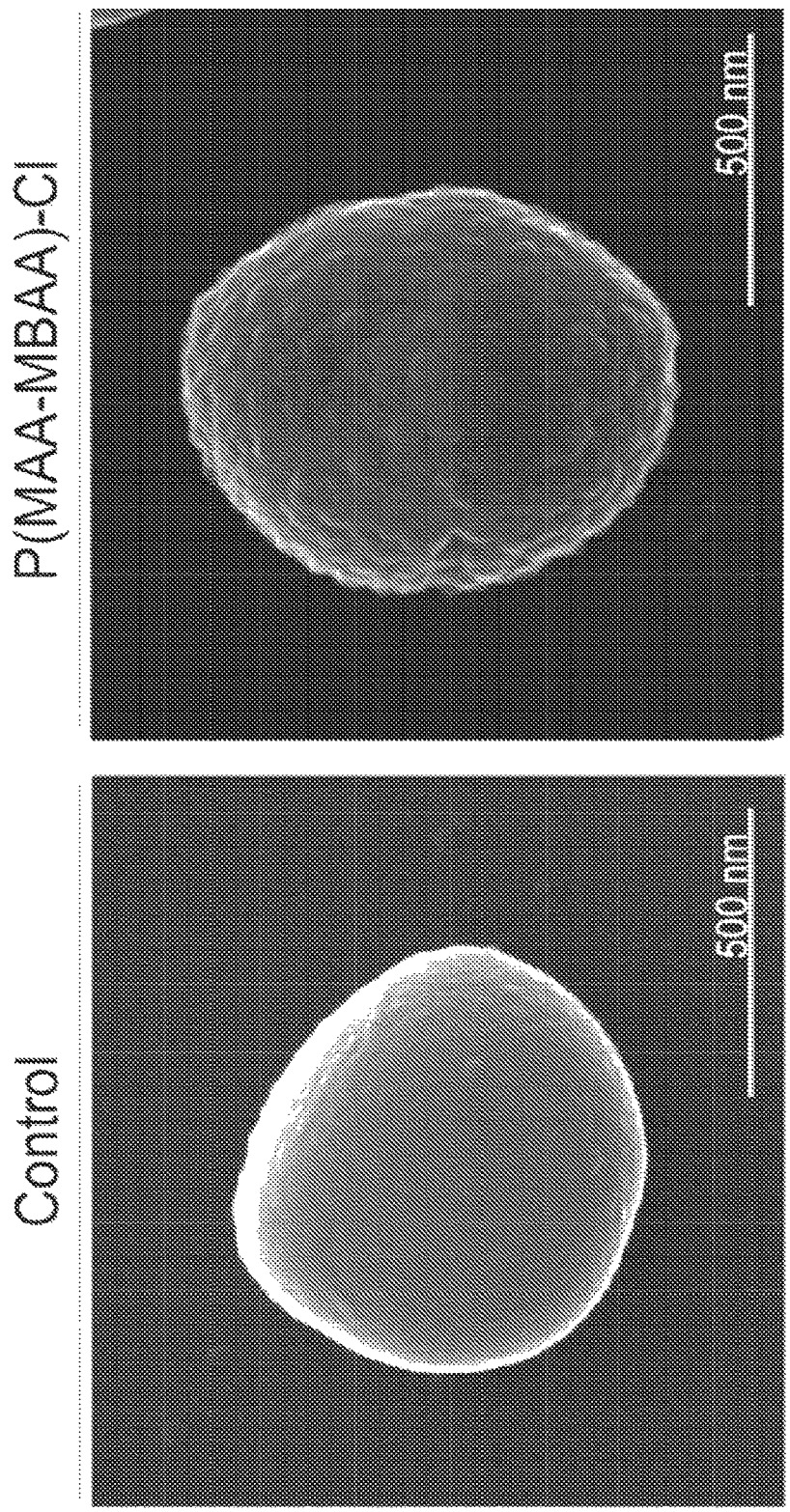
FIG. 24 presents scanning electron microscopy (SEM) of *S. aureus* bacteria treated with P(MAA-MBAA)-Cl NPs for 1.5 h (right panel) vis-a-vis untreated *S. aureus* bacteria (left panel).
Figure 25:
FIG. 25 presents TEM micrographs of *E. coli* bacteria treated with either P(MAA-MBAA) NPs (left panel) or their chlorinated counterparts for 45' (right panel). Bar is 500 nm.

Without being bound by any particular theory, one interpretation of the data is that these particles are the P(MAA-MBAA)-Cl NPs themselves. Another option is that cellular material is secreted by the bacteria due to the stress imposed by the chlorinated NPs, although the latter is less likely due to the rapid appearance of the particles on the cell surface. To differentiate between these options, NPs 6 times larger than those utilized hereinthroughout were synthesized, i.e., 190±20 nm as opposed to 27±3 nm hydrodynamic diameter according to dynamic light scattering (DLS) measurements (FIG. 23A). As described hereinabove, the cryo-TEM images presented in FIGS. 16 and 23B illustrate the difference in dry size; the small NPs are about 3-15 nm while the large NPs are mostly aggregates of 100-200 nm. As presented in FIG. 23C, bacteria treated with the larger NPs were indeed surrounded by larger particles, the size of which matched the TEM measurements of NPs alone (FIG. 23B). Notably, although the larger P(MAA-MBAA)-Cl NPs associated mainly with the bacterial cells, there were some aggregates in the extracellular environment unlike the observations of the small NPs, which were only observed surrounding the bacteria. This finding suggests that the small NPs may be more target specific and therefore, superior for bacterial killing. These data support the model that the chlorinated NPs specifically interact with the bacteria via oxidative chlorine release and inflict toxic effects on the bacteria that are trapped within these nanocages. These nanocaging was further illustrated via SEM images that show the NPs' 3D morphology (FIG. 24). These data suggest that chlorinated NPs have a uniquely strong tendency to adhere and circle the bacterial cell wall rather than aggregate. Moreover, the observation that every bacterium was marked with chlorinated NPs, further emphasizes their potency as an anti-bacterial agent. Of note, no pronounced appearance of NPs around *E. coli* was detected (FIG. 25), which could be explained by the different cell wall composition of Gram-negative versus Gram-positive bacteria.

Figure 26:
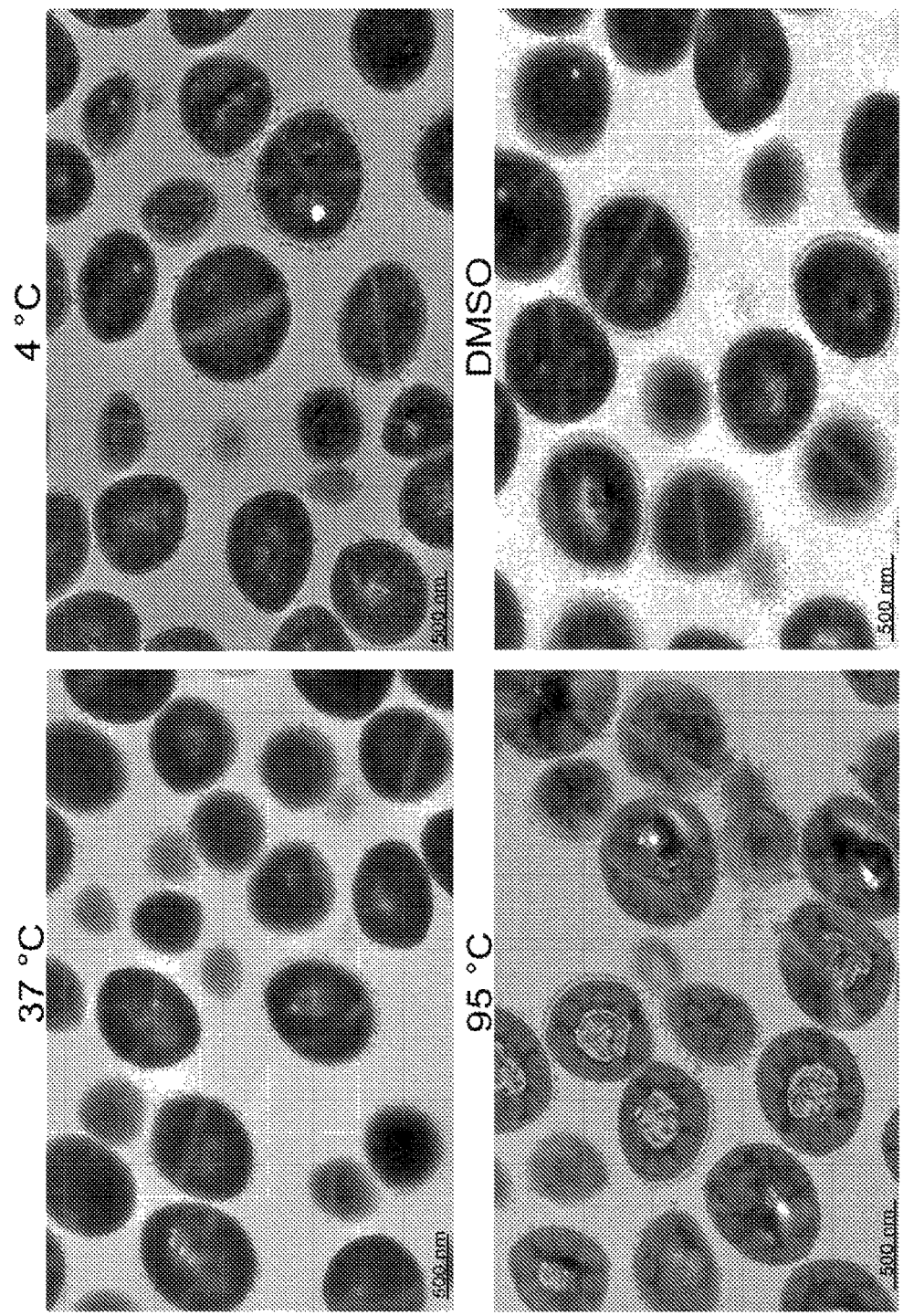
FIG. 26 presents transmission electron microscopy (TEM) images of *S. aureus* bacteria treated with P(MAA-MBAA)-Cl NPs for 15'. The upper two panels show *S. aureus* that were incubated with the chlorinated NPs for 15' at 37° C. (left panel) or at 4° C. (right panel) (following pre-incubation of the cells for 2 hours at 4° C.). The lower panels show *S. aureus* that were either boiled for 10' at 95° C. (left panel) or incubated with DMSO for 1 h before adding the NPs for 15' (right panel). Bar is 500 nm.
Figure 27:
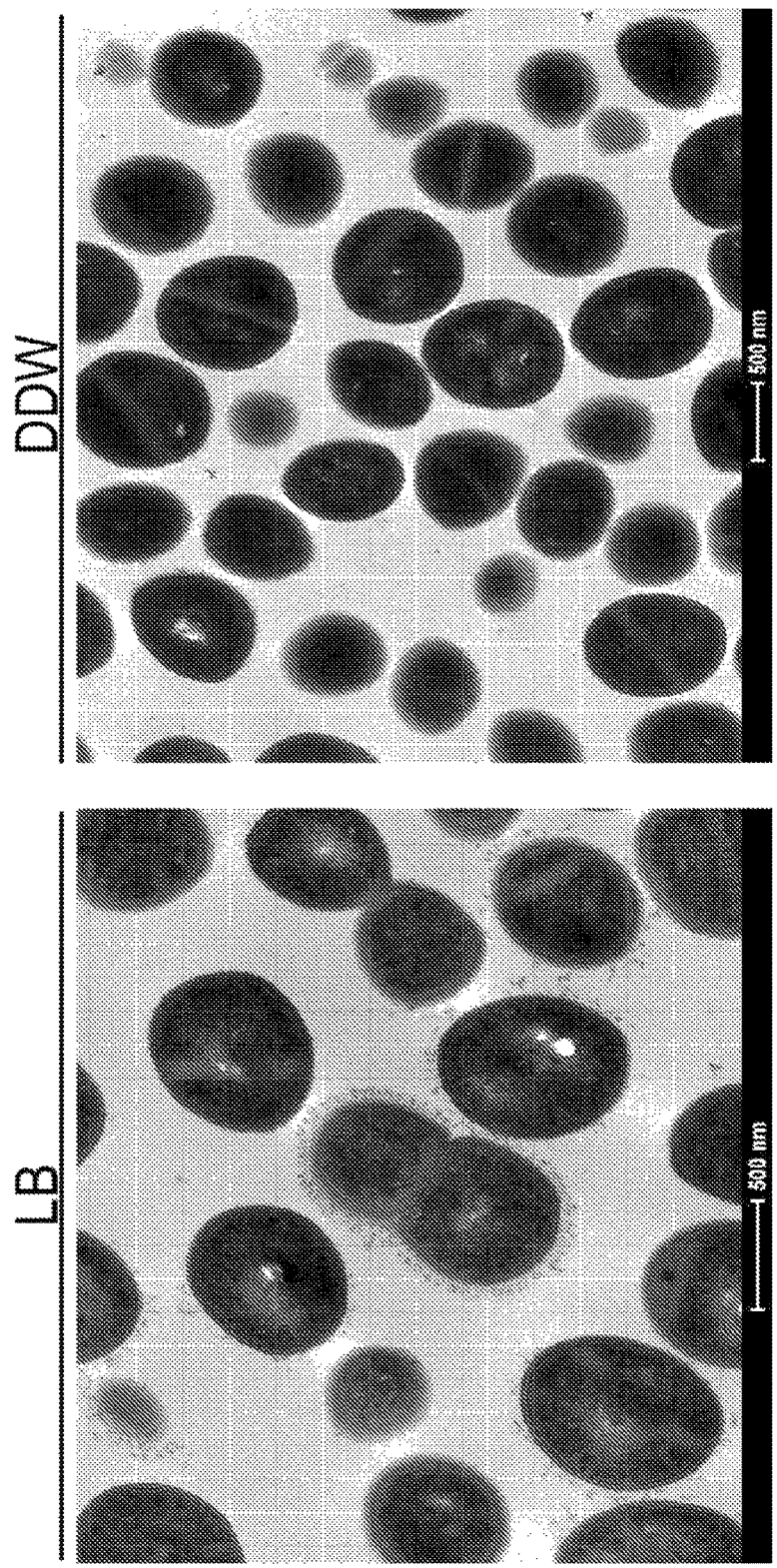
FIG. 27 presents TEM micrographs of *S. aureus* suspended in LB (left panel) or DDW (right panel) followed by the addition of P(MAA-MBAA)-Cl NPs for 15'. Bar is 500 nm.

To determine if the gathering of the chlorinated NPs at the cell wall of S. aureus requires energy, the cells were either pre-incubated at 4° C. for 2 h or thermally killed (i.e. boiled for 10 minutes) before adding the NPs. As shown in FIG. 26, inactivating the metabolic state of S. aureus or killing it did not abrogate the formation of the structures around the cells, suggesting neither energy nor cellular proteins/enzymes are required for this interaction to occur. Moreover, using the antioxidant DMSO did not abolish the bacterial decoration by the P(MAA-MBAA)-Cl NPs, suggesting ROS formation is not a prerequisite for this tagging either (FIG. 26). Nevertheless, when the NPs were mixed with bacteria suspended in water, the cells were barley marked with the particles (FIG. 27), which may imply that some component/s found in LB is mediating the interaction between the bacteria and the NPs. Of importance, the zeta potential of the NPs becomes positive when LB is added to the particles' suspension, i.e. 1.59 mV (as opposed to the negative value received from the suspension itself). This may suggest that the attraction of the NPs to the bacteria is favored when LB is added due to the positively charged NPs that are now attracted to the negatively charged bacterial surface.

Figure 28:
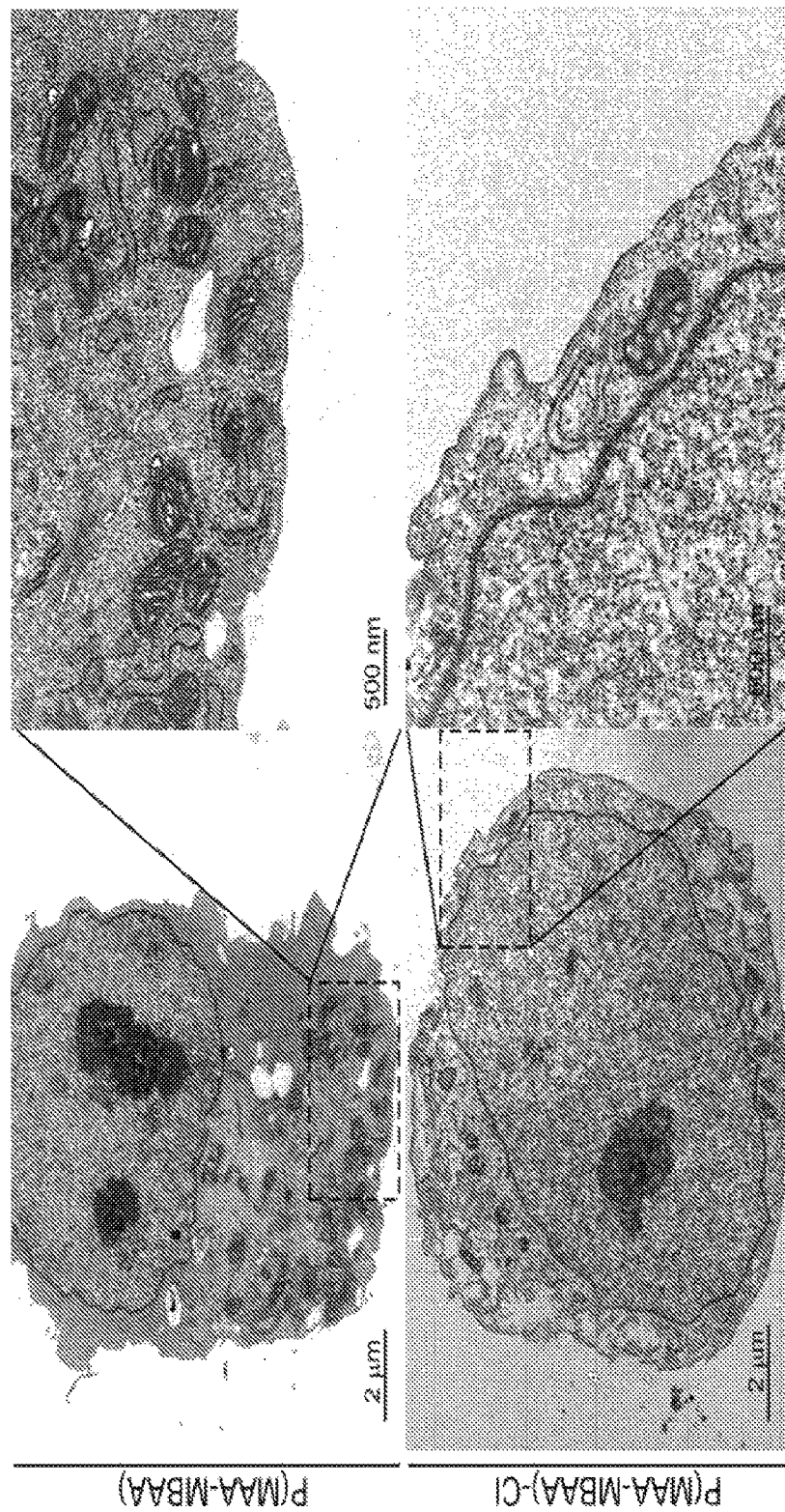
FIG. 28 presents transmission electron microscopy of Saos-2 cells treated with either P(MAA-MBAA) NPs (upper panel) or their chlorinated counterparts (lower panel) for 15'. The pictures show that there is no specific accumulation of NPs on the cell surface. In the left panels bar is 2 µm; in the right panels the bar is 500 nm.

Targeting Mammalian Cells:

In additional exemplary procedures, the ability of the charged NPs to target mammalian cells was examined, using the osteosarcoma cell line Saos-2. As can be seen in FIG. 28, no particles were observed around the Saos-2 cells, whether the P(MAA-MBAA) or the P(MAA-MBAA)-Cl NPs were applied. It is concluded that S. aureus bacteria are specifically marked for destruction by the chlorinated NPs, which unload their oxidative Cl cargo and eliminate the bacteria.

Figure 29:
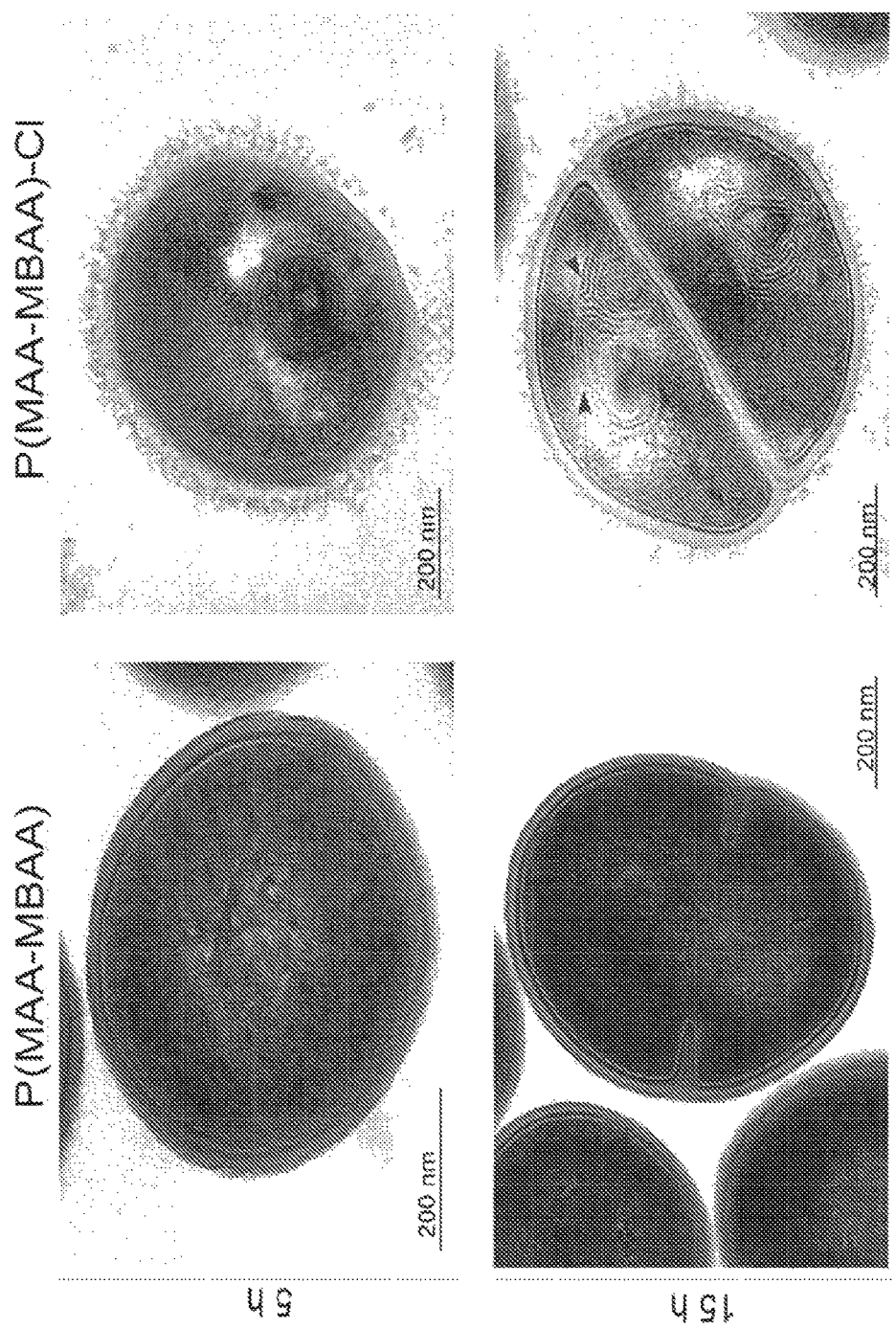
FIG. 29 presents TEM images showing P(MAA-MBAA)-Cl NPs triggering morphological changes within the bacteria. S. aureus were treated with either P(MAA-MBAA) NPs (left panel) or chlorinated counterparts (right panel) for 5 h (upper panel) or 15 h (lower panel). The arrows designate membrane constructs. Bar is 200 nm.

Since there were no noticeable morphological changes following incubation with P(MAA-MBAA)-Cl NPs for 1.5 h, the incubation was extended to 5 h and 15 h. After 5 h and 15 h of incubation with the chlorinated nanosized agents, membrane 'snail-like' structures were observed to accumulate within the S. aureus cells, (FIG. 29). This phenomenon was not detected within cells treated with non-chlorinated NPs (FIG. 29) or distilled water (data not shown), suggesting that the oxidative chlorine provoked directly or indirectly the formation of these tightly packed intracellular membrane structures.

Example 7

Examination of P(MAA-MBAA)-Cl NPs in Organic Media

Methods

Determining the Stability of the P(MAA-MBAA)-Cl NPs and NaOCl in Organic Rich Media:

1 ml of either DDW, NaOCl or P(MAA-MBAA)-Cl NPs was mixed with 1 ml of twofold concentrated LB medium and incubated for 3 h, 5 h or 24 h. Then, E. coli or S. aureus were added to each of the solutions, reaching a final concentration of $10^5$ CFU/ml and the mixture agitated for either 3 h or 24 h. At the indicated time points, samples were taken for cell viability determination and the solutions were reloaded with freshly prepared bacteria. The experiment was continued until the reagents were no longer capable of evincing toxic effects on the tested bacteria.

Kinetics of Oxidative Chlorine Release from the Charged NPs and NaOCl in the Presence of Organic Rich Media:

Equal volumes of NaOCl or P(MAA-MBAA)-Cl NPs were incubated with equivalent volumes of twofold concentrated LB medium. The precise concentration of the oxidative chlorine found on the two reagents was determined at different time intervals via quenching with sodium iodide followed by spectrophotometer (Amersham Bioschiences) measurements at wavelengths of 292 nm and 350 nm, as previously described.

Kinetics of Oxidative Chlorine Release from the Charged NPs and NaOCl in the Presence of Organic Rich Media:

Equal volumes of NaOCl or P(MAA-MBAA)-Cl NPs were incubated with equivalent volumes of twofold concentrated LB medium. The precise concentration of the oxidative chlorine found on the two reagents was determined at different time intervals via quenching with sodium iodide followed by spectrophotometer (Amersham Bioschiences) measurements at wavelengths of 292 nm and 350 nm.

ESR Measurements:

ROS production was detected using the ESR spin trapping technique coupled with a spin trap 5,5-Dimethyl-pyrroline N-oxide (DMPO, Sigma, St. Louis, Mo.). Typically, the aqueous suspensions of NPs were added to DMPO (0.01 M), in the presence of equivalent volumes of either twofold concentrated LB medium, or each of its components (Tryptone, yeast extract, NaCl) or water. Whenever indicated the following antioxidants were added to the reaction: 10% DMSO, 10 mM N-acetyl cycteine (NAC) and 10 mM Ascorbic acid (AA), all were purchased from Sigma. The solution was drawn into a 0.8 mm ID capillary quartz tube sealed at both ends with a plastic Critoseal (Thermo Fisher Scientific Inc), which was placed into a quartz tube that in turn was placed into the EPR rectangular cavity (ER 4122SHQ). The measurements were taken using a X-band Elexsys E500 EPR spectrometer (Bruker, Karlsruhe, Germany) using the following parameters: microwave power, 20 mW; scan width, 100 G; resolution, 1024; Gain, 60; sweep time, 60 s; # scans, 2; modulation frequency, 100 kHz; modulation amplitude, 1 G. In order to compare the radical intensity, the double integration (DI) of the spin adduct signal was calculated, using the Xepr 2.6b.58 acquisition version.

Results

Figures 30A, 30B:
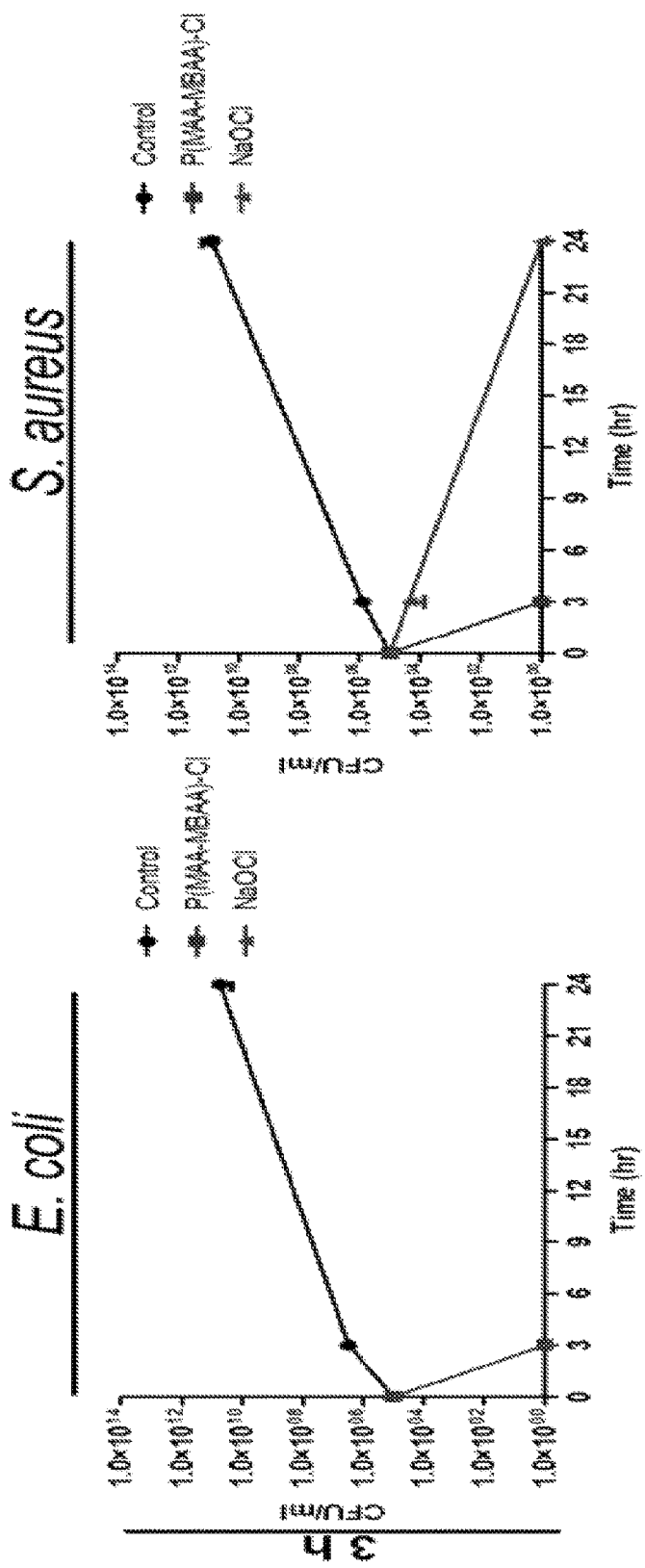
FIGS. 30A-F present graphs demonstrating the short-term stability of P(MAA-MBAA)-Cl NPs versus NaOCl to organic material. E. coli (FIGS. 30A, 30C, 30E) or S. aureus (FIGS. 30B, 30D, 30F) were added to LB media that had been pre-incubated with either P(MAA-MBAA)-Cl NPs, NaOCl, or left untreated for 3 h (FIGS. 30A-B), 5 h (FIGS. 30C-D) or 24 h (FIGS. 30E-F). Aliquots were removed after a further 3 h or 24 h incubation and plated on agar plates to determine bacterial viability. Error bars indicate the standard deviation of three independent experiments.
Figures 30C, 30D:
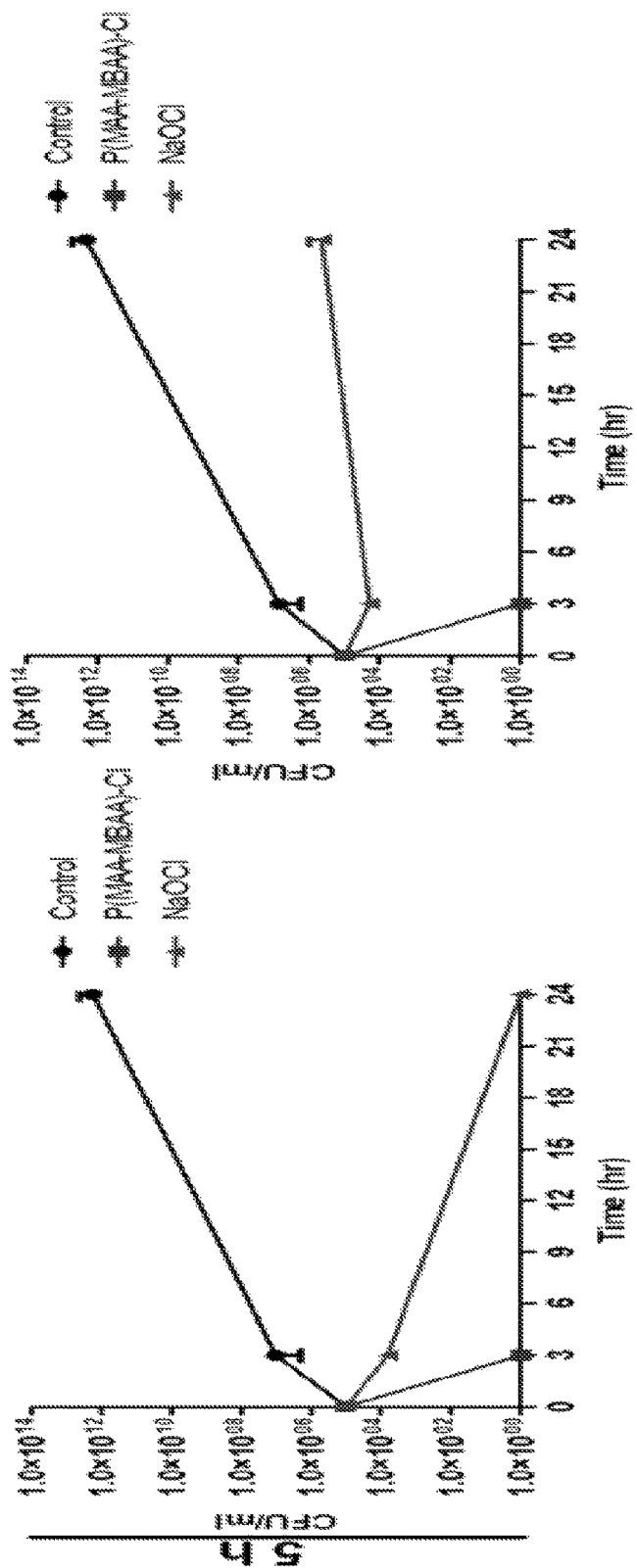
Figures 30E, 30F:
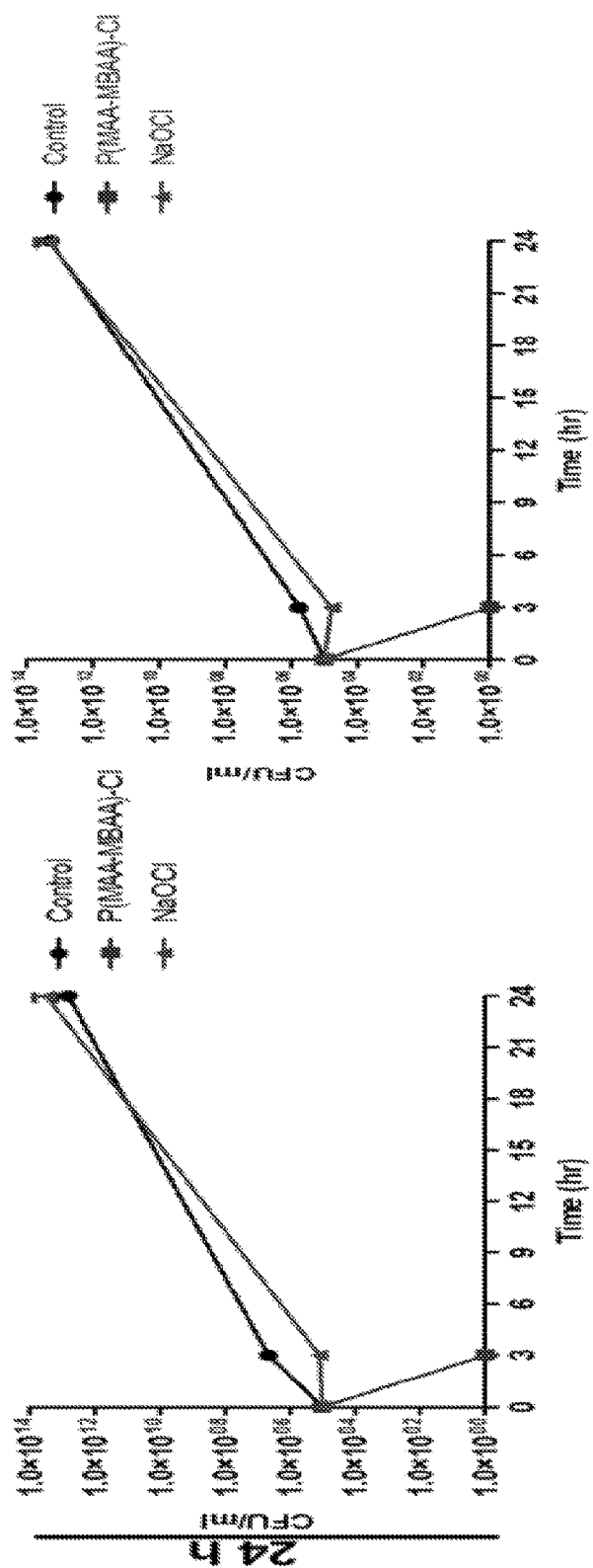

The stability of chlorinated NPs versus bleach in full organic media (i.e. LB) was compared. As described hereinabove, under "Methods", P(MAA-MBAA)-Cl NPs and NaOCl were pre-incubated with LB for different periods: 3 h, 5 h or 24 h. After this initial incubation with organic media, E. coli or S. aureus bacteria were supplemented to a final concentration of $10^5$ CFU/ml, and samples were taken after a further 3 h or 24 h of incubation. As shown in FIG. 30A, pre-incubation of NaOCl or chlorinated NPs with LB for 3 h prior to addition of E. coli had no impact on their bactericidal activity. However, pre-incubation of NaOCl with media for 3 h prior to addition of S. aureus did compromise its bactericidal activity, as the reagent was subsequently only capable of evincing complete killing by 24 hours (FIG. 30B). In contrast, pre-incubation of P(MAA-MBAA)-Cl NPs with media for 3 h prior to addition of S. aureus had no impact on its bactericidal activity, with complete killing observed after 3 h (FIG. 30B). Pre-incubation of NaOCl with media for 5 h prior to addition of E. coli resulted in growth inhibition at the 3 h time point, with bacteria viability reduced by almost 4 logs; complete killing was evident only at 24 h (FIG. 30C). The same conditions elicited growth arrest for S. aureus (FIG. 30D), further corroborating our premise that E. coli are more sensitive to bleach than S. aureus. Remarkably, pre-incubation of P(MAA-MBAA)-Cl NPs with LB for 5 h prior to addition of *E. coli* or *S. aureus* did not compromise its bactericidal activity (FIGS. 30C-D). Finally, pre-incubation of NaOCl with LB for 24 h prior to addition of *E. coli* or *S. aureus* destroyed its antibacterial activity, such that the bacteria grew comparably to untreated controls (FIGS. 30E-F). In sharp contrast, pre-incubation of P(MAA-MBAA)-Cl with LB for 24 h prior to addition of *E. coli* or *S. aureus* did not compromise its bactericidal activity (FIG. 30E-F). In summary, P(MAA-MBAA)-Cl NPs exhibit superior stability to organic materials as compared to bleach.

Figure 31A:
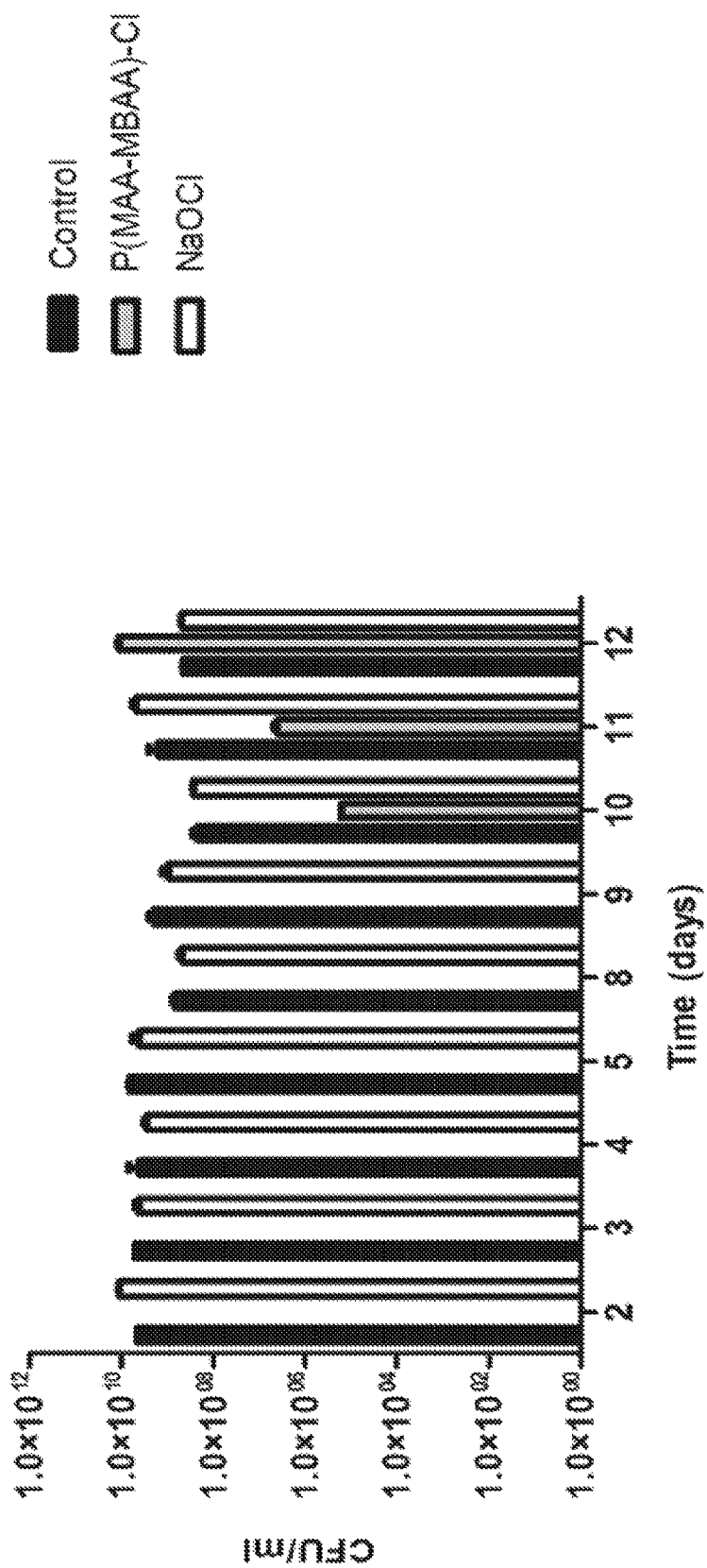
FIGS. 31A-B present bar graphs showing P(MAA-MBAA)-Cl NPs exhibiting long-term activity and stability to organic materials. E. coli (FIG. 31A) or S. aureus (FIG. 31B) were treated with either P(MAA-MBAA)-Cl NPs, NaOCl, or were untreated. Each of these reagents was pre-incubated with LB medium for 24 h (day 1) following which 10^5 CFU/ml of the relevant bacteria were added for 24 h (day 2). Every day aliquots were removed from each sample and plated on agar plates. In parallel, 10^5 CFU/ml fresh bacteria were added as appropriate. Error bars represent the standard deviation of three independent experiments.
Figure 31B:
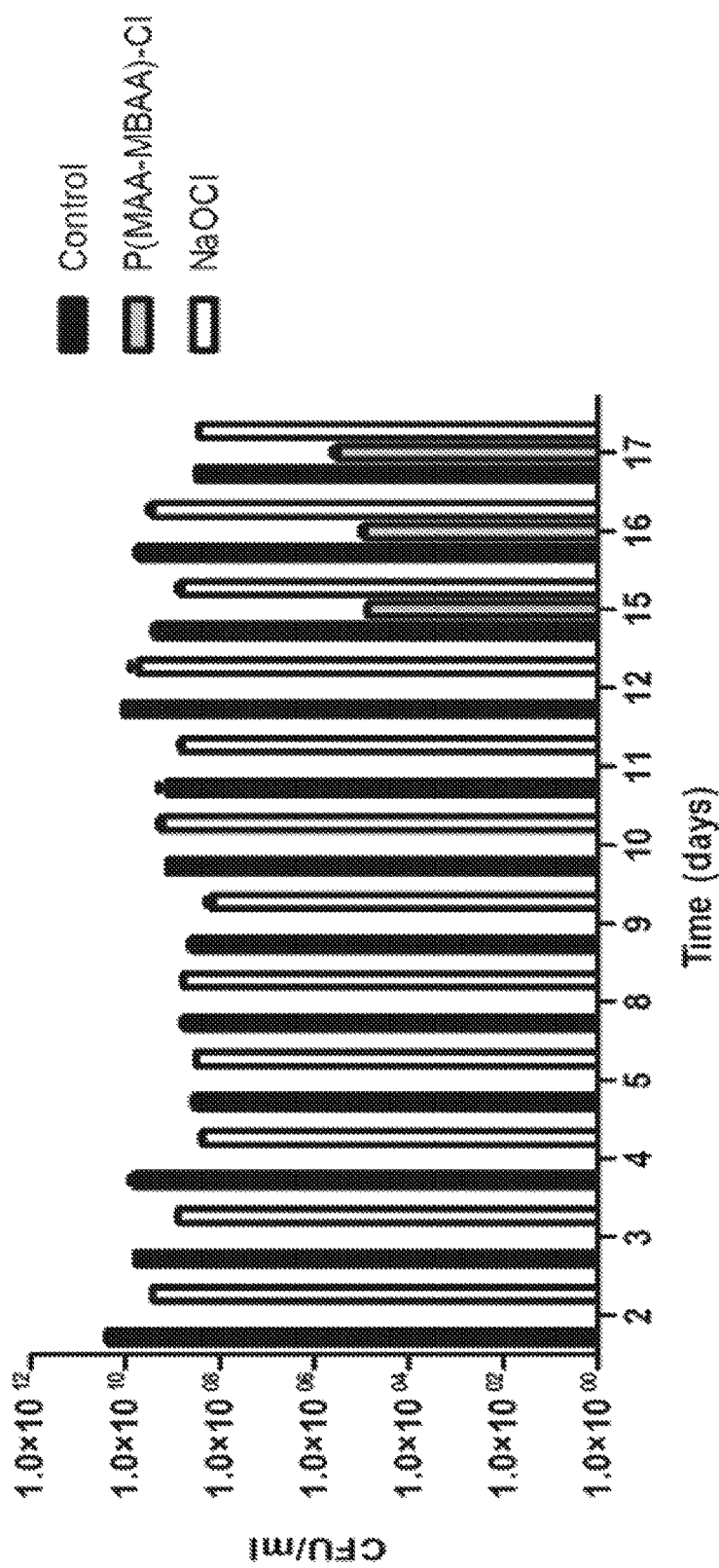
Figure 32:
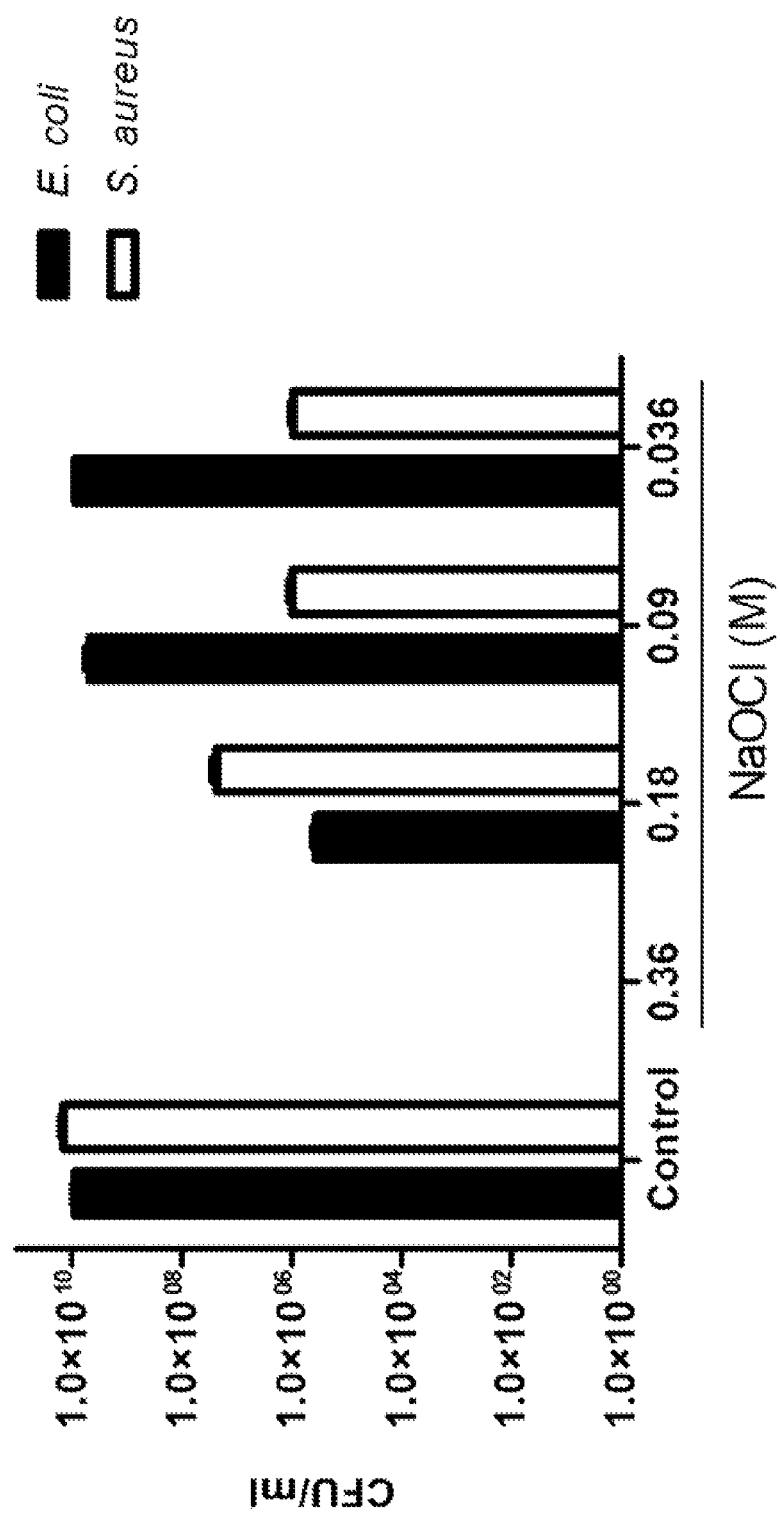
FIG. 32 is a bar graph showing the susceptibility of NaOCl to organic materials. Fresh NaOCl solution, taken from a commercial container (0.72 M), was incubated with an equivalent volume of LB (reaching a final concentration of 0.36 M) for 1 week before addition of either E. coli or S. aureus. Lower concentrations of NaOCl subjected to the same procedure are also presented.

Having established that chlorinated NPs are still toxic towards bacteria despite pre-exposure to organic rich media for 24 h, the longer-term activity of P(MAA-MBAA)-Cl NPs was examined. To this end, P(MAA-MBAA)-Cl NPs were exposed to repetitive bacterial loading cycles for up to 17 days. The chlorinated NPs retained bactericidal activity over 6 loading cycles of *E. coli* spread over 9 days, but by the seventh cycle (on the tenth day) bacterial growth was only partially attenuated, and by the ninth loading cycle (day 12) the *E. coli* grew comparably to untreated controls (FIG. 31A). As for *S. aureus*, the chlorinated NPs continued killing the bacteria for nine consecutive cycles spread over 12 days, with bacterial growth only detectable on the following cycle (FIG. 31B). Taken together, the data demonstrate that nanosized P(MAA-MBAA)-Cl are more stable than NaOCl when exposed to organic materials. It was of interest to check at which concentration NaOCl retained the capability to kill bacteria, when the NaOCl was pre-incubated for 1 week with LB media. To address this, we took a sample of fresh NaOCl straight from a commercial bottle, corresponding to 0.72 M, incubated it with LB medium for 1 week and then added bacteria. Interestingly, it was found that 0.36 M of NaOCl, which is 33 times more than the concentration of the oxidative Cl bound to the NPs, is required to kill *E. coli* and *S. aureus*, with 0.18 M NaOCl ineffective (FIG. 32). This finding underscores the advantages of using chlorinated NPs over NaOCl, both in terms of stability and efficacy.

Figure 33A:
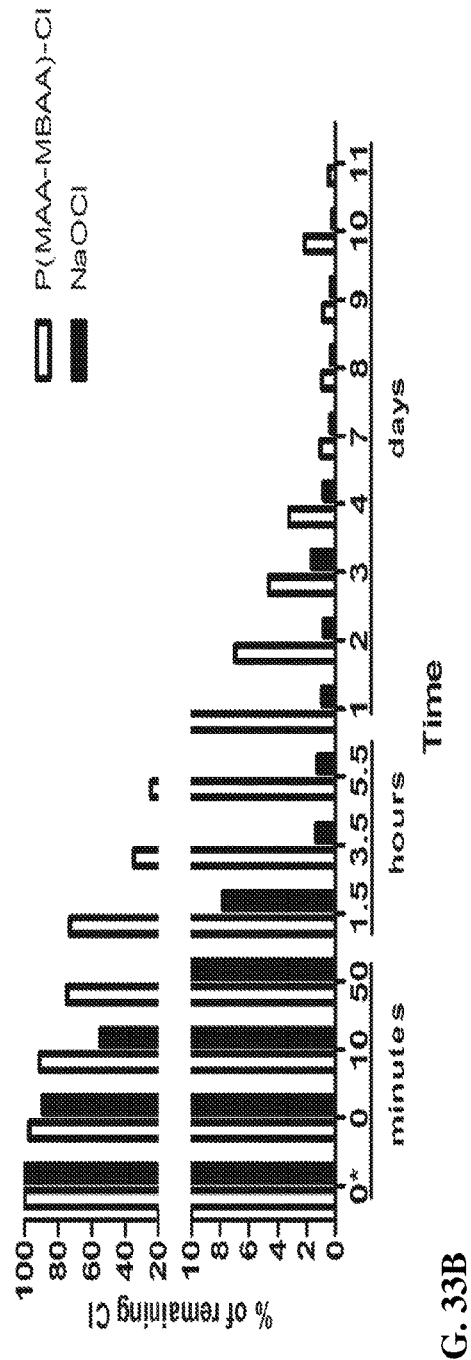
FIGS. 33A-B are bar graphs demonstrating the kinetics of oxidative chlorine release from P(MAA-MBAA)-Cl NPs and NaOCl. Chlorinated NPs and NaOCl were incubated with LB medium and at the stated time points, samples were taken for oxidative chlorine quenching via NaI. The oxidative chlorine concentrations were determined by spectrophotometer measurements at 292 nm (FIG. 33A) and 350 nm (FIG. 33B). 0* refers to the initial oxidative chlorine concentration found on either the NPs or NaOCl in water, i.e., prior to addition of the organic medium.
Figure 33B:
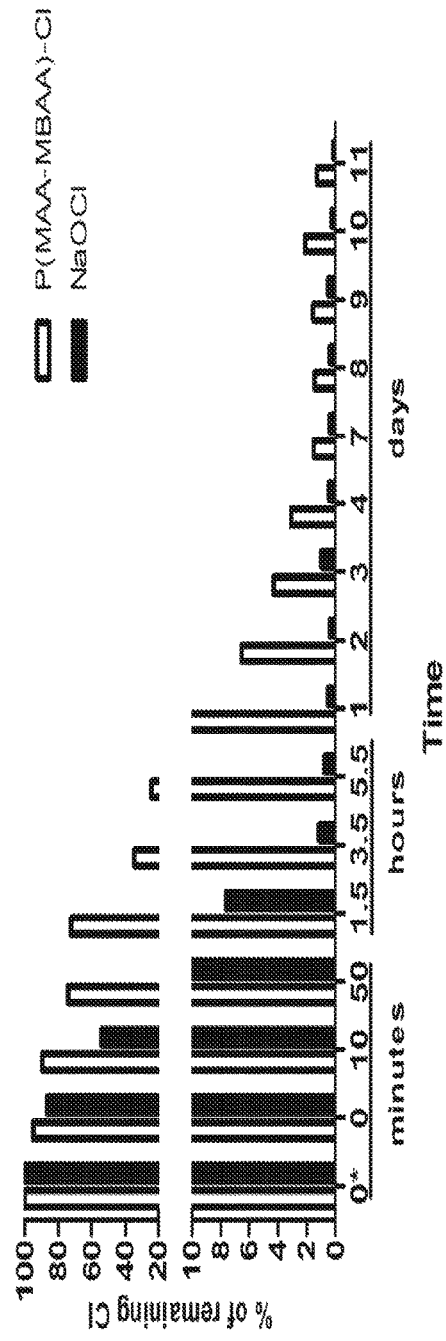
Figure 34:
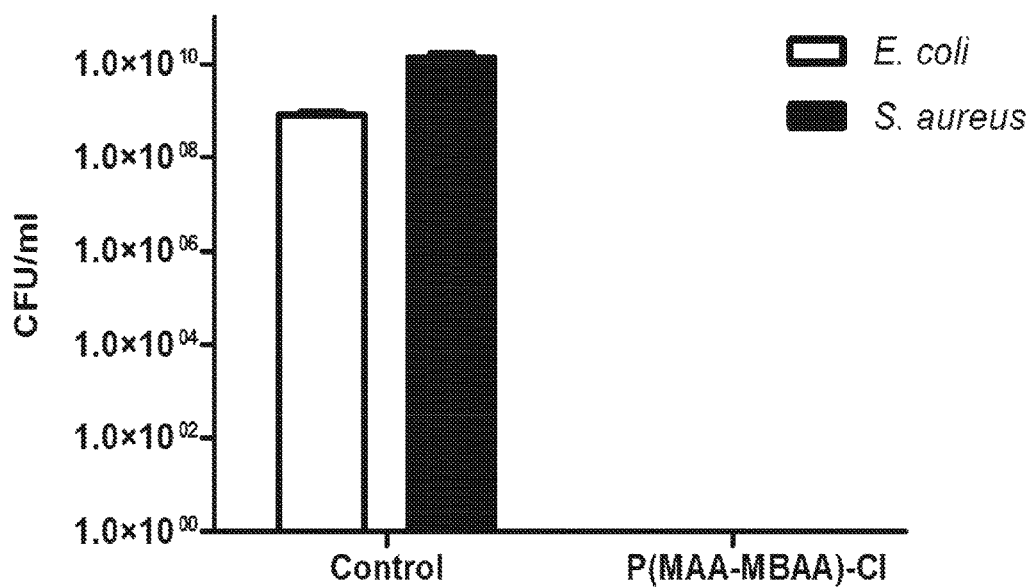
FIG. 34 is a bar graph showing that P(MAA-MBAA)-Cl NPs do not need to enter the bacteria to exert their killing effect. The chlorinated NPs or DDW (i.e. control) were incubated with LB medium for 10 minutes followed by centrifugation in ultrafiltration tubes (M.W cutoff 30000) that do not allow the NPs to pass through the pores, as determined by DLS. The filtrate was then supplemented with either E. coli or S. aureus.

To investigate in more detail the stability of P(MAA-MBAA)-Cl NPs, the oxidative chlorine content of the chlorinated NPs versus bleach after incubation in LB medium for 11 days was measured. The oxidative chlorine concentration was determined using a spectrophotometer at 292 nm (FIG. 33A) and 350 nm (Figure FIG. 33B). A surge in NaOCl consumption upon exposure to LB was observed, as the oxidative Cl release from NaOCl was very rapid, with almost 50% of the NaOCl molecules sequestered by organic substances after only 10 minutes of incubation in the medium (FIG. 33). In contrast, approximately 90% of the NPs retained their chlorinated form, suggesting a gradual decay of the $Cl^+$ from the NPs as opposed to the rapid decay observed for NaOCl. Still, this amount of released $Cl^+$ was sufficient to induce bacterial killing even following separation of the loaded NPs as presented in FIG. 34. Furthermore, after 1 day of incubation we could barely detect $Cl^+$ on NaOCl, with 0.9% and 0.5% chlorinated according to measurements at 292 nm and 350 nm, respectively (FIG. 33), whereas 12% of NPs retained $Cl^+$. Taken together, the data indicate that the organic materials in the medium scavenge the $Cl^+$ in NaOCl, compromising its activity and rendering bleach unable to kill bacteria. However, chlorinated NPs are far more stable, resist the scavenging nature of the organic material and hence, exhibit extended antibacterial activity under these conditions.

Figure 35:
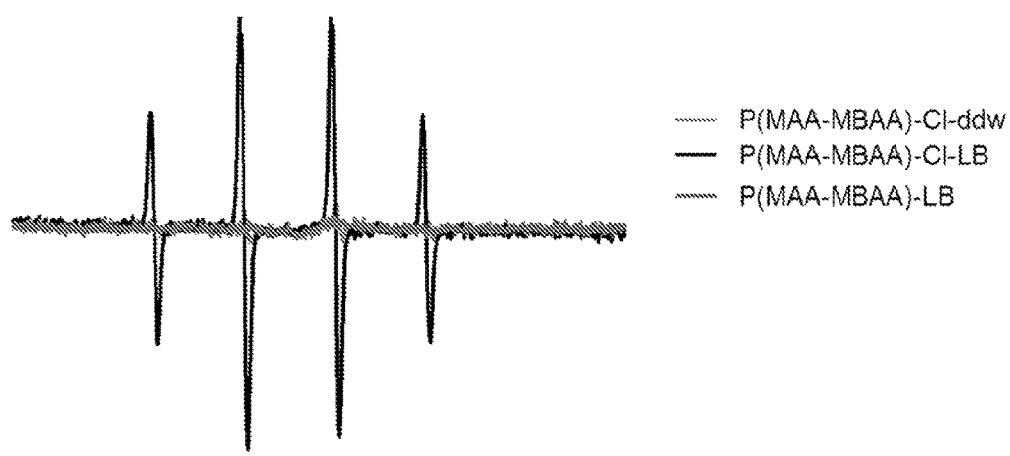
FIG. 35 presents graphs showing electron spin resonance (ESR) spectra demonstrating that P(MAA-MBAA)-Cl NPs provoke formation of hydroxyl radicals. ESR spectrum of the DMPO-OH adducts formed upon mixing P(MAA-MBAA)-Cl NPs with LB medium (black line) or distilled water (grey line). The blue line represents P(MAA-MBAA) NPs mixed with LB media.
Figure 36A:
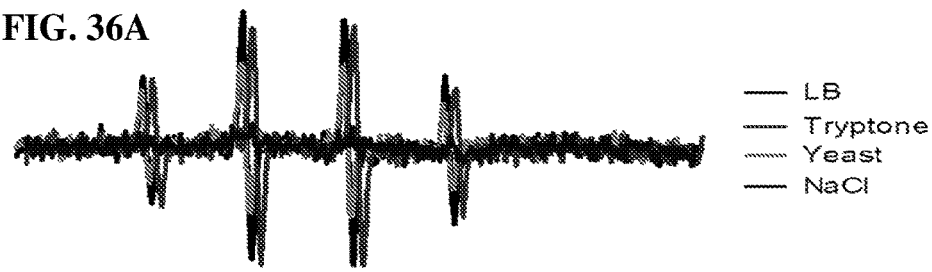
FIGS. 36A-B are graphs demonstrating that P(MAA-MBAA)-Cl NPs trigger formation of hydroxyl radicals in the presence of organic materials.
Figure 36B:
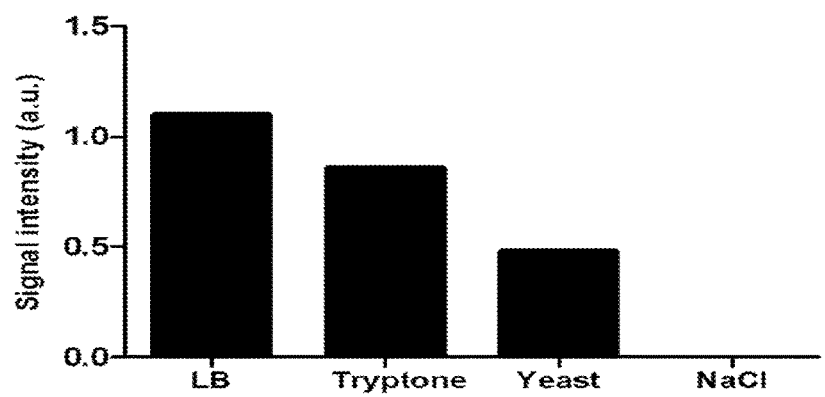
Figure 37:
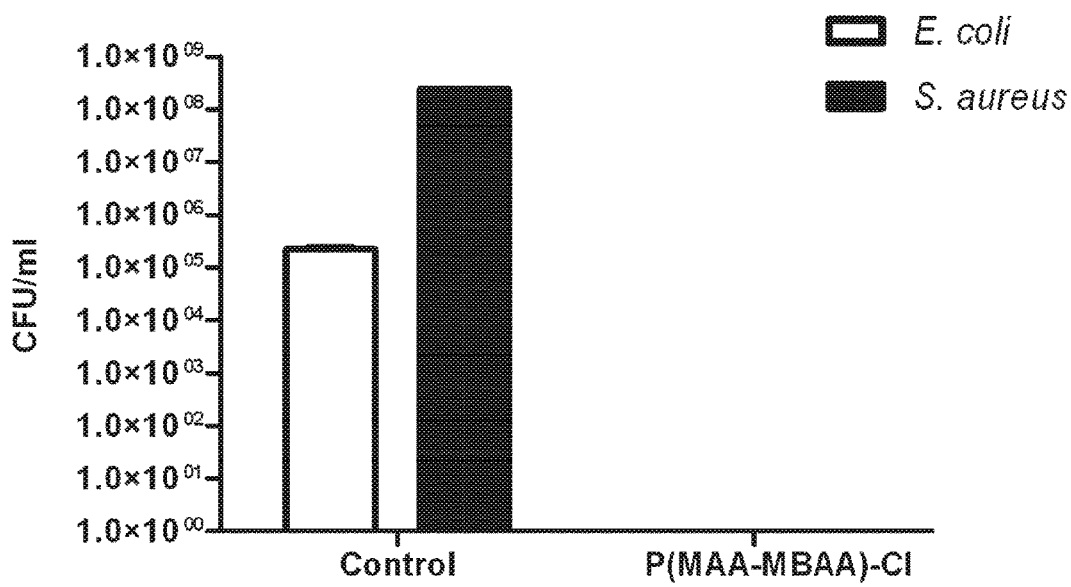
FIG. 37 is a graph demonstrating the killing effect of P(MAA-MBAA)-Cl NPs toward bacteria (E. coli and S. aureus) suspended in water. E. coli or S. aureus were incubated overnight with either DDW (i.e. control) or the chlorinated NPs following which samples were taken and plated on agar plates for determining the bacterial viability.

ESR Measurements:

In view of the oxidative activation of the two reporter strains as described hereinabove, ESR measurements were carried out to determine directly whether the chlorinated NPs generate Reactive Oxygen Species (ROS), using 5,5-dimethyl-1-pyrroline-N-oxide (DMPO) to trap oxygen-centered free radicals. The DMPO spin trap reacts with ROS, such as, hydroxyl radicals or superoxide anion radicals, to produce the spin adducts DMPO-OH or DMPOOH, respectively. The DMPO-OH is a relatively stable paramagnetic species with a characteristic EPR signal of 1:2:2:1 quartet. It was observed a typical ESR spectrum of DMPO-OH, giving rise to four resolved picks (FIG. 35), suggesting the formation of hydroxyl radicals (.OH). Of note, these radicals were formed only following exposure of the nano-sized P(MAA-MBAA)-Cl to organic reagents like LB media, and not when the chlorinated NPs were suspended in water (FIG. 35), revealing a target-specific mode of action. To further elucidate with what components in the LB medium the chlorinated NPs interact with to generate the hydroxyl radicals, each of the materials found within this growth medium (i.e. Tryptone, yeast extract and NaCl) was exposed to the P(MAA-MBAA)-Cl NPs. Only the Tryptone and the yeast extract triggered ROS formation by the NPs as opposed to NaCl which did not interact with the particles (FIG. 36), emphasizing the specificity of the charged NPs towards organic materials. This remarkable specificity is not exhibited by NaOCl. Without being bound by any particular theory, it is assumed that the ROS are generated directly or indirectly by the oxidative chlorine attached to the NPs, since non-chlorinated NPs did not provoke the formation of hydroxyl radicals (FIG. 35). It is important to note that the charged NPs are capable of killing bacteria suspended in water (FIG. 37), as the chlorinated NPs can exert toxicity via a direct transfer of the oxidative chlorine to a bacterial associated component.

Figure 38A:
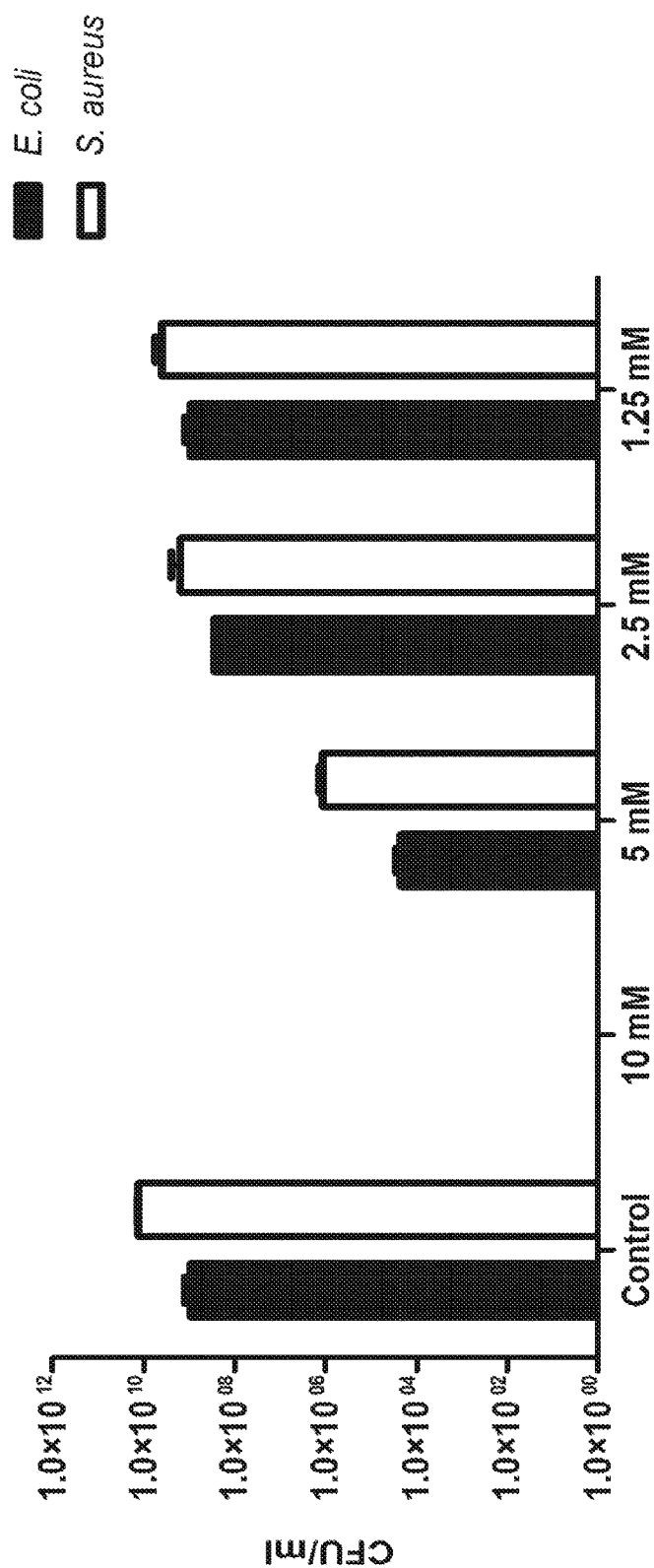
FIGS. 38A-C present graphs demonstrating that antibacterial activity of P(MAA-MBAA)-Cl NPs is proportional to the quantity of the radicals formed. CFU/ml of E. coli and S. aureus exposed to 1.25-10 mM of P(MAA-MBAA)-Cl NPs or to distilled water (negative control) for 24 h at 37° C.
Figure 38B:
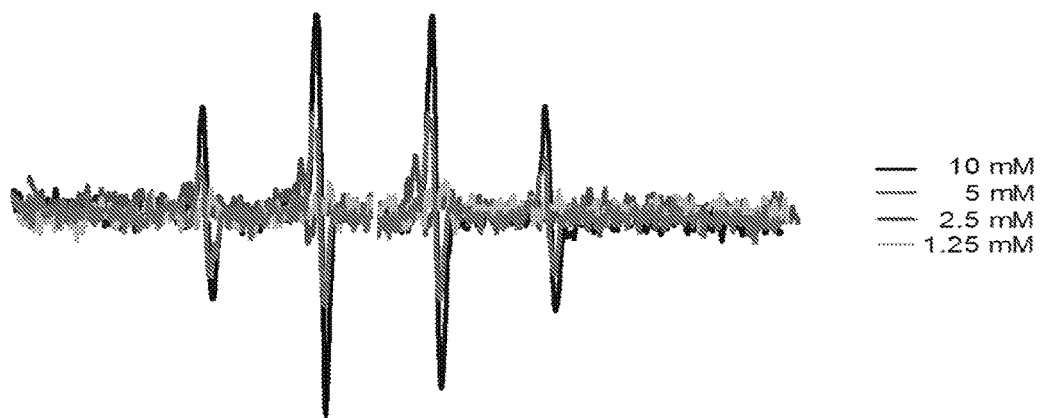
Figure 38C:
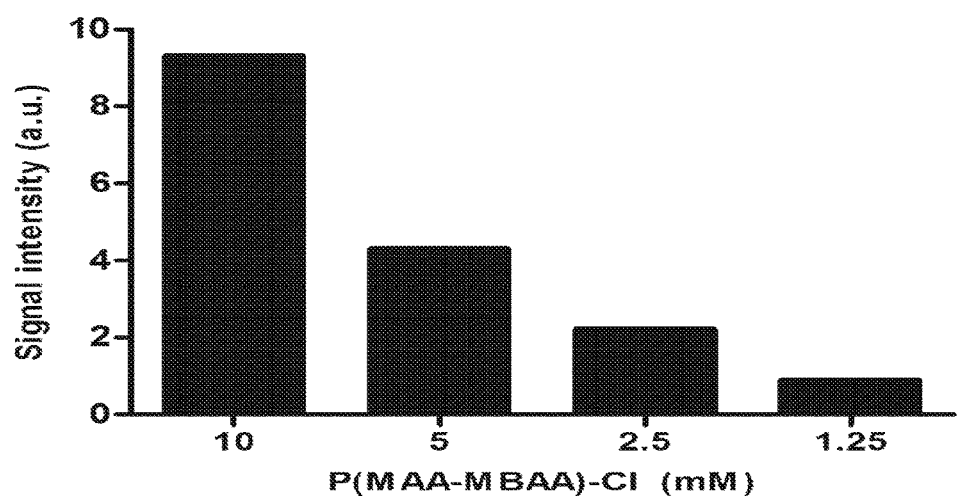

.OH free radicals are extremely toxic and notorious for their ability to cause cellular damages, including DNA damage and oxidation of lipids and amino acids in proteins. Thus, without being bound by any particular theory, the formation of ROS by P(MAA-MBAA)-Cl provides a mechanistic basis whereby these NPs exert detrimental effects. The proposed relationship between ROS production and bacterial killing is corroborated by our finding that lower concentrations of chlorinated NPs are associated with reduced production of the DMPO-OH quartet signal, and in turn, partial killing of bacteria (FIG. 38). In fact, low concentrations (1.25 mM) of P(MAA-MBAA)-Cl that do not kill the bacteria (FIG. 38) hardly trigger formation of ROS (FIG. 38). In summary, the $Cl^+$-charged NPs promote formation of ROS, which triggers the oxidative-type stress response and ultimately, results in cell death.

Figure 39A:
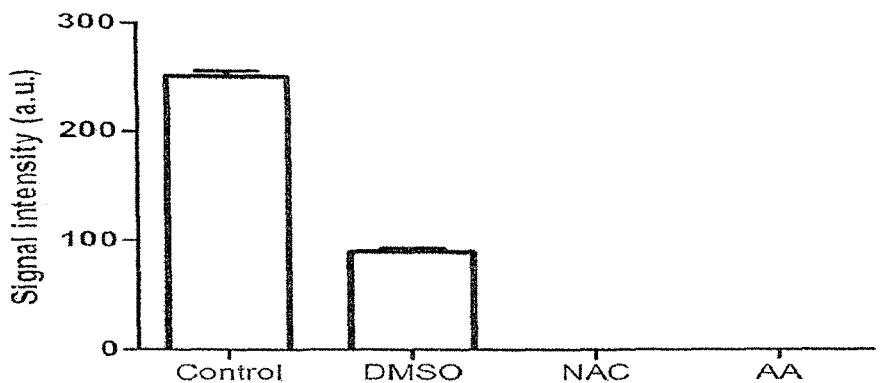
FIGS. 39A-C present graphs demonstrating ROS formation upon mixing P(MAA-MBAA)-Cl NPs with LB without (i.e. control) or with addition of either 10% DMSO, 10 mM NAC, or 10 mM AA (FIG. 39A). Killing kinetic curves of E. coli (FIG. 39B) and S. aureus (FIG. 39C) in the presence of P(MAA-MBAA)-Cl NPs that was pre-incubated with either double distilled water (DDW) (i.e. control) or the indicated antioxidants for 1 h before adding the relevant bacteria.
Figure 39B:
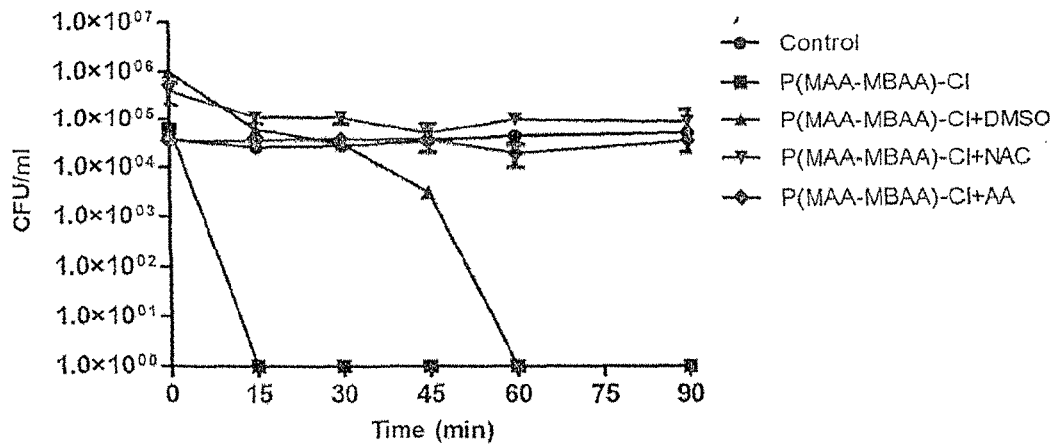
Figure 39C:
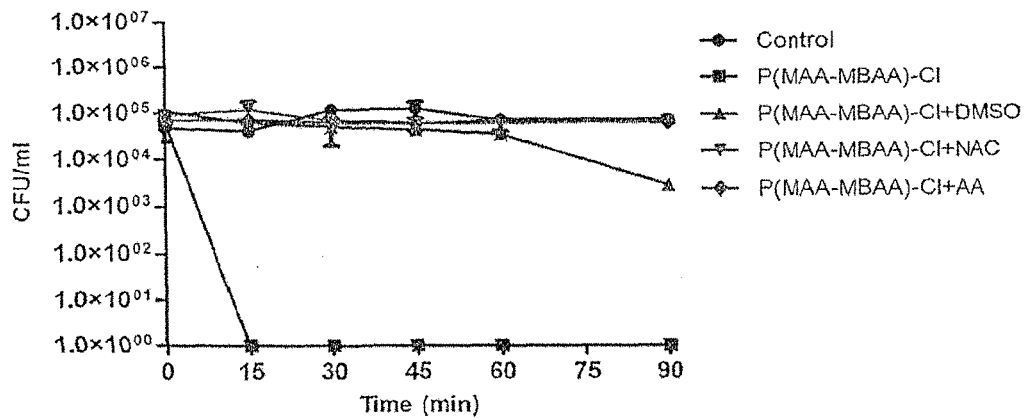

To further corroborate that the chlorinated NPs trigger formation of —OH and that these radicals are the cause for the antibacterial activity imparted by the NPs, exploited dimethyl sulfoxide (DMSO), N-acetyl cysteine (NAC) and Ascorbic acid (AA) were exploited as potent hydroxyl radical scavengers, serving as an established means of mitigating the deleterious effects of .OH. In line with a model that mixing P(MAA-MBAA)-Cl NPs with organic reagents leads to ROS formation, DMSO addition reduced the levels of DMPO-OH by 60%, while NAC and AA completely abrogated the formation of DMPO-OH (FIG. 39A). In light of these results, the effect of these antioxidants on the chlorinated NPs' antibacterial activity was examined. While the P(MAA-MBAA)-Cl NPs killed both *E. coli* (FIG. 39B) and *S. aureus* (FIG. 39C) in the presence of LB already after 15', pre incubation of the chlorinated NPs with either NAC or AA prior the addition of bacteria, abolished the killing properties of the NPs (FIGS. 39B-C). Of note, DMSO was less efficient at mitigating bacterial cell death, as after 60' *E. coli* bacteria were eliminated while at 90' the P(MAA-MBAA)-Cl NPs started to affect the growth of *S. aureus* (FIGS. 39 B-C), which was also reflected by the capacity of DMSO to compromise, but not eliminate the charged NPs' ability to mediate hydroxyl radicals formation (FIG. 39A).

Example 8

Degradation of Organic Materials

Method

To investigate the capability of P(MAA-MBAA)-Cl nanoparticles to degrade organic materials (i.e. self-cleaning properties), two easy-to-follow organic dyes, methylen blue (MB) and crystal violet (CV), were selected.

The P(MAA-MBAA)-Cl nanoparticle dispersion were shaken with the dyes and the concentration was monitored by spectrophotometer up to full degradation of the dye. The effect of two parameters, i.e. the incubation temperature and the nanoparticles concentration, on the dyes degradation was investigated.

In exemplary experiments, 200 µl of MB or CV (0.1 mg/ml) aqueous solution was mixed with 1.8 ml (8 mg/ml) of P(MAA-MBAA)-Cl nanoparticles aqueous dispersion in a 2 ml Eppendorf. Four different incubation temperatures were tested, i.e. room temperature, 50° C., 70° C., and 90° C. The concentration of MB and CV was monitored by spectrophotometer at the range of 500-750 nm to detect the main peaks at 666 nm and 597 nm, respectively. Samples were taken every 30 min for the first 5 h, then in larger time intervals until total disappearance of the peak. At 50, 70, and 90° C. the peak vanishes within the first 4 h. The experiments were performed in triplicates. The values were normalized relative to the dye concentration at the beginning of the experiment.

To assess the effect of the P(MAA-MBAA)-Cl nanoparticles concentration on the model dyes degradation, the same procedure was conducted at 90° C., using 1.8 ml of either 8 mg/ml or 1.6 mg/ml, of P(MAA-MBAA)-Cl nanoparticles and the analysis was performed as mentioned above.

Results

Figure 40:
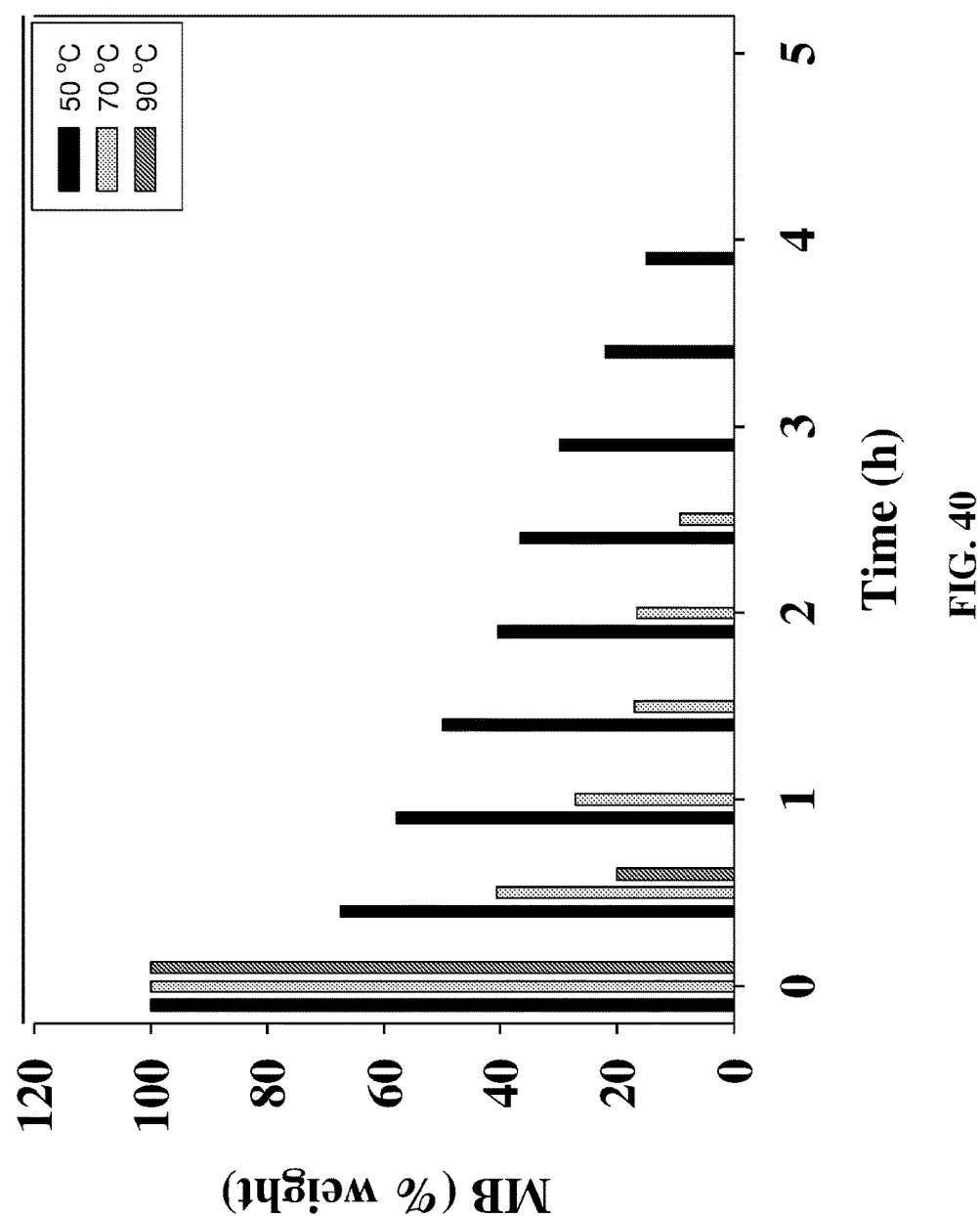
FIG. 40 presents graph demonstrating the kinetic study of methylene blue (MB) degradation by incubation with P(MAA-MBAA)-Cl nanoparticles.
Figure 41:
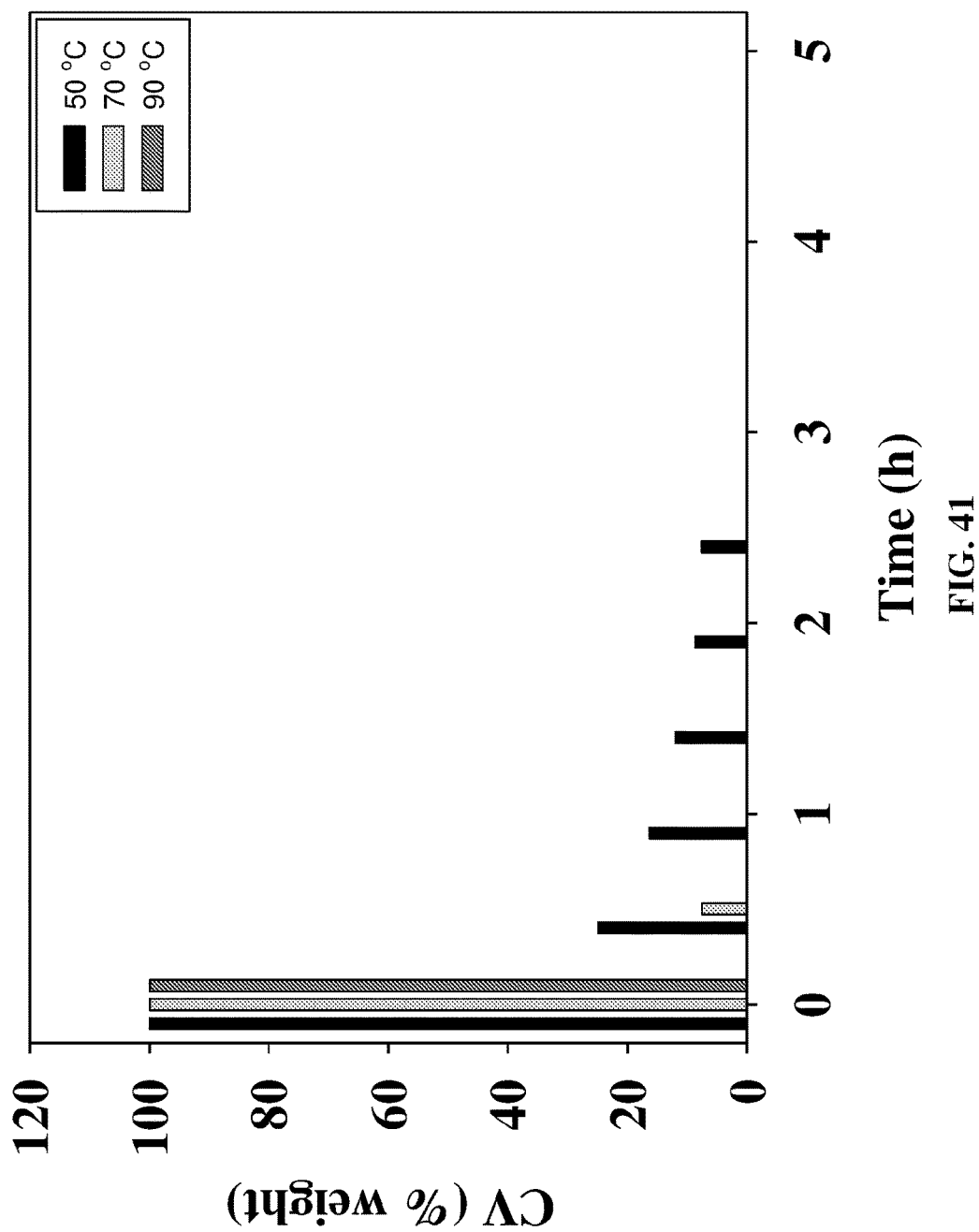
FIG. 41 presents graph demonstrating the kinetic study of crystal violet (CV) degradation by incubation with P(MAA-MBAA)-Cl nanoparticles.

The "self cleaning" ability of the P(MAA-MBAA)-Cl nanoparticles was determined using two model organic dyes, crystal violet (CV) and methylene blue (MB). Overall, CV was decomposed by the P(MAA-MBAA)-Cl nanoparticles faster than MB, as indicated by the comparison between FIG. 40 and FIG. 41.

Furthermore, the temperature significantly affected the degradation rates of the dyes by the P(MAA-MBAA)-Cl nanoparticles. Kinetic experiments at room temperature indicated that complete decomposition of CV and MB occurs after 80 and 120 h of incubation, respectively (data not shown). After 1 h of incubation at room temperature, 15% and 60% of the initial concentration of CV and MB were left, respectively. At 50° C., the complete degradation time of MB and CV was drastically shortened to 4.5 h and 3 h, respectively. The degradation rate shortened even more at 70° C. when complete degradation was achieved by incubation with the chlorinated nanoparticles for 3 h and 1 h, respectively. The fastest dye degradation was completed by heating the dyes solution with the chlorinated nanoparticles to 90° C. At this temperature, the total degradation of MB appeared within an hour of incubation and up to 30 min for the total degradation of CV.

Example 9

Antibacterial Coatings

Coating PET Films with P(MAA-MBAA) Nanoparticles:

Coatings of P(MAA-MBAA) nanoparticles onto A4 PET (polyethyleneterpthalate) films were prepared by suspending dry P(MAA-MBAA) nanoparticles (1.16 g) in a water based solvent resin solution (6.64 g, from Hanita Coatings Industry Ltd, Israel) for 5 h at room temperature. The particles' dispersion was then spread on the 23 µm PET film with a Mayer Rod, following by drying the P(MAA-MBAA) coating on the PET film for 1 minute at 120° C. and then for additional 3 h at 60° C. The dry P(MAA-MBAA)/PET film was then cut to the specimens of 5 cm long and 4 cm wide.

Chlorination of the PET Films Coated with the P(MAA-MBAA) Nanoparticles:

Specimens of 5 cm long and 4 cm wide of the P(MAA-MBAA)/PET films were cut. The active chlorine source, sodium hypochlorite solution (5% w/v), was adjusted to pH=7 by acetic acid titration. The P(MAA-MBAA)/PET film specimens were inserted to a flask containing the hypochlorite solution and then shaken for 30 min followed extensive rinses (50 mL) with water and dried by condensed air.

The bound-Cl content of the P(MAA-MBAA)-Cl/PET films was $3.75 \times 10^{-5}$ mol per specimen as determined by iodometric/thiosulfate titration by the following expression:

$$\text{bound} - \text{Cl(mM)} = \frac{N \times V \times 1000}{2}$$

where N is the normality (equiv/L) and V is the volume (L) of the titrated sodium thiosulfate solution.

Antibacterial Activity of P(MAA-MBAA)-Cl-Coated PET Films:

P(MAA-MBAA)-Cl-coated PET films at three different coating thicknesses (i.e. 1, 4 and 7.8 g/m2) were tested for their antibacterial properties using *E. coli* and *S. aureus*, representing Gram-negative and Gram-positive bacteria, respectively, as described hereinabove. 1 ml of LB 1% containing either *E. coli* or *S. aureus* at a concentration of $10^5$ CFU/ml were incubated overnight with the different films, each one at a dimension of 0.5 cm×4 cm or were left untreated (i.e. control). On the following day, samples of 200 µl were taken from each tube and transferred into the wells of the first row in a 96-well plate. Serial dilutions were carried out and the cells were spotted onto LB agar plates, followed by their incubation at 37° C. for 20 h. Cell growth was monitored and determined by viable cell count.

Results

Figure 42:
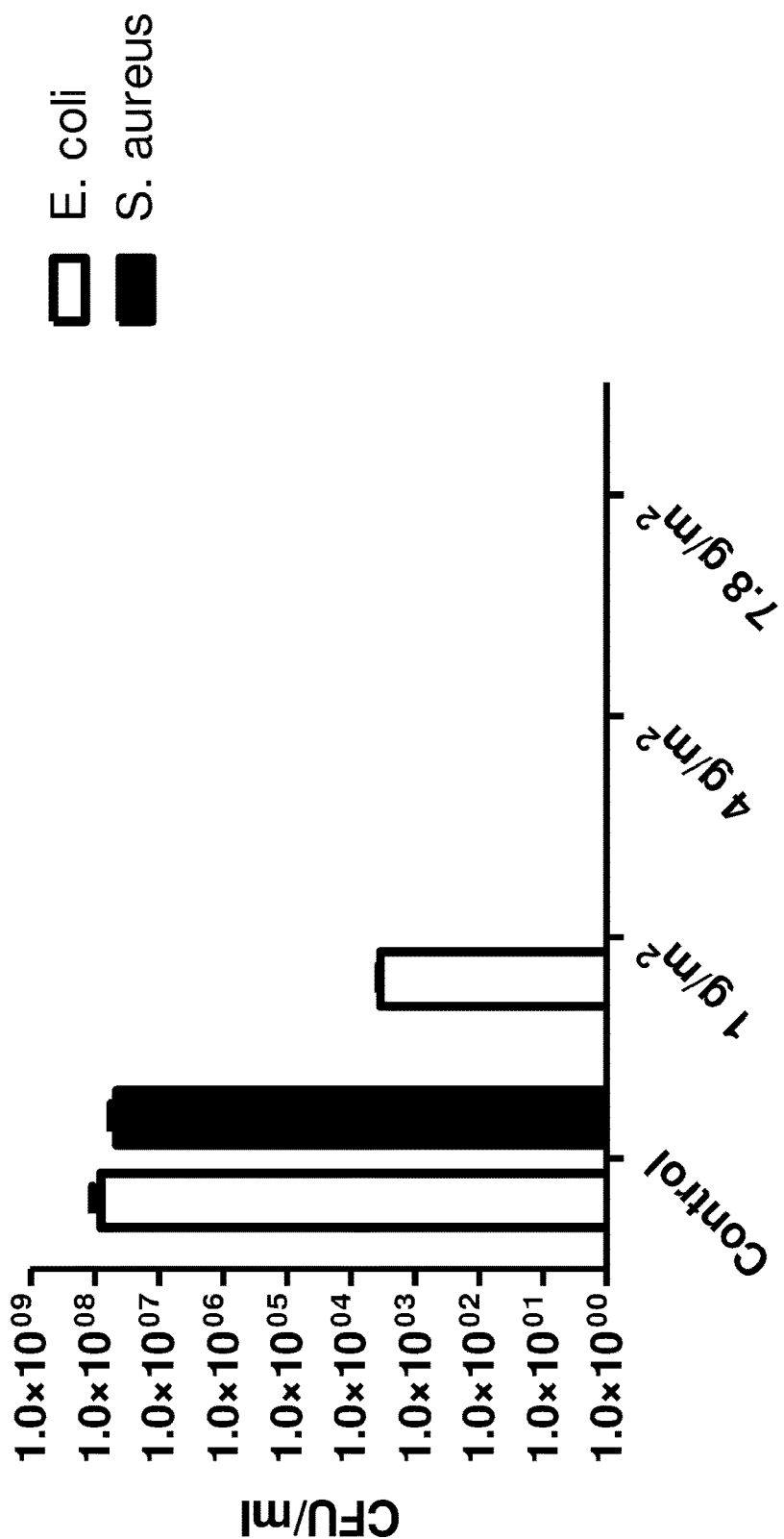
FIG. 42 is a bar graph demonstrating the antibacterial activity of P(MAA-MBAA)-Cl-coated polyethylene (PET) films. E. coli and S. aureus bacteria were both grown in the presence of P(MAA-MBAA)-Cl-coated PET films at increasing coating thicknesses or were left untreated (i.e. control).
Figure 43A:
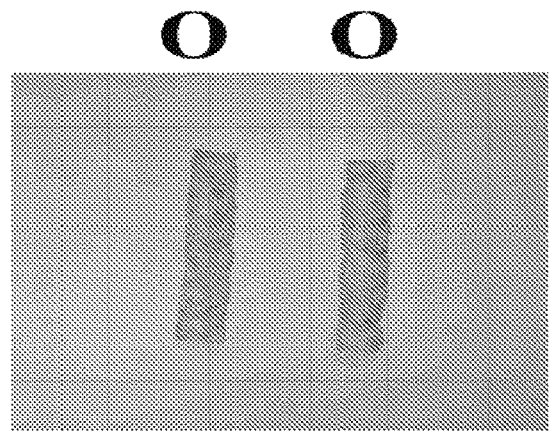
FIGS. 43A-E presents incubation of PE/P(MAA-MBAA) profiles in "Shafdan" sewage water. "I" designates chlorination of the profile while "O" designates the non chlorinated profile, in each cycle. Polyethylene profiles containing the P(MAA-MBAA) NPs were either chlorinated (left) or not (right) (FIG. 43A). PE/NPs and PE/Cl-NPS profiles in pipes were dipped for the first time for a month in flowed Shafdan waste water (FIG. 43B). A second cycle of chlorination and incubation for another month in Shafdan (FIG. 43C). A third cycle of chlorination and incubation for another month in Shafdan (FIG. 43D). A forth cycle of chlorination and incubation for two months in Shafdan. The antimicrobial activity of some embodiments of the composition of the invention in a sewage system (FIG. 43E).
Figure 43B:
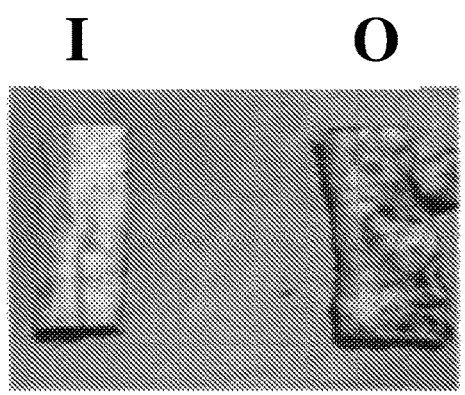
Figure 43C:
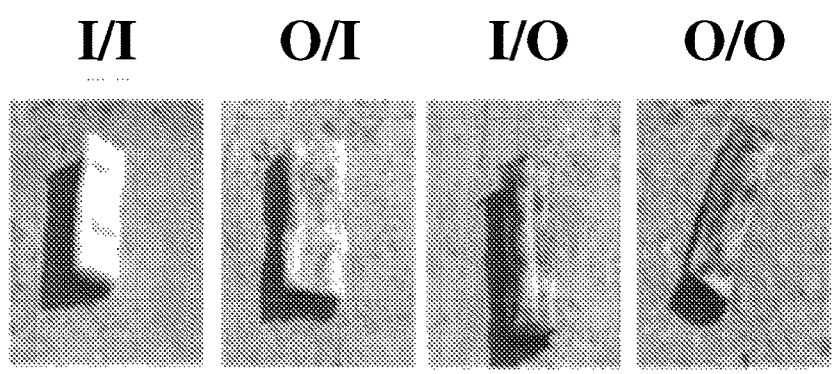
Figure 43D:
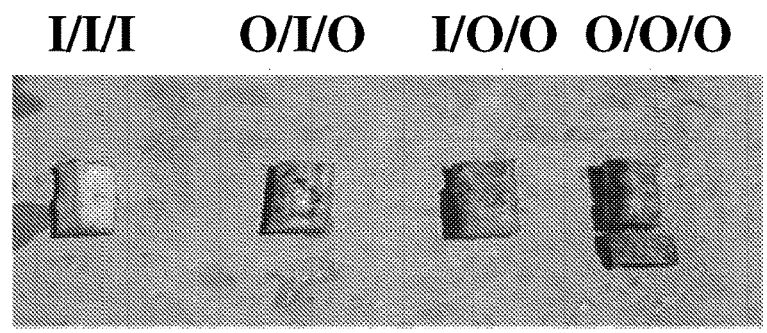
Figure 43E:
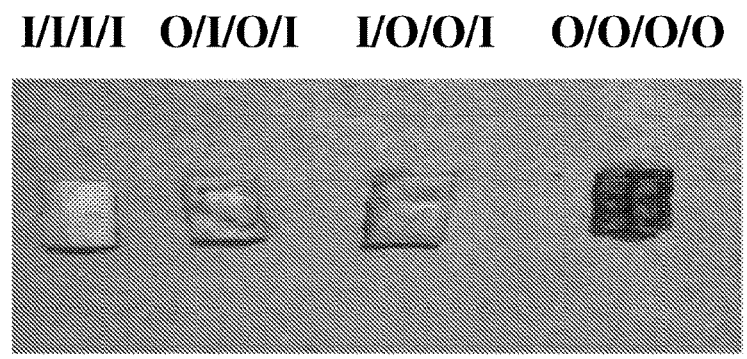

As shown in FIG. 42, films at coating thicknesses of 4 and 7.8 g/m$^2$ managed both to kill all the bacteria no matter which bacterial strain was applied. Nevertheless, films at a coating thickness of 1 g/m$^2$ were less efficient against *E. coli*, demonstrating a reduction of 4 logs, while *S. aureus* bacteria were more susceptible to the coating, and as such were completely eradicated.

Example 10

Sewage Experiments

Methods

Master Batch and PE/P(MAA-MBAA) Composite Nanoparticles Profile Preparation:

Antimicrobial plastic profiles were produced by dry mixing of linear low density polyethylene (LLDPE) with 1% of the P(MAA-MBAA) nanoparticles in a cast extrusion machine at 230° C. Samples in absence of the nanoparticles were also prepared and used as control.

Chlorination of the PE-P(MAA-MBAA):

cylinders of 8 cm length and radius of 1 cm of the PE/P(MAA-MBAA) profiles were shaken with 50 ml of sodium hypochlorite (4% w/v, neutralized by acetic acid for an hour, then washed four times with water (ddw) and dried with condensed air.

"Shafdan" Sewage Protocol:

Four pipes (32 mm) were connected to wasterwater from the Shafdan Treatment Plant which contains the household as well as the industrial wastewater of the Dan region (about 60% of Israel population). The flowing rate was maintained at 10 L/h. The chlorinated PE/P(MAA-MBAA), short name: PE/Cl-NPs, profiles were placed in the pipes for time ranges of month or two then were pictured immediately and recharged or placed again without any treatment for another cycle according the detailed description at the results section. This charging-recharging process was repeated 4 times.

Protein Determination Kit:

Quantification of the organic matter found on all the various profiles was done via the Bicinchoninic Acid (BCA) protein determination kit (Pierce).

Results

"Shafdan" Sewage:

The results are demonstrated in FIGS. 43A-E, and it can be observed that the leftmost PE profile which rechlorinated before every cycle appears to stay clean from bacteria and organic residues while the negative control, the rightmost sample, looks dirty i.e. full of biofilm coating. The two middle profiles which made almost the same way of chlorination, appears to look almost the same.

First Cycle (FIG. 43B):

8 cm PE/NPs and PE/Cl—NPS profiles in pipes were dipped for the first time for a month in flowed Shafdan waste water.

Second Cycle (FIG. 43C):

additional month in the Shafdan waste water. The samples were divided to 4 cm length in order to enlarge the experiment options. The left-facing arrows mark samples that were chlorinated, the two other samples were dipped with any other treatment.

Third Cycle (FIG. 43D):

Additional month in the Shafdan waste water. The left sample only was rechlorinated.

Forth Cycle (FIG. 43E):

Additional two months in the Shafdan waste water. The right sample was the only which was not treated.

It can be observed that the leftmost profile which rechlorinated before every cycle looks clean from bacteria and organic residues while the negative control, the rightmost sample, looks dirty full of biofilms. The two middle profiles which made almost the same way of chlorination, looks almost the same.

Figure 44A:
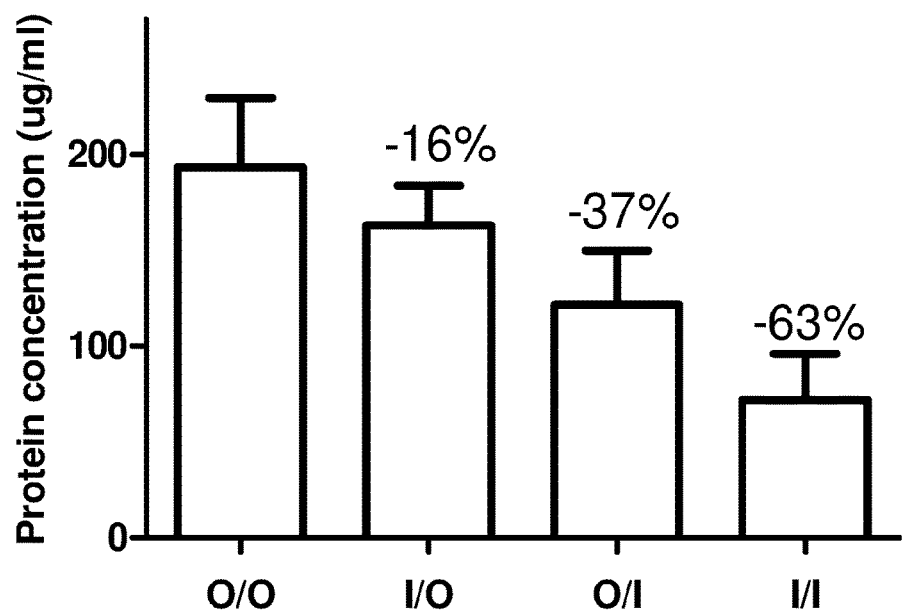
FIG. 44A shows the reduction in the protein levels of the various profiles through the two cycles and FIG. 44B shows the proteins levels at the end of the experiment, two months after the forth regeneration cycle was conducted.
Figure 44B:
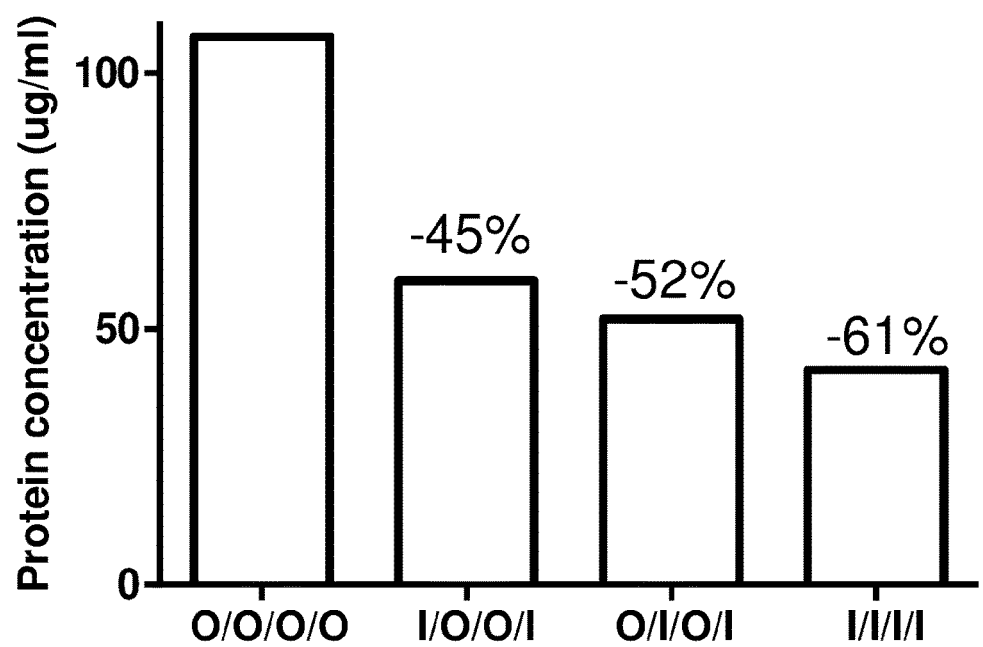

Protein Determination Kit:

As shown in FIG. 44A, profiles that were chlorinated prior to their incubation in Shafdan water but not in the second regeneration cycle (denoted as "I/O") have demonstrated a reduction of 16% in the organic biomass while profiles that were not chlorinated in the first cycle but only in the second one showed a decay of 37% in comparison to the control (denoted as "O/O"). The most prominent decay was achieved by profile I/I, in which the nanoparticles embedded within the profile were loaded with chlorine at both cycles (i.e. 63%). The protein analysis was also conducted at the end of the experiment (two months after the forth cycle was carried out). The profile that was chlorinated throughout all the experiment (denoted as "I/I/I/I") managed to reduce the protein quantity by 61% (FIG. 44B), while profiles that were chlorinated in the first or second cycles in addition to chlorine recharging in the third cycle have led to similar decays of 45% and 52%, respectively (FIG. 44B). It is important to emphasize that the reductions were probably more significant if all the organic matter found on the control was reduced in the experiments. Nevertheless, on the other profiles it could be seen that the NaOH lysis treatment managed to remove all the biomass. This might be due to the fact that the control profile contained such high load of biomass that the lysis treatment was not sufficient enough to remove all of the biomass and/or that the organic fouling is composed not only from proteins, but most likely from polysaccharides, lipids and nucleic acids as well, and thus other quantification methods should be applied.

Example 11

Anti-Fouling Coating on Dripper

Figure 45A:
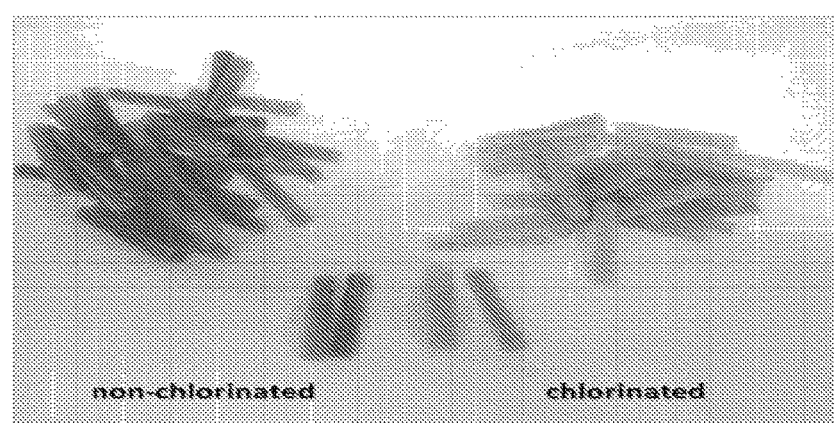
FIG. 45A presents photos showing the non-chlorinated vis-a-vis chlorinated drippers. The total biomass on the drippers was also imaged using environmental scanning electron microscopy (E-SEM): treated (right, bar is 100 µm and non-treated (left, bar is 500 µm) (FIG. 45B) and quantified via total organic carbon (FIG. 45C).
Figure 45B:
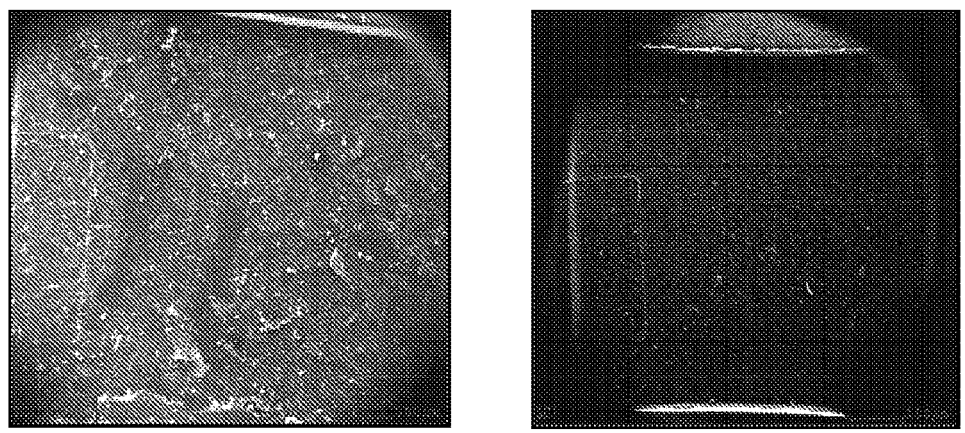
FIGS. 45 A-C present drippers containing the P(MAA-MBAA) NPs and their chlorinated (treated) counterparts following incubation for one month in sewage treated inigation water.
Figure 45C:
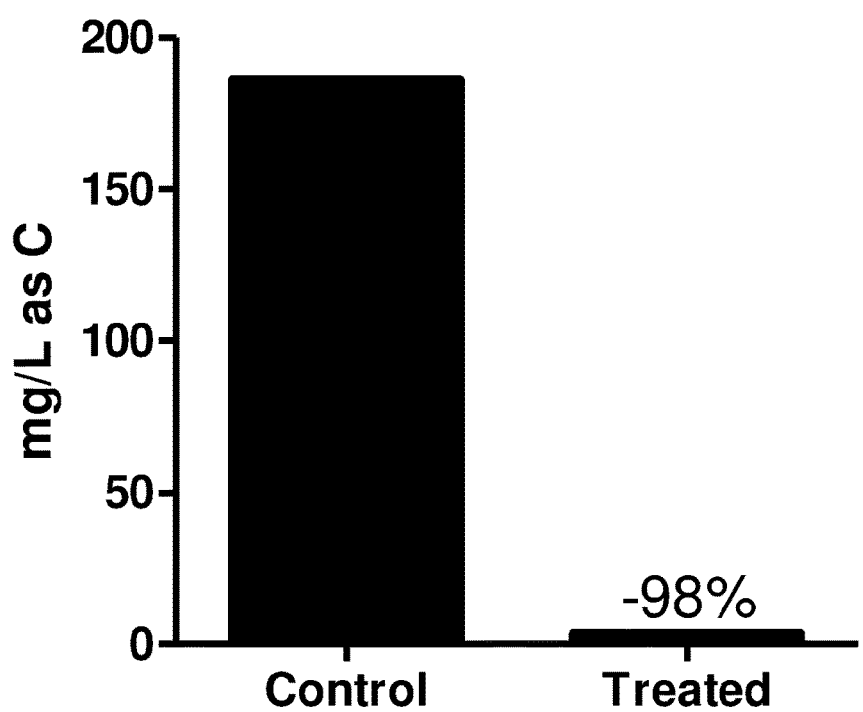

Method 200 drippers that had been imbedded with P(MAA-MBAA) NPs being either chlorinated using NaOCl or left untreated (i.e. control) were incubated in field study facility (operated by Netafim LTD.). After one month of incubation under constant flow of sewage treated irrigation water, the drips containing the chlorinated NPs had less biofouling as opposed to the control which had fouling on it (FIG. 45A). These results were visualized using environmental scanning electron microscopy (E-SEM) (FIG. 45B) and were further quantified via total organic carbon (FIG. 45C).

After 2.5 months of incubation in Hazerim, the results were still very significant, showing a clear difference between the control drippers to the treated ones. In addition, chlorinated drippers were taken after one month of incubation in Hazerim for regeneration with $Cl^+$, using NaOCl. The regenerated drippers were returned to the field and stored again in Hazerim for an additional month, and as shown in FIG. 46, the regenerated drips stayed cleaned and no fouling was observed on them. The experiments are still ongoing, but currently chlorinated drippers prevented fouling for more than 5 months.

Example 12

Cytotoxic Assays

Method

Mouse fibroblasts BALB/c 3T3 and rat alveolar macrophages NR8383 cell lines were both purchased from ATCC and cultured in petri dishes in either Dulbecco's Modification of Eagle's Medium (DMEM, ATCC 30-2002) containing 4 mM L-glutamine and supplemented with either 10% non-heat-inactivated newborn calf serum (NBCS, Biochrom Ag) or in Kaighn's Modification of Ham's F-12 Medium (ATCC 30-2004) containing 15% inactivated fetal bovine serum (FBS, Gibco Invitrogen), respectively. BALB/c 3T3 and NR8383 were seeded in 96-well plates at densities of ~3000 cells/well and 12000 cells/well, respectively. The cells were incubated at 37° C. in a humidified atmosphere of 5% CO2 for 24 h. In parallel, profiles pipes impregnated with either P(MAA-MBAA) nanoparticles or chlorinated ones were incubated with the growth medium used (w/o serum addition) for each cell line for 24 h as well. On the following day, BALB/c 3T3 cells were decanted from the growth medium used in the first day, and were then added with 50 µl of the medium that was incubated with the different profiles and 50 µl of a fresh medium to provide the cells with serum. For NR8383 cells, the procedure was changed a bit in light of their non-adherent properties, hence to the 50 µl of cells that were seeded a day before, 50 µl of the medium incubated with the profiles were added. One or three assays were conducted to determine the viability of NR8383 and BALB/c 3T3 cells, respectively. The assays were done as follows:

Water Soluble Tetrazolium Assay (WST-1 Assay):

This assay examines the activity of mitochondrial dehydrogenase enzymes, using WST-1 Cell Proliferation Reagent (Roche). Briefly, 10 µl of WST-1 reagent were added into each well followed by incubation at 37° C. 5% CO2 for 3 h (BALB/c 3T3 cells) or 1 h (NR8383 cells). After the incubation, the plates were shaken for 1 min and the absorption of the Formazan produced was detected at 450 nm.

Neutral Red Uptake (NRU) Assay:

This assay examines the ability of cells to incorporate neutral red dye in endosomes/lysosomes and vacuoles using neutral red solution (NR, Sigma). 48 h after the cells were exposed to the treated medium, the medium was removed of the wells followed by a wash with D-PBS (Lonza Walkersvillle, USA). 200 µl of NR solution were added to all wells and the plates were incubated at 37° C., 5% CO2 for 3 h. After incubation, the NR solution was removed and washing with D-PBS was done. Then, 100 µl of NR desorption solution (40 parts water, 50 parts ethanol, 10 parts acetic acid, freshly prepared) were added to all the wells. The plates were shaken for 30 min while they were protected from light, and then reading the absorption at 540 nm was done Adenosine Triphosphate (ATP) Assay:

24 h after the cells were exposed to the treated medium, 5 µl of 10% TCA were added to all the wells. Then, the plates were frozen at 80° C. for another 24 h. The levels of ATP were evaluated via ATP determination kit (Molecular probes).

Results

Figure 47A:
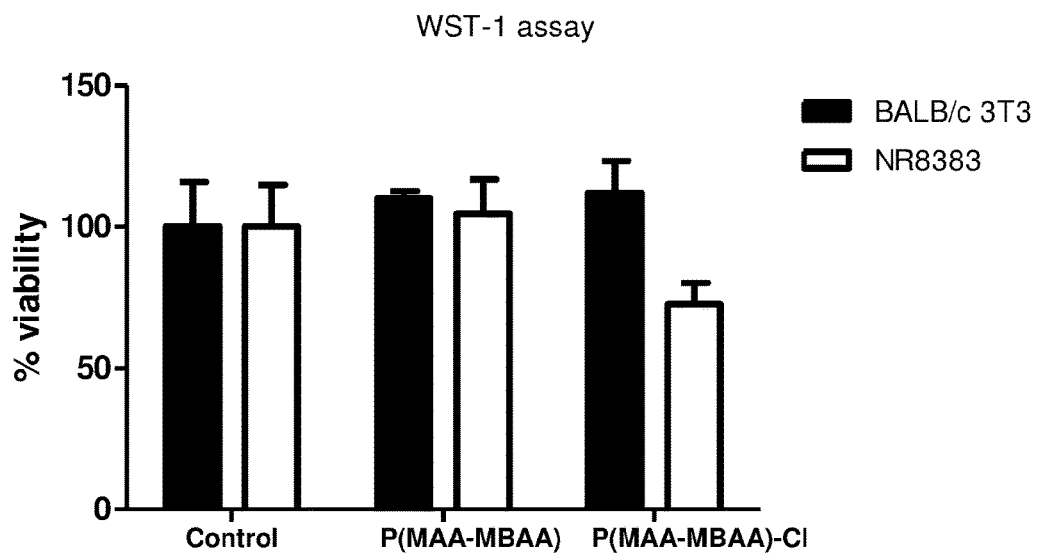
FIGS. 47A-C presents bar graph showing the biocompatibility of profiles impregnated with P(MAA-MBAA) nanoparticles or uncharged ones.
Figure 47B:
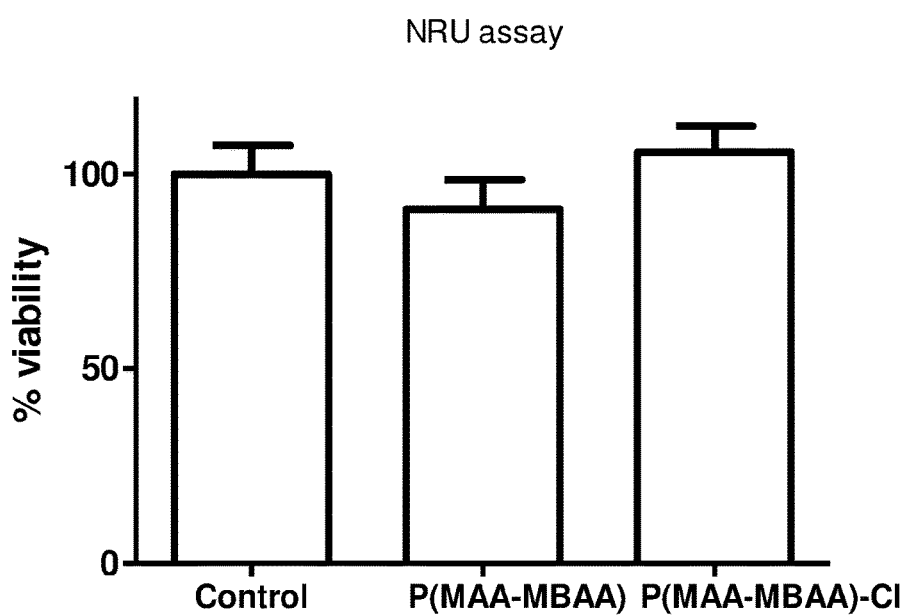
Figure 47C:
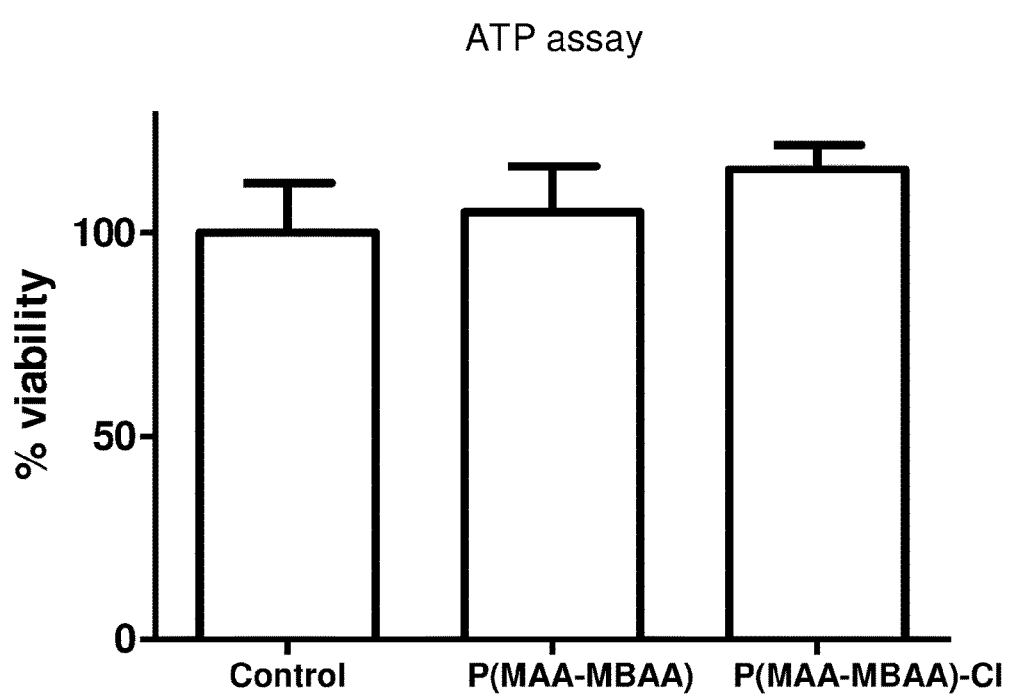

The results, obtained with PE/P(MAA-MBAA)-Cl composite nanoparticles profiles incubated in Shafdan water, have led us to examine any potential toxic effects that might be exerted by the chlorinated nanoparticles to the environment. The profiles were incubated with medium for 24 h and then, the medium was used for the growth of mouse fibroblasts BALB/c 3T3 and rat alveolar macrophages NR8383 cell lines. Three cytotoxicity assays were conducted with BALB/c 3T3 cells for WST-1 (FIG. 47A), NRU (FIG. 47B), and ATP (FIG. 47C) measurements. For NR8383 cells, only WST-1 assay was applied in light of their non-adherent characteristics. All assays performed with BALB/c 3T3 cells have shown that profiles coated with either P(MAA-MBAA) nanoparticles or the chlorinated ones do not release any reagents that might impart toxic effects to the cells (FIGS. 47 A-C). However, it seems like the viability of NR8383 cells was compromised a bit by chlorinated profiles, i.e. reduction of 28% in the viability in comparison to untreated cells or to cells treated with medium that was incubated with profile containing P(MAA-MBAA) nanoparticles.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition-of-matter comprising a plurality of crosslinked polymeric backbones, wherein at least 80% of said plurality of crosslinked polymeric backbones are characterized by an average hydrodynamic diameter of less than 500 nm, said crosslinked polymeric backbones being represented by the general Formula I:

wherein:
(a) $A_1$ is a monomeric unit derived from a secondary diamide compound, said secondary diamide compound being represented by the general formula II:

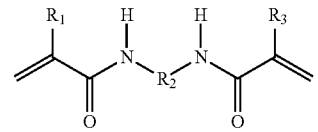

such that
$R_1$ and $R_3$ are hydrogen or a methyl group; and
$R_2$ is C1-C4 alkyl group;
(b) $A_2$ is a monomeric unit being a primary amide selected from the group consisting of: acrylamide, alkylacrylamide, and any derivative thereof;
(c) each of said plurality of polymeric backbones is crosslinked by at least one A1;
(d) B, in each instance, is a halogen atom independently selected from the group consisting of Cl, Br, and I, wherein said halogen atom, in one or more instances, is bound to the nitrogen belonging to said $A_1$ and/or to said $A_2$;
(e) x and y are integers, independently, representing the total numbers of A1 and A2, respectively, in said plurality of crosslinked polymeric backbones, said x and said y having a value of at least 5; and
(f) n represents the total numbers of said B.

2. The composition-of-matter of claim 1, wherein said $A_2$ is methacrylamide.

3. The composition-of-matter of claim 1, wherein said $A_1$ is selected from the group consisting of: N,N'-methylene bisacrylamide, N,N'-ethylene bisacrylamide, and any derivative thereof.

4. The composition-of-matter of claim 3, wherein said $A_1$ is N,N'-methylene bisacrylamide.

5. The composition-of-matter of claim 1, wherein said n has a value such that n/(x+y) multiplied by 100 is at least 0.1.

6. The composition-of-matter of claim 1, being in the form of a dry powder.

7. The composition-of-matter of claim 1, wherein said plurality of crosslinked polymeric backbones is characterized by an average hydrodynamic diameter of less than 50 nm with a size distribution of that varies within a range of less than 20%.

8. The composition-of-matter of claim 1, further comprising a substrate, wherein said plurality of crosslinked polymeric backbones is incorporated or coated in/on at least a portion of said substrate.

9. The composition-of-matter of claim 8, wherein said substrate is or forms a part of an article.

10. The composition-of-matter of claim 8, wherein said substrate comprises or is made of a polymer, wood, a metal, glass, carbon, a biopolymer and/or silicon.

11. An article comprising the composition-of-matter of claim 1.

12. The article of claim 11, being selected from the group consisting of a medical device, organic waste processing device, fluidic device, water system device, tubing, an agricultural device, a package, a sealing article, a fuel container and a construction element.

13. A method of inhibiting or reducing a formation of load of organic-based contaminant on or within an article, the method comprising incorporating or coating the composition-of-matter of claim 1 on and/or within said article.

14. The method of claim 13, wherein said load of organic-based contaminant is a load of a microorganism, and/or a formation of a biofilm or biofouling in and/or on an article, said microorganism being selected from the group consisting of: viruses, fungi, parasites, yeast, bacteria, and protozoa.

15. The method of claim 13, further comprising one or more dehalogenating-rehalogenating cycles with halogen atoms selected from the group consisting of Cl, Br, and I.

16. A process of preparing the composition-of-matter of claim 1, the process comprising:
co-polymerizing a plurality of said monomeric units, $A_1$ and $A_2$, said co-polymerizing comprising dispersing said monomers in a weight ratio of $A_1/A_2$ that ranges from about 1/9 to about 6/4 in a surfactant-free aqueous phase comprising at least one water soluble initiator,
to thereby obtain a plurality of crosslinked polymeric backbones characterized by an average hydrodynamic diameter of less than 500 nm with a size distribution of that varies within a range of less than 20%.

17. The process of claim 16, wherein said at least one water soluble initiator is selected from the group consisting of: $AIBNCO_2H$, $H_2O_2$ PPS (potassium persulfate) and AIBN (azobisisobutylonitrile).

18. The process of claim 17, wherein said surfactant-free aqueous phase further comprising one or more reducing agent selected from the group consisting of: a sulfite, a bisulfite, thiosulfate, formamidinesulfinic acid, and ascorbic acid.

19. The process of claim 16, further comprising a step of at least partially halogenating said polymeric material, by an addition of a halide source.

20. The composition-of-matter of claim 1, wherein at least 1% of the hydrogens bound to a nitrogen atom in the crosslinked polymeric backbones are substituted by a halogen atom.

* * * * *